(12) United States Patent
Siebel et al.

(10) Patent No.: US 10,113,002 B2
(45) Date of Patent: *Oct. 30, 2018

(54) ANTI-JAGGED ANTIBODIES AND METHODS OF USE

(71) Applicant: Genentech, Inc., South San Francisco, CA (US)

(72) Inventors: Christian W. Siebel, Berkeley, CA (US); Yan Wu, Foster City, CA (US)

(73) Assignee: Genentech, Inc., South San Francisco, CA (US)

( * ) Notice: Subject to any disclaimer, the term of this patent is extended or adjusted under 35 U.S.C. 154(b) by 413 days.

This patent is subject to a terminal disclaimer.

(21) Appl. No.: 14/421,103

(22) PCT Filed: Aug. 13, 2013

(86) PCT No.: PCT/US2013/054664
§ 371 (c)(1),
(2) Date: Feb. 11, 2015

(87) PCT Pub. No.: WO2014/028446
PCT Pub. Date: Feb. 20, 2014

(65) Prior Publication Data
US 2015/0232568 A1    Aug. 20, 2015

Related U.S. Application Data

(60) Provisional application No. 61/682,640, filed on Aug. 13, 2012, provisional application No. 61/784,332, filed on Mar. 14, 2013.

(51) Int. Cl.
| | | |
|---|---|---|
| *A61K 39/395* | (2006.01) | |
| *C07K 16/18* | (2006.01) | |
| *C07K 16/22* | (2006.01) | |
| *C07K 16/28* | (2006.01) | |
| *A61K 47/48* | (2006.01) | |
| *C07K 16/24* | (2006.01) | |
| *C07K 14/475* | (2006.01) | |
| *C07K 14/52* | (2006.01) | |
| *A61K 39/00* | (2006.01) | |
| *C07K 16/30* | (2006.01) | |

(52) U.S. Cl.
CPC ...... *C07K 16/2896* (2013.01); *A61K 39/3955* (2013.01); *A61K 47/48561* (2013.01); *C07K 16/18* (2013.01); *C07K 16/24* (2013.01); *A61K 39/395* (2013.01); *A61K 2039/505* (2013.01); *C07K 16/22* (2013.01); *C07K 16/30* (2013.01); *C07K 2317/24* (2013.01); *C07K 2317/56* (2013.01); *C07K 2317/565* (2013.01); *C07K 2317/567* (2013.01); *C07K 2317/76* (2013.01)

(58) Field of Classification Search
CPC .......... A61K 2039/505; A61K 39/3955; A61K 39/00; C07K 2317/76; C07K 2317/56; C07K 16/22; C07K 16/30; C07K 2317/565; C07K 16/2896; C07K 2316/96; C07K 2317/567; C07K 16/24
See application file for complete search history.

(56) References Cited

U.S. PATENT DOCUMENTS

| | | |
|---|---|---|
| 6,703,489 B1 | 3/2004 | Lewis et al. |
| 7,754,206 B2 | 7/2010 | Clarke et al. |
| 9,550,829 B2 * | 1/2017 | French ................. C07K 16/28 |
| 2003/0026805 A1 | 2/2003 | Athwal et al. |
| 2004/0101847 A1 | 5/2004 | Freier et al. |
| 2004/0133357 A1 | 7/2004 | Zhong et al. |
| 2004/0170626 A1 | 9/2004 | Schuurman et al. |
| 2006/0093599 A1 | 5/2006 | Gazit-Bornstein et al. |
| 2007/0141065 A1 | 6/2007 | Fuh et al. |
| 2008/0247951 A1 | 10/2008 | Koch et al. |
| 2008/0317760 A1 | 12/2008 | Gurney et al. |
| 2009/0081238 A1 | 3/2009 | Siebel et al. |
| 2010/0080808 A1 | 4/2010 | Siebel et al. |
| 2010/0111958 A1 | 5/2010 | Gurney et al. |
| 2010/0196385 A1 | 8/2010 | Bedian et al. |
| 2014/0314749 A1 | 10/2014 | French et al. |
| 2015/0232568 A1 | 8/2015 | Siebel et al. |
| 2015/0252117 A1 | 9/2015 | Chinn et al. |

FOREIGN PATENT DOCUMENTS

| | | |
|---|---|---|
| JP | 2009078998 A | 4/2009 |
| WO | 2003076664 A1 | 9/2003 |
| WO | 2004/019921 A2 | 3/2004 |
| WO | 2003077848 A3 | 10/2004 |
| WO | 2006/135949 | 12/2006 |
| WO | 2008/057144 A2 | 5/2008 |
| WO | 2008091641 A2 | 7/2008 |
| WO | WO 2008/140826 A1 | 11/2008 |
| WO | 2009/124931 A2 | 10/2009 |
| WO | 2010/005566 | 1/2010 |
| WO | 2010/039832 | 4/2010 |
| WO | 2011/063237 A2 | 5/2011 |

(Continued)

OTHER PUBLICATIONS

Cuevas et al. Meningioma transcription profiles reveal deregulatred Notch signaling pathway. Cancer Res 65(12): 5070-5075, 2005.*
Gray et al. Human ligands of the Notch receptor. Am J Pathol 154: 785-794, 1999.*
Kopantzev et al. Comparative gene expression analysis of proliferating stromal cells froma pancreatic ductal adenocarcinoma, panreatitis and normal pancreas. Cancer Res 72(8): Abstract 4277, Apr. 2012 (2 pages).*
Purow et al. Expression of Notch-1 and its ligands, delta-like 1 and jagged-1, is critical for glioma cell survival and proliferation. Cancer Res 65(6): 2353-2363, 2005).*

(Continued)

*Primary Examiner* — Bridget E Bunner
(74) *Attorney, Agent, or Firm* — McNeill Baur PLLC

(57) ABSTRACT

The disclosure provides anti-Jagged antibodies and methods of using the same.

21 Claims, 36 Drawing Sheets

Specification includes a Sequence Listing.

(56) References Cited

FOREIGN PATENT DOCUMENTS

| | | |
|---|---|---|
| WO | 2011063237 A | 5/2011 |
| WO | WO 2011/063237 A1 | 5/2011 |
| WO | 2013/052155 A1 | 4/2013 |
| WO | 2013/052155 A9 | 4/2013 |
| WO | 2013/192550 A2 | 12/2013 |
| WO | 2014/028446 A1 | 2/2014 |
| WO | 2014/151866 A1 | 9/2014 |

OTHER PUBLICATIONS

Andrisani et al., "Gene signatures in hepatocellular carcinoma (HCC)" Sem Cancer Biol 21:4-9 ( 2011).
Artavanis-Tsakonas et al., "Choosing a cell fate: a view from the Notch locus" Reviews 7(11-12) ( 1991).
Bork, et al., "Go hunting in sequence databases but watch out for the traps" Trends in Genetics 12(10):425-427 (Oct. 1996).
Bork, "Powers and Pitfalls in Sequence Analysis: The 70% hurdle" Genome Research(10):398-400 ( 2000).
Brenner, "Errors in genome annotation" Trends in Genetics 15(4):132-133 ( 1999).
Brorson, "Mutational analysis of avidity and fine specificity of anti-levan antibodies" J Immunol (added article title info), 163:6694-6701 (Dec. 1999).
Brown et al., "Tolerance of single, but not multiple, amino acid replacements in antibody VH CDR 2: a means of minimizing B cell wastage from somatic hypermutation?" The Journal of Immunology 156(9):3285-3291 ( 1996).
Brummell et al. et al., "Probing the combining site of an anti-carbohydrate antibody by saturation-mutagenesis: role of the heavy-chain CDR3 residues" Biochemistry 32(4):1180-1187 (Feb. 1993).
Burks, E., et al. et al., "In vitro scanning saturation mutagenesis of an antibody binding pocket" P Natl Acad Sci USA 94:412-417 ( 1997).
Cao et al., "Osteopontin as potential biomarker and therapeutic target in gastric and liver cancers" World J. Gastroenterol. 18(30):3923-3930 ( 2012).
Casset et al., "A peptide mimetic of an anti-CD4 monoclonal antibody by rational design" Biochem Bioph Res Co(307):198-205 ( 2003).
Chen et al., "An antibody drug conjugate targeting PMEL17" J. Biol. Chem. (Manuscript M112.361485), (May 21, 2012).
Colman, P.M., "Effects of amino acid sequence changes on antibody-antigen interactions" Res Immunol 145:33-36 ( 1994).
Darwiche et al., "Inhibition of Notch signaling affects hepatic oval cell response in rat model of 2AAF-PH" Dove Press 3:89-98 ( 2011).
Dill et al., "Constitutive Notch 2 Signaling Induces Hepatic Tumors in Mice" Hepatology 57:1607-1619 ( 2013).
Doerks et al., "Protein annotation: detective work for function prediction" Trends in Genetics 14(6):248-250 ( 1998).
Dooley et al., "Notch Signaling Plays a Critical Role in Experimental and Human Liver Fibrogenesis" J. Hepatol. 52( Suppl 1):S48 ( 2010).
Dorothy French, DVM. PhD, DACVP, "Microarray analysis reveals signaling pathways critical for hepatic progenitor cell survival and self-renewal" Slides ASIP Meeting, pp. 53 (Apr. 8, 2011).
Fan B et al., "Cholangiocarcinomas can originate from hepatocytes in mice" The Journal of clinical investigation 122(8):2911-2915 ( 2012).
Fiorotto, R. et al., "Progenitor Cell Activation and Liver Repair is Altered in Notch2 and RBP-J kappa-Defective Mice Exposed to Cholestatic Injuries" Journal of Hepatology 52(1):S45 (Apr. 2010).
Gao et al., "Expression of Jagged1 and its association with hepatitis B virus X protein in hepatocellular carcinoma" Biochemical and Biophysical Research Communications 356:341-347 ( 2007).
Gao et al., "Notch1 activation contributes to tumor cell growth and proliferation in human hepatocellular carcinoma HepG2 and SMMC7721 cells" International journal of oncology 41(5):1773-1781 ( 2012).

Geisler et al., "Liver-Specific Inactivation of Notch2, but not Notch1, Compromises Intrahepatic Bile Duct Development in Mice" Live Biology/Pathobiology 48(2):607-616 (Aug. 2008).
Gotoh et al., "Overexpression of osteopontin in hepatocellular carcinoma" Pathology International 52:19-24 ( 2002).
Groth et al., "Therapeutic Approaches to Modulating Notch Signaling: Current challenges and future prospects" Seminars in Cell & Development Biology 23:465-472 ( 2012).
Hattori et al., "Expression of the RNA-binding protein Musashi1 in adult liver stem-like cells" Hepatology Research 40:432-437.
Ho et al., "Advances in Liver Cancer AntibodyTherapies" Biodrugs 25(5):275-284 ( 2011).
Ho et al., "AKT (v-Akt Murine Thymoma Viral Oncogene Homolog 1) and N-Ras (Neuroblastoma Ras Viral Oncogene Homolog) Coactivation in the Mouse Liver Promotes Rapid Carcinogenesis by Way of mTOR (Mammalian Target of Rapamycin Complex 1), FOXM1 (Forkhead Box M1)/SKP2, and c-Myc Pathways" Hepatology 55:833-845 ( 2012).
Huntzicker et al., "Differential Effects of Targeting Notch Receptors in a Mouse Model of Liver Cancer" Hepatology 61:942-952 ( 2015).
Imrich et al., "EpCAM and its potential role in tumor-initiating cells" Cell Adhesion Migration 6:30-38 ( 2012).
International Search Report and Written Opinion for International App. No. PCT/US2014/026588, filed Mar. 13, 2014, pp. 23 (dated Aug. 20, 2014).
International Search Report and Written Opinion for PCT Application No. PCT/US2015/015456, filed Feb. 11, 2015, pp. 13 (dated May 7, 2015).
Jang et al., "The structural basis for DNA binding by an anti-DNA autoantibody" Mol Immunol. 35(18):1207-17 (Dec. 1998).
Jensen et al., "Transit-amplifying ductal (oval) cells and their hepatocytic progeny are characterized by a novel and distinctive expression of delta-like protein/preadipocyte factor 1/fetal antigen 1." Am Journal Physiol 164(4):1347-1359 ( 2004).
Kobayashi, H., et al. et al., "Tryptophan H33 plays an important role in pyrimidin (6-4) pyrimidone photoproduct binding by a high-affinity antibody" Protein Eng 12(10):879-884 ( 1999).
Koch et al., "Notch and Cancer: a double-edged sword" Cellular and Molecular Life Sciences 64:2746-2762 ( 2007).
Litten et al., "Activated NOTCH2 is Overexpressed in Hepatoblastomas: An Immunohistochemical Study" Pediatric Develop. Pathol. 14:378-383 ( 2011).
Louvi et al., "Notch and disease: A growing field" Seminars in Cell & Development Biology 23:473-480 ( 2012).
Lozier et al., "Notch signaling regulates bile duct morphogenesis in mice" PLoS One 3(3):e1851 ( 2008).
McCright et al., "A mouse model of Alagille syndrome: Notch2 as a genetic modifier of Jag1 haploinsufficiency" Development 129(4):1075-82 (Feb. 2002).
Mullendore et al., "Ligand-dependent Notch Signaling is Involved in Tumor Initiation and Tumor Maintenance in Pancreatic Cancer" Clinical Cancer Research 15:2291-2301 (Apr. 1, 2009).
Ngo et al., "Computational complexity, protein structure prediction, and the Levinthal paradox" The Protein Folding Problem and Tertiary Structure Prediction pp. 492-495 (1994).
Nijjar et al., "Notch receptor expression in adult human liver: a possible role in bile duct formation and hepatic neovascularization" Hepatology 34:1184-1192 ( 2001).
Nishina et al., "Restored expression of the tumor suppressor gene RUNX3 reduces cancer stem cells in hepatocellular carcinoma by suppressing Jagged1-Notch signaling" Oncology Reports 26:523-531 ( 2011).
Oda et al., "Mutations in the human Jagged1 gene are responsible for Alagille syndrome" Nat Genet. 16:235-42 (Jul. 1997).
Orr et al., "Mechanism of Action of the Antifibrogenic Compound Gliotoxin in Rat Liver Cells" Hepatology 40:232-242 ( 2004).
Pang et al., "Cancer stem cell as a potential therapeutic target in hepatocellular carcinoma" Current Cancer Drug Targets 12:1081-1094 ( 2012).
Piccoli et al., "Alagille syndrome and the Jagged1 gene" Semin Liver Dis. 21(4):525-34 ( 2001).

(56) References Cited

OTHER PUBLICATIONS

Pikarsky et al., "NF-kb functions as a tumour promoter in inflammation-associated cancer" Nature 43:461-468 (Sep. 23, 2004).
Qi et al., "Notch1 signaling inhibits growth of human hepatocellular carcinoma through induction of cell cycle arrest and apoptosis" Cancer Research(63):8323-8329 (Dec. 1, 2003).
Ryan et al., "Bile duct proliferation in Jag1/fringe heterozygous mice identifies candidate modifiers of the Alagille syndrome hepatic phenotype" Hepatology 48(6):1989-97 ( 2008).
Sakurai et al., "Loss of hepatic NF-kb activity enhances chemical hepatocarcinogenesis through sustained c-Jun N-terminal kinase 1 activation" PNAS 103(28):10544-10551 (Jul. 11, 2006).
Sekiya et al., "Intrahepatic cholangiocarcinoma can arise from Notch-mediated conversion of hepatocytes" The Journal of Clinical Investigation 122(11):3914-3918 ( 2012).
Shen et al., "GSI-has a better effect in inhibiting hepatocellular carcinoma cell growth than GSI-X, or GSI-XXI" Anticancer Drugs 23:683-690 ( 2012).
Shin et al., "SPP1 polymorphisms associated with HBV clearance and HCC occurrence" Intl. J. Epidemiology 36:1001-1008 ( 2007).
Skolnick et al., "From genes to protein structure and function: novel applications of computational approaches in the genomic era" Trends in Biotech. 18(1):34-39 ( 2000).
Smith et al., "The challenges of genome sequence annotation of 'the devil is in the details'" Nature Biotech(15):1222-1223 ( 1997).
Sparks et al., "Notch signaling regulates formation of the three-dimensional architecture of intrahepatic bile ducts in mice" Hepatology 51(4):1391-400 ( 2010).
Spee et al., "Characterisation of the activated liver progenitor cell niche, potential involvement of Wnt and Notch signalling" Gut (abstract only (2 pages)), 59:247-257 ( 2010).
Tanimizu et al., "Notch signaling controls hepatoblast differentiation by altering the expression of liver-enriched transcription factors" J Cell Science 117:3165-3174 ( 2004).
Tchorz et al., "Notch2 signaling promotes biliary epithelial cell fate specification and tubulogenesis during bile duct development in mice" Hepatology 50(3):871-9 ( 2009).
Tokuriki, et al., "Stability effects of mutations and protein evolvability" Current Opinion in Structural Biology 19:596-604 (2009).
Vajdos et al., "Comprehensive Functional Maps of the Antigen-binding Site of an Anti-ErbB2 Antibody Obtained with Shotgun Scanning Mutagenesis" Journal of Molecular Biology 320:415-428 ( 2002).
Viatour et al., "Notch signaling inhibits hepatocellular carcinoma following inactivation of the RB pathway" The Journal of Experimental Medicine 208(10):1963-1976 (Aug. 29, 2011).
Villanueva et al., "Notch Signaling is Activated in Human Hepatocellular Carcinoma and Induces Tumor Formation in Mice" Gastroenterology 143:1660-1669 ( 2012).
Wakabayashi et al., "Regulation of Notch1 Signaling by Nrf2: Implications for Tissue Regeneration" Science Signaling 3(130):1-11 (Jul. 13, 2010).
Wang et al., "Hepatitis B Virus X protein promotes the growth of hepatocellular carcinoma by modulation of the Notch signaling pathway" Oncology Reports 27:1170-1176 ( 2012).
Wang et al., "Notch1 signaling contributes to the oncogenic effect of HBx on human hepatic cells" Biotechnol. Lett 35:29-37 ( 2012).
Wang et al., "Notch1 signaling sensitizes tumor necrosis factor-related apoptosis-inducing ligand-induced apoptosis in human hepatocellular carcinoma cells by inhibiting Akt/Hdm2-mediated p53 degradation and up-regulating p53-dependent DR5 expression" Journal of Biological Chemistry 284(24):16183-16190 ( 2009).
Wells, "Additivity of Mutational Effects in Proteins" Biochemistry 29:8509-8517 (1990).
Wu et al. et al., "Therapeutic Antibody targeting of individual Notch receptors" Nature 464:1052-1057 ( 2010).
Wu et al., "Notch Signaling and its role in breast cancer" Frontiers in Bioscience 12:4370-4383 ( 2007).
Xu et al., "Yes-Associated Protein is an Independent Prognostic Marker in Hepatocellular Carcinoma" Cancer(115):4576-85 (Oct. 1, 2009).
Yuen et al., "Serological markers of liver cancer" Best Practice & Research Clinical Gastroenterology 19(1):91-99 ( 2005).
Zender et al., "Identification and Validation of Oncogenes in Liver Cancer Using an Integrative Oncogenomic Approach" Cell(125):1253-1267 (Jun. 30, 2006).
Zeuner et al., "The Notch2-Jagged1 interaction mediates stem cell factor signaling in erythropoiesis" Cell Death Differ. 18(2):371-80 ( 2011).
Zhou et al., "Downregulation of the Notch signaling pathway inhibits hepatocellular carcinoma cell invasion by inactivation of matrix metalloproteinase-2 and-9 and vascular endothelial growth factor" Oncology reports 28(3):874-882 ( 2012).
Zhou et al., "The Down-Regulation of Notch1 Inhibits the Invasion and Migration of Hepatocellular Carcinoma Cells by Inactivating the Cyclooxygenase-2/Snail/E-cadherin Pathway In Vitro" Dig. Dis Sci ( 2012).
International Search Report dated Dec. 3, 2013, for International Patent Application No. PCT/US2013/054664 (5 pages).
Written Opinion dated Dec. 3, 2013, for International Patent Application No. PCT/US2013/054664 (5 pages).
Vartanyan, A.A. et al., Blocking the Notch signaling pathway stabilizes vasculogenic mimicry in melanoma, Russian Biotherapeutical Journal, 2012, v. 11 (see pp. 3-5).

\* cited by examiner

HUMAN Jag1 (SEQ ID NO:1)

MRSPRTRGRSGRPLSLLLALLCALRAKVCGASGQFELEILSMQNVNGELQNGNCCGGARN
PGDRKCTRDECDTYFKVCLKEYQSRVTAGGPCSFGSGSTPVIGGNTFNLKASRGNDRNRI
VLPFSFAWPRSYTLLVEAWDSSNDTVQPDSIIEKASHSGMINPSRQWQTLKQNTGVAHFE
YQIRVTCDDYYYGFGCNKFCRPRDDFFGHYACDQNGNKTCMEGWMGPECNRAICRQGCSP
KHGSCKLPGDCRCQYGWQGLYCDKCIPHPGCVHGICNEPWQCLCETNWGGQLCDKDLNYC
GTHQPCLNGGTCSNTGPDKYQCSCPEGYSGPNCEIAEHACLSDPCHNRGSCKETSLGFEC
ECSPGWTGPTCSTNIDDCSPNNCSHGGTCQDLVNGFKCVCPPQWTGKTCQLDANECEAKP
CVNAKSCKNLIASYYCDCLPGWMGQNCDININDCLGQCQNDASCRDLVNGYRCICPPGYA
GDHCERDIDECASNPCLNGGHCQNEINRFQCLCPTGFSGNLCQLDIDYCEPNPCQNGAQC
YNRASDYFCKCPEDYEGKNCSHLKDHCRTTPCEVIDSCTVAMASNDTPEGVRYISSNVCG
PHGKCKSQSGGKFTCDCNKGFTGTYCHENINDCESNPCRNGGTCIDGVNSYKCICSDGWE
GAYCETNINDCSQNPCHNGGTCRDLVNDFYCDCKNGWKGKTCHSRDSQCDEATCNNGGTC
YDEGDAFKCMCPGGWEGTTCNIARNSSCLPNPCHNGGTCVVNGESFTCVCKEGWEGPICA
QNTNDCSPHPCYNSGTCVDGDNWYRCECAPGFAGPDCRININECQSSPCAFGATCVDEIN
GYRCVCPPGHSGAKCQEVSGRPCITMGSVIPDGAKWDDDCNTCQCLNGRIACSKVWCGPR
PCLLHKGHSECPSGQSCIPILDDQCFVHPCTGVGECRSSSLQPVKTKCTSDSYYQDNCAN
ITFTFNKEMMSPGLTTEHICSELRNLNILKNVSAEYSIYIACEPSPSANNEIHVAISAED
IRDDGNPIKEITDKIIDLVSKRDGNSSLIAAVAEVRVQRRPLKNRTDFLVPLLSSVLTVA
WICCLVTAFYWCLRKRRKPGSHTHSASEDNTTNNVREQLNQIKNPIEKHGANTVPIKDYE
NKNSKMSKIRTHNSEVEEDDMDKHQQKARFAKQPAYTLVDREEKPPNGTPTKHPNWTNKQ
DNRDLESAQSLNRMEYIV

MURINE Jag1 (SEQ ID NO:2)

MRSPRTRGRPGRPLSLLLALLCALRAKVCGASGQFELEILSMQNVNGELQNGNCCGGVRN
PGDRKCTRDECDTYFKVCLKEYQSRVTAGGPCSFGSGSTPVIGGNTFNLKASRGNDRNRI
VLPFSFAWPRSYTLLVEAWDSSNDTIQPDSIIEKASHSGMINPSRQWQTLKQNTGIAHFE
YQIRVTCDDHYYGFGCNKFCRPRDDFFGHYACDQNGNKTCMEGWMGPDCNKAICRQGCSP
KHGSCKLPGDCRCQYGWQGLYCDKCIPHPGCVHGTCNEPWQCLCETNWGGQLCDKDLNYC
GTHQPCLNRGTCSNTGPDKYQCSCPEGYSGPNCEIAEHACLSDPCHNRGSCKETSSGFEC
ECSPGWTGPTCSTNIDDCSPNNCSHGGTCQDLVNGFKCVCPPQWTGKTCQLDANECEAKP
CVNARSCKNLIASYYCDCLPGWMGQNCDININDCLGQCQNDASCRDLVNGYRCICPPGYA
GDHCERDIDECASNPCLNGGHCQNEINRFQCLCPTGFSGNLCQLDIDYCEPNPCQNGAQC
YNRASDYFCKCPEDYEGKNCSHLKDHCRTTTCEVIDSCTVAMASNDTPEGVRYISSNVCG
PHGKCKSQSGGKFTCDCNKGFTGTYCHENINDCESNPCKNGGTCIDGVNSYKCICSDGWE
GAHCENNINDCSQNPCHYGGTCRDLVNDFYCDCKNGWKGKTCHSRDSQCDEATCNNGGTC
YDEVDTFKCMCPGGWEGTTCNIARNSSCLPNPCHNGGTCVVNGDSFTCVCKEGWEGPICT
QNTNDCSPHPCYNSGTCVDGDNWYRCECAPGFAGPDCRININECQSSPCAFGATCVDEIN
GYQCICPPGHSGAKCHEVSGRSCITMGRVILDGAKWDDDCNTCQCLNGRVACSKVWCGPR
PCRLHKSHNECPSGQSCIPVLDDQCFVRPCTGVGECRSSSLQPVKTKCTSDSYYQDNCAN
ITFTFNKEMMSPGLTTEHICSELRNLNILKNVSAEYSIYIACEPSLSANNEIHVAISAED
IRDDGNPVKEITDKIIDLVSKRDGNSSLIAAVAEVRVQRRPLKNRTDFLVPLLSSVLTVA
WVCCLVTAFYWCVRKRRKPSSHTHSAPEDNTTNNVREQLNQIKNPIEKHGANTVPIKDYE
NKNSKMSKIRTHNSEVEEDDMDKHQQKVRFAKQPVYTLVDREEKAPSGTPTKHPNWTNKQ
DNRDLESAQSLNRMEYIV

*FIG. 1*

HUMAN Jag2 (SEQ ID NO:3)

MRAQGRGRLPRRLLLLLALWVQAARPMGYFELQLSALRNVNGELLSGACCDGDGRTTRAG
GCGHDECDTYVRVCLKEYQAKVTPTGPCSYGHATPVLGGNSFYLPPAGAAGDRARARAR
AGGDQDPGLVVIPFQFAWPRSFTLIVEAWDWNDTTPNEELLIERVSHAGMINPEDRWKS
LHFSGHVAHLELQIRVRCDENYYSATCNKFCRPRNDFFGHYTCDQYGNKACMDGWMGKEC
KEAVCKQGCNLLHGGCTVPGECRCSYGWQGRFCDECVPYPGCVHGSCVEPWQCNCETNWG
GLLCDKDLNYCGSHHPCTNGGTCINAEPDQYRCTCPDGYSGRNCEKAEHACTSNPCANGG
SCHEVPSGFECHCPSGWSGPTCALDIDECASNPCAAGGTCVDQVDGFECICPEQWVGATC
QLDANECEGKPCLNAFSCKNLIGGYYCDCIPGWKGINCHINVNDCRGQCQHGGTCKDLVN
GYQCVCPRGFGGRHCELERDECASSPCHSGGLCEDLADGFHCHCPQGFSGPLCEVDVDLC
EPSPCRNGARCYNLEGDYYCACPDDFGGKNCSVPREPCPGGACRVIDGCGSDAGPGMPGT
AASGVCGPHGRCVSQPGGNFSCICDSGFTGTYCHENIDDCLGQPCRNGGTCIDEVDAFRC
FCPSGWEGELCDTNPNDCLPDPCHSRGRCYDLVNDFYACDDGWKGKTCHSREFQCDAYT
CSNGGTCYDSGDTFRCACPPGWKGSTCAVAKNSSCLPNPCVNGGTCVGSGASFSCICRDG
WEGRTCTHNTNDCNPLPCYNGGICVDGVNWFRCECAPGFAGPDCRINIDECQSSPCAYGA
TCVDEINGYRCSCPPGRAGPRCQEVIGFGRSCWSRGTPFPHGSSWVEDCNSCRCLDGRRD
CSKVWCGWKPCLLAGQPEALSAQCPLGQRCLEKAPGQCLRPPCEAWGECGAEEPPSTPCL
PRSGHLDNNCARLTLHFNRDHVPQGTTVGAICSGIRSLPATRAVARDRLLVLLCDRASSG
ASAVEVAVSFSPARDLPDSSLIQGAAHAIVAAITQRGNSSLLLAVTEVKVETVVTGGSST
GLLVPVLCGAFSVLWLACVVLCVWWTRKRRKERERSRLPREESANNQWAPLNPIRNPIER
PGGHKDVLYQCKNFTPPPRRADEALPGPAGHAAVREDEEDEDLGRGEEDSLEAEKFLSHK
FTKDPGRSPGRPAHWASGPKVDNRAVRSINEARYAGKE

MURINE Jag2 (SEQ ID NO:4)

MRARGWGRLPRRLLLLLVLCVQATRPMGYFELQLSALRNVNGELLSGACCDGDGRTTRAG
GCGRDECDTYVRVCLKEYQAKVTPTGPCSYGYATPVLGGNSFYLPPAGAAGDRARARSR
TGGHQDPGLVVIPFQFAWPRSFTLIVEAWDWNDTTPDEELLIERVSHAGMINPEDRWKS
LHFSGHVAHLELQIRVRCDENYYSATCNKFCRPRNDFFGHYTCDQYGNKACMDGWMGKEC
KEAVCKQGCNLLHGGCTVPGECRCSYGWQGKFCDECVPYPGCVHGSCVEPWHCDCETNWG
GLLCDKDLNYCGSHHPCVNGGTCINAEPDQYLACPDGYLGKNCERAEHACASNPCANGG
SCHEVPSGFECHCPSGWSGPTCALDIDECASNPCAAGGTCVDQVDGFECICPEQWVGATC
QLDANECEGKPCLNAFSCKNLIGGYYCDCLPGWKGINCQININDCHGQCQHGGTCKDLVN
GYQCVCPRGFGGRHCELEYDKCASSPCRRGGICEDLVDGFRCHCPRGLSGLHCEVDMDLC
EPSPCLNGARCYNLEGDYYCACPEDFGGKNCSVPRDTCPGGACRVIDGCGFEAGSRARGV
APSGICGPHGHCVSLPGGNFSCICDSGFTGTYCHENIDDCMGQPCRNGGTCIDEVDSFRC
FCPSGWEGELCDINPNDCLPDPCHSRGRCYDLVNDFYACDDGWKGKTCHSREFQCDAYT
CSNGGTCYDSGDTFRCACPPGWKGSTCTIAKNSSCVPNPCVNGGTCVGSGDSFSCICRDG
WEGRTCTHNTNDCNPLPCYNGGICVDGVNWFRCECAPGFAGPDCRINIDECQSSPCAYGA
TCVDEINGYRCSCPPGRSGPRCQEVVIFTRPCWSRGMSFPHGSSWMEDCNSCRCLDGHRD
CSKVWCGWKPCLLSGQPSDPSAQCPPGQQCQEKAVGQCLQPPCENWGECTAEEPLPPSTP
CQPRSSHLDNNCARLTLRFNRDQVPQGTTVGAICSGIRALPATRAAAHDRLLLLLCDRAS
SGASAVEVAMSFSPARDLPDSSLIQSTAHAIVAAITQRGNSLLLAVTEVKVETVVMGGS
STGLLVPVLCSVFSVLWLACVVICVWWTRKRRKERERSRLPRDESTNNQWAPLNPIRNPI
ERPGGSLGTGGHKDILYQCKNFTPPPRRAGEALPGPAGHGAGGEDEEDEELSRGDGDSP
EAEKFISHKFTKDPSCSLGRPACWAPGPKVDNRAVRSTKDVRRAGRE

*FIG. 2*

Sequence of expressed protein murine Jag1-DSL-EGF1-4 (mouse Jag1 antigen)

ADLGSQFELEILSMQNVNGELQNGNCCGGVRNPGDRKCTRDECDTYFKVCLKEYQSRVTAGGPC
SFGSGSTPVIGGNTFNLKASRGNDRNRIVLPFSFAWPRSYTLLVEAWDSSNDTIQPDSIIEKAS
HSGMINPSRQWQTLKQNTGIAHFEYQIRVTCDDHYYGFGCNKFCRPRDDFFGHYACDQNGNKTC
MEGWMGPDCNKAICRQGCSPKHGSCKLPGDCRCQYGWQGLYCDKCIPHPGCVHGTCNEPWQCLC
ETNWGGQLCDKDLNYCGTHQPCLNRGTCSNTGPDKYQCSCPEGYSGPNCEIAEHACLSDPCHNR
GSCKETSSGFECECSPGWTGPTCSTNIDDEFGLVPRGSGHHHHHH (SEQ ID NO. 5)

*FIG. 3A*

Sequence of expressed protein human Jag1-DSL-EGF1-4 (human Jag1 antigen)

QFELEILSMQNVNGELQNGNCCGGARNPGDRKCTRDECDTYFKVCLKEYQSRVTAGGPCSFGSG
STPVIGGNTFNLKASRGNDRNRIVLPFSFAWPRSYTLLVEAWDSSNDTVQPDSIIEKASHSGMI
NPSRQWQTLKQNTGVAHFEYQIRVTCDDYYYGFGCNKFCRPRDDFFGHYACDQNGNKTCMEGWM
GPECNRAICRQGCSPKHGSCKLGDCRCQYGWQGLYCDKCIPHPGCVHGICNEPWQCLCETNWGG
QLCDKDLNYCGTHQPCLNGGTCSNTGPDKYQCSCPEGYSGPNCEIAEHACLSDPCHNRGSCKET
SLGFECECSPGWTGPTCSTNIDD (SEQ ID NO. 6)

*FIG. 3B*

Sequence of expressed protein murine Jag2-DSL-EGF1-4 (mouse Jag2 antigen)

ADLGSMGYFELQLSALRNVNGELLSGACCDGDGRTTRAGGCGRDECDTYVRVCLKEYQAKVTPT
GPCSYGYGATPVLGGNSFYLPPAGAAGDRARARSRTGGHQDPGLVVIPFQFAWPRSFTLIVEAW
DWDNDTTPDEELLIERVSHAGMINPEDRWKSLHFSGHVAHLELQIRVRCDENYYSATCNKFCRP
RNDFFGHYTCDQYGNKACMDGWMGKECKEAVCKQGCNLLHGGCTVPGECRCSYGWQGKFCDECV
PYPGCVHGSCVEPWHCDCETNWGGLLCDKDLNYCGSHHPCVNGGTCINAEPDQYLCACPDGYLG
KNCERAEHACASNPCANGGSCHEVPSGFECHCPSGWNGPTCALDIDEEFGLVPRGSGHHHHHH
(SEQ ID NO. 7)

*FIG. 3C*

Sequence of expressed protein human Jag2-DSL-EGF1-4 (human Jag2 antigen)

ARPMGYFELQLSALRNVNGELLSGACCDGDGRTTRAGGCGHDECDTYVRVCLKEYQAKVTPTGP
CSYGHGATPVLGGNSFYLPPAGAAGDRARARARAGGDQDPGLVVIPFQFAWPRSFTLIVEAWDW
DNDTTPNEELLIERVSHAGMINPEDRWKSLHFSGHVAHLELQIRVRCDENYYSATCNKFCRPRN
DFFGHYTCDQYGNKACMDGWMGKECKEAVCKQGCNLLHGGCTVPGECRCSYGWQGRFCDECVPY
PGCVHGSCVEPWQCNCETNWGGLLCDKDLNYCGSHHPCTNGGTCINAEPDQYRCTCPDGYSGRN
CEKAEHACTSNPCANGGSCHEVPSGFECHCPSGWSGPTCALDIDEEFGLVPRGSGHHHHHH
(SEQ ID NO. 8)

| Kabat# | 81 | 82 | 83 | 84 | 85 | 86 | 87 | 88 | 89 | 90 | 91 | 92 | 93 | 94 | 95 | 96 | 97 | 98 | 99 | 100 | 101 | 102 | 103 | 104 | 105 | 106 | 107 | |
|---|---|---|---|---|---|---|---|---|---|---|---|---|---|---|---|---|---|---|---|---|---|---|---|---|---|---|---|---|
| | | | | | | | | | Kabat – CDR L3 | | | | | | | | | | | | | | | | | | | |
| | | | | | | | | | Chothia – CDR L3 | | | | | | | | | | | | | | | | | | | |
| | | | | | | | | | Contact – CDR L3 | | | | | | | | | | | | | | | | | | | |
| C    | E | D | F | A | T | Y | Y | C | Q | Q | S | Y | T | T | P | P | T | F | G | Q | G | T | K | V | E | I | K | SEQ ID NO: 25 |
| C-1  | E | D | F | A | T | Y | Y | C | Q | Q | S | Y | T | S | P | P | T | F | G | Q | G | T | K | V | E | I | K | SEQ ID NO: 26 |
| D    | E | D | F | A | T | Y | Y | C | Q | Q | Y | Y | L | T | P | P | T | F | G | Q | G | T | K | V | E | I | K | SEQ ID NO: 27 |
| D-1  | E | D | F | A | T | Y | Y | C | Q | Q | Y | L | H | T | P | P | T | F | G | Q | G | T | K | V | E | I | K | SEQ ID NO: 28 |
| A    | E | D | F | A | T | Y | Y | C | Q | Q | Y | Y | S | T | P | P | T | F | G | Q | G | T | K | V | E | I | K | SEQ ID NO: 18 |
| A-1  | E | D | F | A | T | Y | Y | C | Q | Q | S | G | S | T | P | A | T | F | G | Q | G | T | K | V | E | I | K | SEQ ID NO: 19 |
| A-2  | E | D | F | A | T | Y | Y | C | Q | Q | S | G | S | T | P | P | T | F | G | Q | G | T | K | V | E | I | K | SEQ ID NO: 20 |
| B    | E | D | F | A | T | Y | Y | C | Q | Q | S | W | T | T | P | A | T | F | G | Q | G | T | K | V | E | I | K | SEQ ID NO: 21 |
| B-1  | E | D | F | A | T | Y | Y | C | Q | Q | Y | F | G | S | P | P | T | F | G | Q | G | T | K | V | E | I | K | SEQ ID NO: 22 |
| B-2  | E | D | F | A | T | Y | Y | C | Q | Q | Y | S | H | S | P | L | T | F | G | Q | G | T | K | V | E | I | K | SEQ ID NO: 23 |
| B-3  | E | D | F | A | T | Y | Y | C | Q | Q | Y | G | S | S | P | P | T | F | G | Q | G | T | K | V | E | I | K | SEQ ID NO: 24 |
| D-2  | E | D | F | A | T | Y | Y | C | Q | Q | Y | Y | S | S | P | L | T | F | G | Q | G | T | K | V | E | I | K | SEQ ID NO: 77 |
| D-3  | E | D | F | A | T | Y | Y | C | Q | Q | Y | S | S | S | P | L | T | F | G | Q | G | T | K | V | E | I | K | SEQ ID NO: 78 |
| D-4  | E | D | F | A | T | Y | Y | C | Q | Q | Y | Y | S | S | P | L | T | F | G | Q | G | T | K | V | E | I | K | SEQ ID NO: 79 |
| D-5  | E | D | F | A | T | Y | Y | C | Q | Q | Y | S | S | S | P | L | T | F | G | Q | G | T | K | V | E | I | K | SEQ ID NO: 80 |

|   | FR1 | | FR2 | |
|---|---|---|---|---|
| I |  |  |  |  |
| A | QVQLVQSGAEVKKPGASVKVSCKASGYTFT | -H1- | WVRQAPGQGLEWMG | -H2- RVT |
| B | QVQLVQSGAEVKKPGASVKVSCKAS | -H1- | WVRQAPGQGLEWM | -H2- RVT |
| C | QVQLVQSGAEVKKPGASVKVSCKAS | -H1- | WVRQAPGQGLEWM | -H2- RVT |
| D | QVQLVQSGAEVKKPGASVKVSCKAS | -H1- | WVRQAPGQGLEWM | -H2- RVT |
| II |  |  |  |  |
| A | QVQLQESGPGLVKPSQTLSLTCTVSGGSVS | -H1- | WIRQPPGKGLEWIG | -H2- RVT |
| B | QVQLQESGPGLVKPSQTLSLTCTVS | -H1- | WIRQPPGKGLEWI | -H2- RVT |
| C | QVQLQESGPGLVKPSQTLSLTCTVS | -H1- | WIRQPPGKGLEWI | -H2- RVT |
| D | QVQLQESGPGLVKPSQTLSLTCTVS | -H1- | WIRQPPGKGLEWI | -H2- RVT |
| III |  |  |  |  |
| A | EVQLVESGGGLVQPGGSLRLSCAASGFTFS | -H1- | WVRQAPGKGLEWVS | -H2- RFT |
| B | EVQLVESGGGLVQPGGSLRLSCAAS | -H1- | WVRQAPGKGLEWV | -H2- RFT |
| C | EVQLVESGGGLVQPGGSLRLSCAAS | -H1- | WVRQAPGKGLEWV | -H2- RFT |
| D | EVQLVESGGGLVQPGGSLRLSCAAS | -H1- | WVRQAPGKGLEWV | -H2- RFT |
| Acceptor-1 |  |  |  |  |
| A | EVQLVESGGGLVQPGGSLRLSCAASGFNIK | -H1- | WVRQAPGKGLEWV | -H2- RFT |
| B | EVQLVESGGGLVQPGGSLRLSCAAS | -H1- | WVRQAPGKGLEWV | -H2- RFT |
| C | EVQLVESGGGLVQPGGSLRLSCAAS | -H1- | WVRQAPGKGLEWV | -H2- RFT |
| Acceptor-2 |  |  |  |  |
| A | EVQLVESGGGLVQPGGSLRLSCAASGFNIK | -H1- | WVRQAPGKGLEWV | -H2- RFT |
| B | EVQLVESGGGLVQPGGSLRLSCAAS | -H1- | WVRQAPGKGLEWV | -H2- RFT |
| C | EVQLVESGGGLVQPGGSLRLSCAAS | -H1- | WVRQAPGKGLEWV | -H2- RFT |
| D | EVQLVESGGGLVQPGGSLRLSCAAS | -H1- | WVRQAPGKGLEWV | -H2- RFT |

*FIG. 5A*

| | FR3 | FR4 | SEQ ID NOs of FR1, FR2, FR3, FR4 |
|---|---|---|---|
| I A | ITADTSTSTAYMELSSLRSEDTAVYYCAR -H3- | WGQGTLVTVSS | SEQ ID NO.: 32, 33, 34, 35 |
| B | ITADTSTSTAYMELSSLRSEDTAVYYCAR -H3- | WGQGTLVTVSS | SEQ ID NO.: 36, 37, 34, 35 |
| C | ITADTSTSTAYMELSSLRSEDTAVYYCA -H3- | WGQGTLVTVSS | SEQ ID NO.: 36, 37, 38, 35 |
| D | ITADTSTSTAYMELSSLRSEDTAVYYC -H3- | WGQGTLVTVSS | SEQ ID NO.: 36, 37, 39, 35 |
| II A | ISVDTSKNQFSLKLSSVTAADTAVYYCAR -H3- | WGQGTLVTVSS | SEQ ID NO.: 40, 41, 42, 35 |
| B | ISVDTSKNQFSLKLSSVTAADTAVYYCAR -H3- | WGQGTLVTVSS | SEQ ID NO.: 43, 44, 42, 35 |
| C | ISVDTSKNQFSLKLSSVTAADTAVYYCA -H3- | WGQGTLVTVSS | SEQ ID NO.: 43, 44, 45, 35 |
| D | ISVDTSKNQFSLKLSSVTAADTAVYYC -H3- | WGQGTLVTVSS | SEQ ID NO.: 43, 44, 46, 35 |
| III A | ISRDNSKNTLYLQMNSLRAEDTAVYYCAR -H3- | WGQGTLVTVSS | SEQ ID NO.: 47, 48, 49, 35 |
| B | ISRDNSKNTLYLQMNSLRAEDTAVYYCAR -H3- | WGQGTLVTVSS | SEQ ID NO.: 50, 51, 49, 35 |
| C | ISRDNSKNTLYLQMNSLRAEDTAVYYCA -H3- | WGQGTLVTVSS | SEQ ID NO.: 50, 51, 52, 35 |
| D | ISRDNSKNTLYLQMNSLRAEDTAVYYC -H3- | WGQGTLVTVSS | SEQ ID NO.: 50, 51, 53, 35 |
| Acceptor-1 A | ISADTSKNTAYLQMNSLRAEDTAVYYCSR -H3- | WGQGTLVTVSS | SEQ ID NO.: 54, 48, 55, 35 |
| B | ISADTSKNTAYLQMNSLRAEDTAVYYCSR -H3- | WGQGTLVTVSS | SEQ ID NO.: 50, 51, 55, 35 |
| C | ISADTSKNTAYLQMNSLRAEDTAVYYC -H3- | WGQGTLVTVSS | SEQ ID NO.: 50, 51, 56, 35 |
| Acceptor-2 A | ISADTSKNTAYLQMNSLRAEDTAVYYCAR -H3- | WGQGTLVTVSS | SEQ ID NO.: 54, 48, 57, 35 |
| B | ISADTSKNTAYLQMNSLRAEDTAVYYCAR -H3- | WGQGTLVTVSS | SEQ ID NO.: 50, 51, 57, 35 |
| C | ISADTSKNTAYLQMNSLRAEDTAVYYCA -H3- | WGQGTLVTVSS | SEQ ID NO.: 50, 51, 58, 35 |
| D | ISADTSKNTAYLQMNSLRAEDTAVYYC -H3- | WGQGTLVTVSS | SEQ ID NO.: 50, 51, 59, 35 |

FIG. 5B

HVR-H1 Sequences - Antibody A and Affinity Matured Antibodies Derived from Antibody A

| Antibody # | SEQ ID NO: | Kabat Number | | | | | | | | | |
|---|---|---|---|---|---|---|---|---|---|---|---|
| | | 26 | 27 | 28 | 29 | 30 | 31 | 32 | 33 | 34 | 35 |
| A, A-1, A-2 | 81 | G | F | T | F | S | N | Y | G | I | H |

HVR-H2 Sequence - Antibody A and Affinity Matured Antibodies Derived from Antibody A

| Antibody # | SEQ ID NO: | Kabat Number | | | | | | | | | | | | | | | |
|---|---|---|---|---|---|---|---|---|---|---|---|---|---|---|---|---|---|
| | | 50 | 51 | 52 | 52A | 53 | 54 | 55 | 56 | 57 | 58 | 59 | 60 | 61 | 62 | 63 | 64 | 65 |
| A, A-1 | 82 | W | I | T | P | D | G | G | Y | T | D | Y | A | D | S | V | K | G |
| A-2 | 83 | W | I | T | G | N | G | G | Y | S | D | Y | A | D | S | V | K | G |
| consensus | 84 | W | I | T | P/G | D/N | G | G | Y | T/S | D | Y | A | D | S | V | K | G |

*FIG. 7A*

HVR-H3 Sequence - Antibody A and Affinity Matured Antibodies Derived from Antibody A

| Antibody # | SEQ ID NO: | Kabat Number |||||||||
|---|---|---|---|---|---|---|---|---|---|---|
| | | 95 | 96 | 97 | 98 | 100k | 101 | 102 |
| A, A-2 | 85 | A | G | S | W | F | A | Y |
| A-1 | 86 | A | G | S | L | F | A | Y |
| consensus | 87 | A | G | S | W/L | F | A | Y |

HVR-H1 Sequences - Antibody B and Affinity Matured Antibodies Derived from Antibody B

| Antibody # | SEQ ID NO: | Kabat Number ||||||||||
|---|---|---|---|---|---|---|---|---|---|---|---|
| | | 26 | 27 | 28 | 29 | 30 | 31 | 32 | 33 | 34 | 35 |
| B, B-1, B-2, B-3, B-4 | 88 | G | F | T | F | T | S | Y | D | I | H |

FIG. 7B

HVR-H3 Sequence - Antibody B and Affinity Matured Antibodies Derived from Antibody B

| Antibody # | SEQ ID NO: | | | | | | | | | | | | | | | Kabat Number | | | | |
|---|---|---|---|---|---|---|---|---|---|---|---|---|---|---|---|---|---|---|---|---|
| | | 50 | 51 | 52 | 52A | 53 | 54 | 55 | 56 | 57 | 58 | 59 | 60 | 61 | 62 | 63 | 64 | 65 | | |
| B, B-1, B-2, B-3, B-4 | 89 | G | I | S | P | A | D | G | D | T | D | Y | A | N | S | V | K | G | | |

HVR-H3 Sequence - Antibody B and Affinity Matured Antibodies Derived from Antibody B

| Antibody # | SEQ ID NO: | Kabat Number | | | | | | | | | | | | | |
|---|---|---|---|---|---|---|---|---|---|---|---|---|---|---|---|
| | | 95 | 96 | 97 | 98 | 99 | 100 | 100A | 100B | 100C | 100D | 100E | 100K | 101 | 102 |
| B, B2 | 90 | N | D | Y | D | V | R | S | V | G | S | G | M | D | Y |
| B-1 | 91 | N | D | Y | D | V | R | T | V | G | S | G | M | D | Y |
| B-3 | 92 | N | D | Y | D | V | R | F | V | G | S | G | M | D | Y |
| B-4 | 93 | N | D | Y | D | V | R | Y | F | G | S | G | M | D | Y |
| consensus | 94 | N | D | Y | D | V | R | S/T/F/Y | V/F | G | S | G | M | D | Y |

FIG. 7C

HVR-H1 Sequence - Antibody C and Affinity Matured Antibodies Derived from Antibody C

| Antibody # | SEQ ID NO: | Kabat Number | | | | | | | | | |
|---|---|---|---|---|---|---|---|---|---|---|---|
| | | 26 | 27 | 28 | 29 | 30 | 31 | 32 | 33 | 34 | 35 |
| C, C-1 | 95 | G | F | T | F | T | N | S | D | I | H |

HVR-H2 Sequence - Antibody C and Affinity Matured Antibodies Derived from Antibody C

| Antibody # | SEQ ID NO: | Kabat Number | | | | | | | | | | | | | | | |
|---|---|---|---|---|---|---|---|---|---|---|---|---|---|---|---|---|---|
| | | 50 | 51 | 52 | 52A | 53 | 54 | 55 | 56 | 57 | 58 | 59 | 60 | 61 | 62 | 63 | 64 | 65 |
| C, C-1 | 96 | G | F | T | F | A | D | G | Y | T | D | Y | A | D | S | V | K | G |

HVR-H3 Sequence - Antibody C and Affinity Matured Antibodies Derived from Antibody C

| Antibody # | SEQ ID NO: | Kabat Number | | | | | | | | | | | | |
|---|---|---|---|---|---|---|---|---|---|---|---|---|---|---|
| | | 95 | 96 | 97 | 98 | 99 | 100 | 100A | 100B | 100C | 100D | 100K | 101 | 102 |
| C | 97 | S | Y | W | N | N | S | P | G | S | G | F | D | Y |
| C-1 | 98 | S | Y | W | S | S | S | P | G | S | A | F | D | Y |
| consensus | 99 | S | Y | W | N/S | N/S | S | P | G | S | G/A | F | D | Y |

FIG. 7D

HVR-H1 Sequences - Antibody D and Affinity Matured Antibodies Derived from Antibody D

| Antibody # | SEQ ID NO: | Kabat Number | | | | | | | | | |
|---|---|---|---|---|---|---|---|---|---|---|---|
| | | 26 | 27 | 28 | 29 | 30 | 31 | 32 | 33 | 34 | 35 |
| D, D-1 | 100 | G | F | T | F | T | S | N | Y | M | S |
| D-2 | 101 | G | F | S | V | K | P | M | Y | M | T |
| D-3 | 102 | G | F | T | F | I | S | N | Y | V | S |
| D-4 | 103 | G | F | T | V | T | P | L | Y | M | S |
| D-5 | 104 | G | F | T | V | T | P | M | Y | M | S |
| Consensus | 105 | G | F | T/S | F/V | T/K I/T | S/P | N/M/ L | Y | M/V | S/T |

HVR-H2 Sequences - Antibody D and Affinity Matured Antibodies Derived from Antibody D

| Antibody # | SEQ ID NO: | Kabat Number | | | | | | | | | | | | | | | |
|---|---|---|---|---|---|---|---|---|---|---|---|---|---|---|---|---|---|
| | | 50 | 51 | 52 | 52A | 53 | 54 | 55 | 56 | 57 | 58 | 59 | 60 | 61 | 62 | 63 | 64 | 65 |
| D, D-1, D-2, D-3, D-4, D-5 | 106 | T | I | W | Y | Q | S | G | T | T | D | Y | A | D | S | V | K | G |

*FIG. 7E*

HVR-H3 Sequence - Antibody D and Affinity Matured Antibodies Derived from Antibody D

| Antibody # | SEQ ID NO: | Kabat Number | | | | | | | | | | | | | |
|---|---|---|---|---|---|---|---|---|---|---|---|---|---|---|---|
| | | 95 | 96 | 97 | 98 | 99 | 100 | 100A | 100B | 100C | 100D | 100K | 101 | 102 |
| D, D-2, D-3, D-4, D-5 | 107 | S | S | P | W | S | G | E | G | F | G | M | D | V |
| D-1 | 108 | D | S | P | W | P | S | K | G | F | G | M | D | V |
| consensus | 109 | S/D | S | P | W | S/P | G/S | E/K | G | F | G | M | D | V |

*FIG. 7F*

HVR-L1 Sequences - Antibody A and Affinity Matured Antibodies Derived from Antibody A

| Antibody # | SEQ ID NO: | Kabat Number |  |  |  |  |  |  |  |  |  |
|---|---|---|---|---|---|---|---|---|---|---|---|
|  |  | 24 | 25 | 26 | 27 | 28 | 29 | 30 | 31 | 32 | 33 | 34 |
| A, A-1, A-2 | 110 | R | A | S | Q | D | V | S | T | A | V | A |

HVR-L2 Sequences - Antibody A and Affinity Matured Antibodies Derived from Antibody A

| Antibody # | SEQ ID NO: | Kabat Number |  |  |  |  |  |  |
|---|---|---|---|---|---|---|---|---|
|  |  | 50 | 51 | 52 | 53 | 54 | 55 | 56 |
| A, A-1, A-2 | 111 | S | A | S | F | L | Y | S |

HVR-L3 Sequences - Antibody A and Affinity Matured Antibodies Derived from Antibody A

| Clone # | SEQ ID NO: | Kabat Number |  |  |  |  |  |  |  |  |
|---|---|---|---|---|---|---|---|---|---|---|
|  |  | 89 | 90 | 91 | 92 | 93 | 94 | 95 | 96 | 97 |
| A, A-2 | 112 | Q | Q | S | Y | T | T | P | P | T |
| A-1 | 113 | Q | Q | Y | Y | T | T | A | T | T |
| consensus | 114 | Q | Q | S/Y | Y | T | T | P/A | P/T | T |

*FIG. 8A*

HVR-L1 Sequences - Antibody B and Affinity Matured Antibodies Derived from Antibody B

| Antibody # | SEQ ID NO: | Kabat Number | | | | | | | | | |
|---|---|---|---|---|---|---|---|---|---|---|---|
| | | 24 | 25 | 26 | 27 | 28 | 29 | 30 | 31 | 32 | 33 | 34 |
| B, B-1, B-2, B-3, B-4 | 115 | R | A | S | Q | D | V | S | T | A | V | A |

HVR-L2 Sequences - Antibody B and Affinity Matured Antibodies Derived from Antibody B

| Antibody # | SEQ ID NO: | Kabat Number | | | | | | |
|---|---|---|---|---|---|---|---|---|
| | | 50 | 51 | 52 | 53 | 54 | 55 | 56 |
| B, B-1, B-2, B-3, B-4 | 116 | S | A | S | F | L | Y | S |

*FIG. 8B*

HVR-L3 Sequences - Antibody B and Affinity Matured Antibodies Derived from Antibody B

| Clone # | SEQ ID NO: | Kabat Number | | | | | | | | |
|---|---|---|---|---|---|---|---|---|---|---|
| | | 89 | 90 | 91 | 92 | 93 | 94 | 95 | 96 | 97 |
| B | 117 | Q | Q | S | Y | T | T | P | P | T |
| B-1 | 118 | Q | Q | S | Y | T | S | A | P | T |
| B-2 | 119 | Q | Q | S | W | T | A | P | P | T |
| B-3 | 120 | Q | Q | S | F | T | A | P | P | T |
| B-4 | 121 | Q | Q | S | Y | I | S | P | P | T |
| Consensus | 122 | Q | Q | S | Y/W/F | T/I | T/S/A | P/A | P | T |

HVR-L1 Sequences - Antibody C and Affinity Matured Antibodies Derived from Antibody C

| Antibody # | SEQ ID NO: | Kabat Number | | | | | | | | | | |
|---|---|---|---|---|---|---|---|---|---|---|---|---|
| | | 24 | 25 | 26 | 27 | 28 | 29 | 30 | 31 | 32 | 33 | 34 |
| C, C-1 | 123 | R | A | S | Q | D | V | S | T | A | V | A |

*FIG. 8C*

HVR-L2 Sequences - Antibody C and Affinity Matured Antibodies Derived from Antibody C

| Antibody # | SEQ ID NO: | Kabat Number | | | | | | |
|---|---|---|---|---|---|---|---|---|
| | | 50 | 51 | 52 | 53 | 54 | 55 | 56 |
| C, C-1 | 124 | S | A | S | F | L | Y | S |

HVR-L3 Sequences - Antibody C and Affinity Matured Antibodies Derived from Antibody C

| Clone # | SEQ ID NO: | Kabat Number | | | | | | | | | |
|---|---|---|---|---|---|---|---|---|---|---|---|
| | | 89 | 90 | 91 | 92 | 93 | 94 | 95 | 96 | 97 |
| C | 125 | Q | Q | S | Y | T | T | P | P | T |
| C-1 | 126 | Q | Q | S | Y | I | S | P | S | T |
| consensus | 127 | Q | Q | S | Y | T/I | T/S | P | P/S | T |

HVR-L1 Sequences - Antibody D and Affinity Matured Antibodies Derived from Antibody D

| Antibody # | SEQ ID NO: | Kabat Number | | | | | | | | | | |
|---|---|---|---|---|---|---|---|---|---|---|---|---|
| | | 24 | 25 | 26 | 27 | 28 | 29 | 30 | 31 | 32 | 33 | 34 |
| D, D-1, D-2, D-3, D-4, D-5 | 128 | R | A | S | Q | S | I | S | S | Y | L | A |

FIG. 8D

HVR-L2 Sequences - Antibody D and Affinity Matured Antibodies Derived from Antibody D

| Antibody # | SEQ ID NO: | Kabat Number | |

*Framework sequences of Antibodies A, A-1, A-2, B, B-1, B-2, B-3, C, C-1, D, D-1, D-2, D-3, D-4 and D-5 light chain variable domain*

LC-FR1   $^1$Asp Ile Gln Met Thr Gln Ser Pro Ser Ser Leu Ser Ala Ser Val Gly Asp Arg Val Thr Ile Thr Cys$^{23}$ (SEQ ID NO:60)

LC-FR2   $^{35}$Trp Tyr Gln Gln Lys Pro Gly Lys Ala Pro Lys Leu Leu Ile Tyr$^{49}$ (SEQ ID NO:61)

LC-FR3   $^{57}$Gly Val Pro Ser Arg Phe Ser Gly Ser Gly Ser Gly Thr Asp Phe Thr Leu Thr Ile Ser Ser Leu Gln Pro Glu Asp Phe Ala Thr Tyr Tyr Cys$^{88}$ (SEQ ID NO:62)

LC-FR4   $^{98}$Phe Gly Gln Gly Thr Lys Val Glu Ile Lys Arg$^{108}$ (SEQ ID NO:135)

*Framework sequences of Antibody A, A-1, A-2, B, B-1, B-2, B-3, C, and C-1 heavy chain variable domain*

HC-FR1   $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO:50)

HC-FR2   $^{36}$Trp Val Arg Gln Ala Pro Gly Lys Gly Leu Glu Trp Val Gly$^{49}$ (SEQ ID NO:136)

HC-FR3   $^{66}$Arg Phe Thr Ile Ser Ala Asp Thr Ser Lys Asn Thr Ala Tyr Leu Gln Met Asn Ser Leu Arg Ala Glu Asp Thr Ala Val Tyr Tyr Cys Ala Arg$^{94}$ (SEQ ID NO:57)

HC-FR4   $^{103}$Trp Gly Gln Gly Thr Leu Val Thr Val Ser Ser$^{113}$ (SEQ ID NO:35)

*Framework sequences of Antibody D, D-1, D-2, D-3, D-4 and D-5 heavy chain variable domain*

HC-FR1   $^1$Glu Val Gln Leu Val Glu Ser Gly Gly Gly Leu Val Gln Pro Gly Gly Ser Leu Arg Leu Ser Cys Ala Ala Ser$^{25}$ (SEQ ID NO:50)

HC-FR2   $^{36}$Trp Val Arg Gln Ala Pro Gly Lys Gly Leu Glu Trp Val Ser$^{49}$ (SEQ ID NO:48)

HC-FR3   $^{66}$Arg Phe Thr Ile Ser Ala Asp Thr Ser Lys Asn Thr Ala Tyr Leu Gln Met Asn Ser Leu Arg Ala Glu Asp Thr Ala Val Tyr Tyr Cys Ala Arg$^{94}$ (SEQ ID NO:57)

HC-FR4   $^{103}$Trp Gly Gln Gly Thr Leu Val Thr Val Ser Ser$^{113}$ (SEQ ID NO:35)

*FIG. 9*

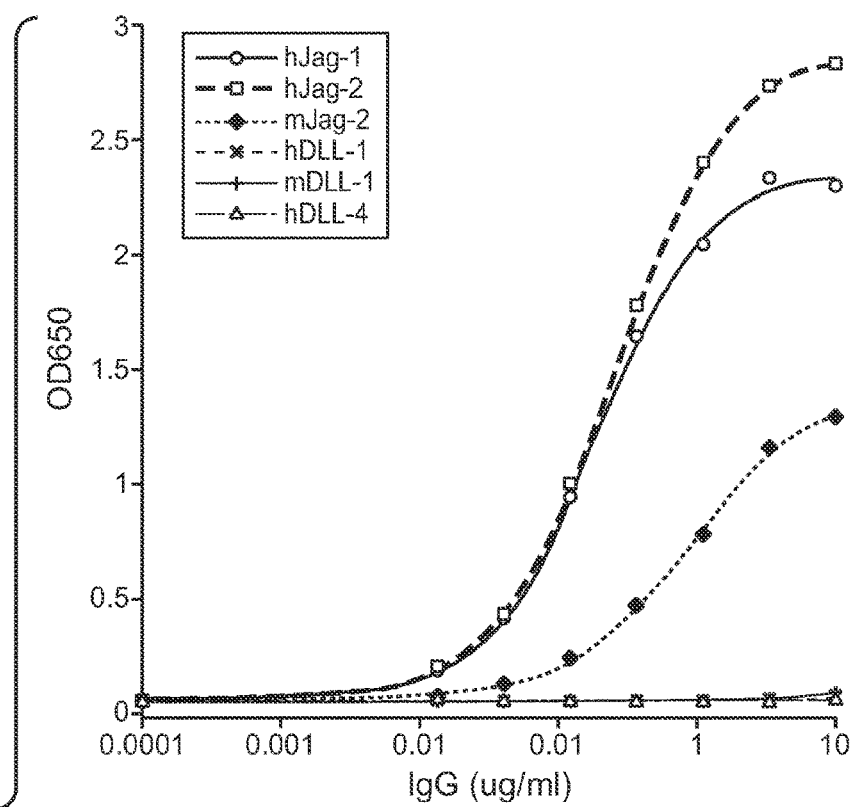
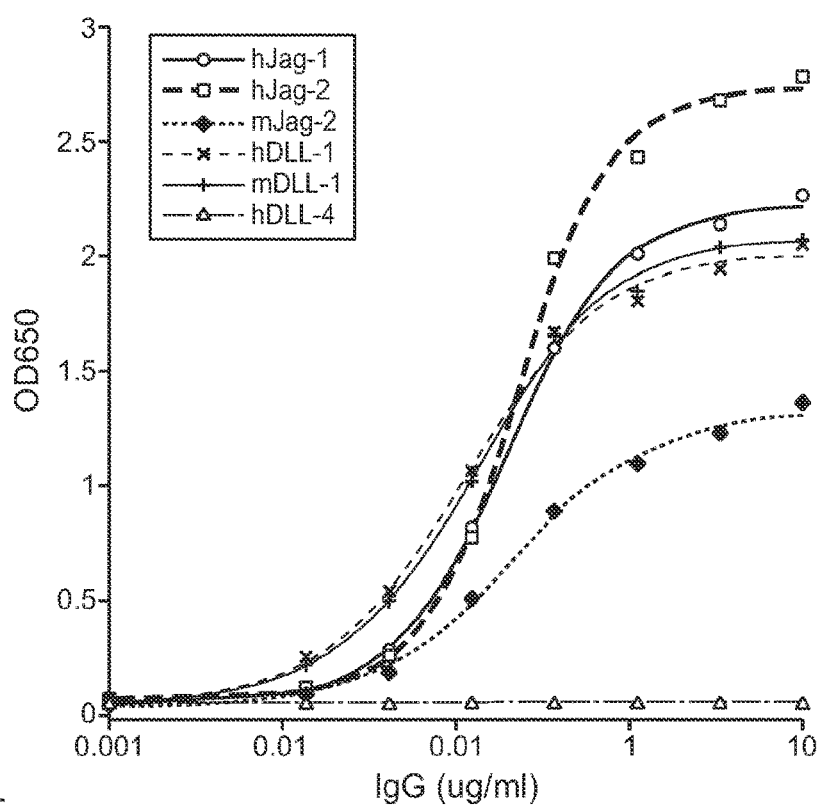
FIG. 10A

| Biacore Summary Table | | | | | | | | | | |
|---|---|---|---|---|---|---|---|---|---|---|
| | Human Jag1 | | | Human Jag2 | | | Mouse Jag2 | | | |
| Clone (hIgG1) | kon/(1/Ms) | koff/(1/s) | Kd(M) | kon/(1/Ms) | koff/(1/s) | Kd(M) | kon/(1/Ms) | koff/(1/s) | Kd(M) | |
| C | 2.7E+05 | 6.2E-04 | 2.3E-09 | n.d | n.d | n.d | n.d | n.d | n.d | |
| C-1 | 2.9E+05 | 9.0E-05 | 3.1E-10 | 8.9E+05 | 1.1E+04 | 1.2E-10 | 7.4E+05 | 5.40E-04 | 7.3E-10 | |
| D | 1.8E+05 | 2.3E-03 | 1.3E-08 | n.d. | n.d. | n.d. | n.d | n.d | n.d | |
| D-2 | 1.2E+05 | 1.3E-04 | 1.1E-09 | n.d. | n.d. | n.d. | n.d | n.d | n.d | |
| D-1 | 8.1E+04 | 4.2E-05 | 5.2E-10 | 5.7E+04 | 2.7E+04 | 4.6E-09 | 6.2E+04 | 8.50E-04 | 1.4E-08 | |
| A | 2.3E+04 | 2.1E-03 | 9.4E-08 | No Binding up to 0.5 µM | | | | | | |
| A-1 | 8.3E+04 | 5.9E-05 | 7.1E-10 | | | | | | | |
| A-2 | 2.3E+05 | 7.1E-05 | 3.0E-10 | | | | | | | |
| B | No Binding up to 0.5 µM | | | 2.5E+06 | 2.6E-03 | 1.0E-09 | 2.5E+06 | 2.6E-03 | 1.0E-09 | |
| B-1 | | | | | | | 8.5E+05 | 1.61E-03 | 1.1E-09 | |
| B-2 | | | | | | | 1.3E+06 | 3.23E-06 | 2.5E-12 | |
| B-4 | | | | | | | 6.6E+05 | 3.25E-04 | 4.9E-10 | |
| B-3 | | | | | | | 5.8E+05 | 1.75E-04 | 3.0E-10 | |

FIG. 11

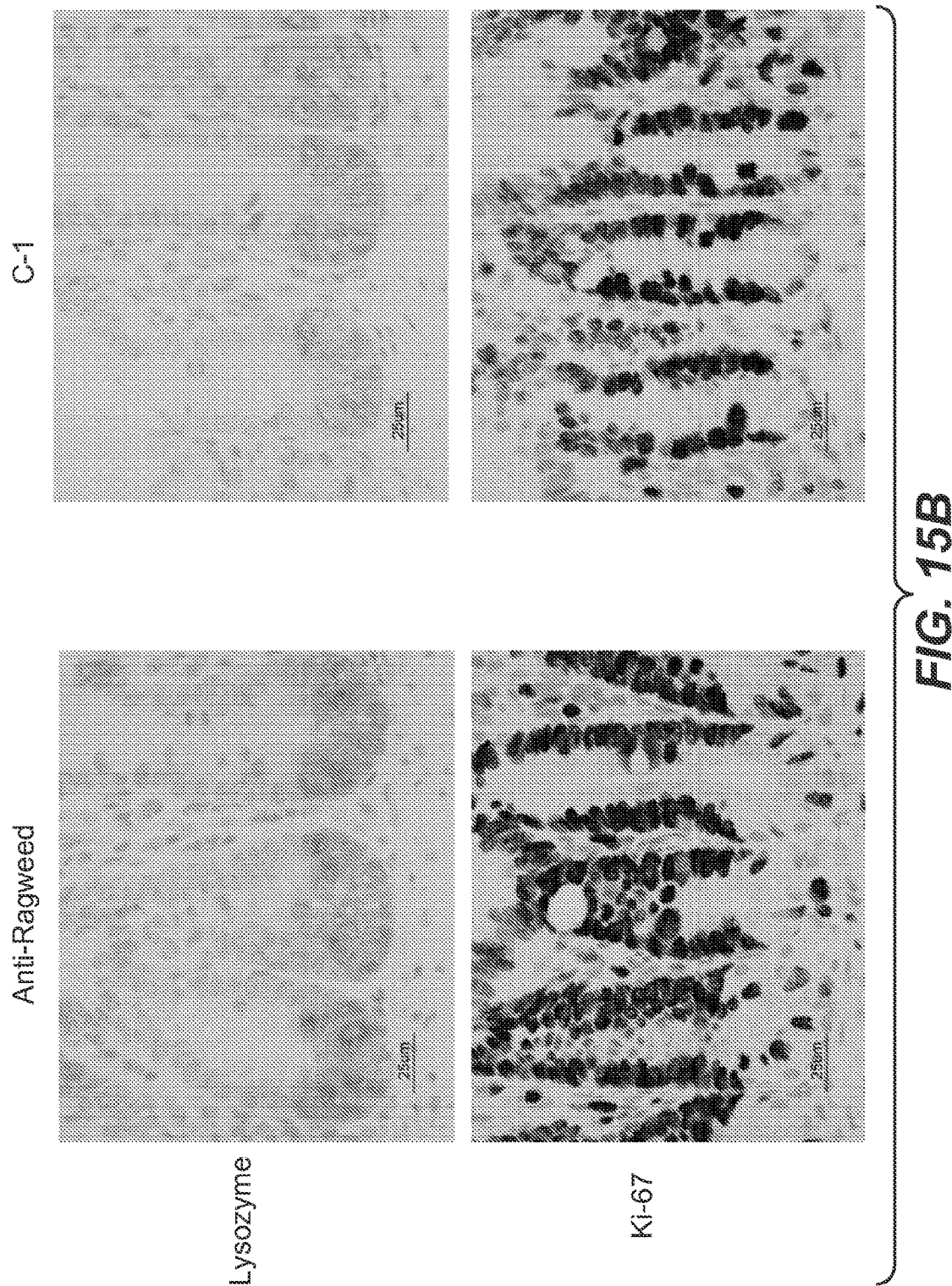

SEQUENCE LISTING

```
<160> NUMBER OF SEQ ID NOS: 138

<210> SEQ ID NO 1
<211> LENGTH: 1218
<212> TYPE: PRT
<213> ORGANISM: Homo sapiens

<400> SEQUENCE: 1

Met Arg Ser Pro Arg Thr Arg Gly Arg Ser Gly Arg Pro Leu Ser Leu
1               5                   10                  15

Leu Leu Ala Leu Leu Cys Ala Leu Arg Ala Lys Val Cys Gly Ala Ser
            20                  25                  30

Gly Gln Phe Glu Leu Glu Ile Leu Ser Met Gln Asn Val Asn Gly Glu
        35                  40                  45

Leu Gln Asn Gly Asn Cys Cys Gly Gly Ala Arg Asn Pro Gly Asp Arg
    50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Val Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Val
                165                 170                 175

Ala His Phe Glu Tyr Gln Ile Arg Val Thr Cys Asp Asp Tyr Tyr Tyr
            180                 185                 190

Gly Phe Gly Cys Asn Lys Phe Cys Arg Pro Arg Asp Asp Phe Phe Gly
```

```
            195                 200                 205
His Tyr Ala Cys Asp Gln Asn Gly Asn Lys Thr Cys Met Glu Gly Trp
    210                 215                 220
Met Gly Pro Glu Cys Asn Arg Ala Ile Cys Arg Gln Gly Cys Ser Pro
225                 230                 235                 240
Lys His Gly Ser Cys Lys Leu Pro Gly Asp Cys Arg Cys Gln Tyr Gly
                245                 250                 255
Trp Gln Gly Leu Tyr Cys Asp Lys Cys Ile Pro His Pro Gly Cys Val
            260                 265                 270
His Gly Ile Cys Asn Glu Pro Trp Gln Cys Leu Cys Glu Thr Asn Trp
        275                 280                 285
Gly Gly Gln Leu Cys Asp Lys Asp Leu Asn Tyr Cys Gly Thr His Gln
    290                 295                 300
Pro Cys Leu Asn Gly Gly Thr Cys Ser Asn Thr Gly Pro Asp Lys Tyr
305                 310                 315                 320
Gln Cys Ser Cys Pro Glu Gly Tyr Ser Gly Pro Asn Cys Glu Ile Ala
                325                 330                 335
Glu His Ala Cys Leu Ser Asp Pro Cys His Asn Arg Gly Ser Cys Lys
            340                 345                 350
Glu Thr Ser Leu Gly Phe Glu Cys Glu Cys Ser Pro Gly Trp Thr Gly
        355                 360                 365
Pro Thr Cys Ser Thr Asn Ile Asp Asp Cys Ser Pro Asn Asn Cys Ser
    370                 375                 380
His Gly Gly Thr Cys Gln Asp Leu Val Asn Gly Phe Lys Cys Val Cys
385                 390                 395                 400
Pro Pro Gln Trp Thr Gly Lys Thr Cys Gln Leu Asp Ala Asn Glu Cys
                405                 410                 415
Glu Ala Lys Pro Cys Val Asn Ala Lys Ser Cys Lys Asn Leu Ile Ala
            420                 425                 430
Ser Tyr Tyr Cys Asp Cys Leu Pro Gly Trp Met Gly Gln Asn Cys Asp
        435                 440                 445
Ile Asn Ile Asn Asp Cys Leu Gly Gln Cys Gln Asn Asp Ala Ser Cys
    450                 455                 460
Arg Asp Leu Val Asn Gly Tyr Arg Cys Ile Cys Pro Pro Gly Tyr Ala
465                 470                 475                 480
Gly Asp His Cys Glu Arg Asp Ile Asp Glu Cys Ala Ser Asn Pro Cys
                485                 490                 495
Leu Asn Gly Gly His Cys Gln Asn Glu Ile Asn Arg Phe Gln Cys Leu
            500                 505                 510
Cys Pro Thr Gly Phe Ser Gly Asn Leu Cys Gln Leu Asp Ile Asp Tyr
        515                 520                 525
Cys Glu Pro Asn Pro Cys Gln Asn Gly Ala Gln Cys Tyr Asn Arg Ala
    530                 535                 540
Ser Asp Tyr Phe Cys Lys Cys Pro Glu Asp Tyr Glu Gly Lys Asn Cys
545                 550                 555                 560
Ser His Leu Lys Asp His Cys Arg Thr Thr Pro Cys Glu Val Ile Asp
                565                 570                 575
Ser Cys Thr Val Ala Met Ala Ser Asn Asp Thr Pro Glu Gly Val Arg
            580                 585                 590
Tyr Ile Ser Ser Asn Val Cys Gly Pro His Gly Lys Cys Lys Ser Gln
        595                 600                 605
Ser Gly Gly Lys Phe Thr Cys Asp Cys Asn Lys Gly Phe Thr Gly Thr
    610                 615                 620
```

-continued

```
Tyr Cys His Glu Asn Ile Asn Asp Cys Glu Ser Asn Pro Cys Arg Asn
625                 630                 635                 640

Gly Gly Thr Cys Ile Asp Gly Val Asn Ser Tyr Lys Cys Ile Cys Ser
                645                 650                 655

Asp Gly Trp Glu Gly Ala Tyr Cys Glu Thr Asn Ile Asn Asp Cys Ser
                660                 665                 670

Gln Asn Pro Cys His Asn Gly Gly Thr Cys Arg Asp Leu Val Asn Asp
            675                 680                 685

Phe Tyr Cys Asp Cys Lys Asn Gly Trp Lys Gly Lys Thr Cys His Ser
        690                 695                 700

Arg Asp Ser Gln Cys Asp Glu Ala Thr Cys Asn Asn Gly Gly Thr Cys
705                 710                 715                 720

Tyr Asp Glu Gly Asp Ala Phe Lys Cys Met Cys Pro Gly Gly Trp Glu
                725                 730                 735

Gly Thr Thr Cys Asn Ile Ala Arg Asn Ser Ser Cys Leu Pro Asn Pro
                740                 745                 750

Cys His Asn Gly Gly Thr Cys Val Val Asn Gly Glu Ser Phe Thr Cys
            755                 760                 765

Val Cys Lys Glu Gly Trp Glu Gly Pro Ile Cys Ala Gln Asn Thr Asn
770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                805                 810                 815

Cys Arg Ile Asn Ile Asn Glu Cys Gln Ser Ser Pro Cys Ala Phe Gly
                820                 825                 830

Ala Thr Cys Val Asp Glu Ile Asn Gly Tyr Arg Cys Val Cys Pro Pro
            835                 840                 845

Gly His Ser Gly Ala Lys Cys Gln Glu Val Ser Gly Arg Pro Cys Ile
        850                 855                 860

Thr Met Gly Ser Val Ile Pro Asp Gly Ala Lys Trp Asp Asp Asp Cys
865                 870                 875                 880

Asn Thr Cys Gln Cys Leu Asn Gly Arg Ile Ala Cys Ser Lys Val Trp
                885                 890                 895

Cys Gly Pro Arg Pro Cys Leu Leu His Lys Gly His Ser Glu Cys Pro
            900                 905                 910

Ser Gly Gln Ser Cys Ile Pro Ile Leu Asp Asp Gln Cys Phe Val His
        915                 920                 925

Pro Cys Thr Gly Val Gly Glu Cys Arg Ser Ser Leu Gln Pro Val
    930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                965                 970                 975

Glu His Ile Cys Ser Glu Leu Arg Asn Leu Asn Ile Leu Lys Asn Val
            980                 985                 990

Ser Ala Glu Tyr Ser Ile Tyr Ile Ala Cys Glu Pro Ser  Pro Ser Ala
        995                 1000                1005

Asn Asn  Glu Ile His Val Ala  Ile Ser Ala Glu Asp  Ile Arg Asp
    1010                1015                1020

Asp Gly  Asn Pro Ile Lys Glu  Ile Thr Asp Lys Ile  Ile Asp Leu
    1025                1030                1035
```

-continued

Val Ser Lys Arg Asp Gly Asn Ser Ser Leu Ile Ala Ala Val Ala
    1040                1045                1050

Glu Val Arg Val Gln Arg Arg Pro Leu Lys Asn Arg Thr Asp Phe
    1055                1060                1065

Leu Val Pro Leu Leu Ser Ser Val Leu Thr Val Ala Trp Ile Cys
    1070                1075                1080

Cys Leu Val Thr Ala Phe Tyr Trp Cys Leu Arg Lys Arg Arg Lys
    1085                1090                1095

Pro Gly Ser His Thr His Ser Ala Ser Glu Asp Asn Thr Thr Asn
    1100                1105                1110

Asn Val Arg Glu Gln Leu Asn Gln Ile Lys Asn Pro Ile Glu Lys
    1115                1120                1125

His Gly Ala Asn Thr Val Pro Ile Lys Asp Tyr Glu Asn Lys Asn
    1130                1135                1140

Ser Lys Met Ser Lys Ile Arg Thr His Asn Ser Glu Val Glu Glu
    1145                1150                1155

Asp Asp Met Asp Lys His Gln Gln Lys Ala Arg Phe Ala Lys Gln
    1160                1165                1170

Pro Ala Tyr Thr Leu Val Asp Arg Glu Glu Lys Pro Pro Asn Gly
    1175                1180                1185

Thr Pro Thr Lys His Pro Asn Trp Thr Asn Lys Gln Asp Asn Arg
    1190                1195                1200

Asp Leu Glu Ser Ala Gln Ser Leu Asn Arg Met Glu Tyr Ile Val
    1205                1210                1215

<210> SEQ ID NO 2
<211> LENGTH: 1218
<212> TYPE: PRT
<213> ORGANISM: Unknown
<220> FEATURE:
<223> OTHER INFORMATION: Mus sp.

<400> SEQUENCE: 2

Met Arg Ser Pro Arg Thr Arg Gly Arg Pro Gly Arg Pro Leu Ser Leu
1               5                   10                  15

Leu Leu Ala Leu Leu Cys Ala Leu Arg Ala Lys Val Cys Gly Ala Ser
                20                  25                  30

Gly Gln Phe Glu Leu Glu Ile Leu Ser Met Gln Asn Val Asn Gly Glu
            35                  40                  45

Leu Gln Asn Gly Asn Cys Cys Gly Gly Val Arg Asn Pro Gly Asp Arg
        50                  55                  60

Lys Cys Thr Arg Asp Glu Cys Asp Thr Tyr Phe Lys Val Cys Leu Lys
65                  70                  75                  80

Glu Tyr Gln Ser Arg Val Thr Ala Gly Gly Pro Cys Ser Phe Gly Ser
                85                  90                  95

Gly Ser Thr Pro Val Ile Gly Gly Asn Thr Phe Asn Leu Lys Ala Ser
            100                 105                 110

Arg Gly Asn Asp Arg Asn Arg Ile Val Leu Pro Phe Ser Phe Ala Trp
        115                 120                 125

Pro Arg Ser Tyr Thr Leu Leu Val Glu Ala Trp Asp Ser Ser Asn Asp
    130                 135                 140

Thr Ile Gln Pro Asp Ser Ile Ile Glu Lys Ala Ser His Ser Gly Met
145                 150                 155                 160

Ile Asn Pro Ser Arg Gln Trp Gln Thr Leu Lys Gln Asn Thr Gly Ile
                165                 170                 175

```
Ala His Phe Glu Tyr Gln Ile Arg Val Thr Cys Asp Asp His Tyr Tyr
            180                 185                 190

Gly Phe Gly Cys Asn Lys Phe Cys Arg Pro Arg Asp Asp Phe Phe Gly
        195                 200                 205

His Tyr Ala Cys Asp Gln Asn Gly Asn Lys Thr Cys Met Glu Gly Trp
    210                 215                 220

Met Gly Pro Asp Cys Asn Lys Ala Ile Cys Arg Gln Gly Cys Ser Pro
225                 230                 235                 240

Lys His Gly Ser Cys Lys Leu Pro Gly Asp Cys Arg Cys Gln Tyr Gly
                245                 250                 255

Trp Gln Gly Leu Tyr Cys Asp Lys Cys Ile Pro His Pro Gly Cys Val
        260                 265                 270

His Gly Thr Cys Asn Glu Pro Trp Gln Cys Leu Cys Glu Thr Asn Trp
    275                 280                 285

Gly Gly Gln Leu Cys Asp Lys Asp Leu Asn Tyr Cys Gly Thr His Gln
290                 295                 300

Pro Cys Leu Asn Arg Gly Thr Cys Ser Asn Thr Gly Pro Asp Lys Tyr
305                 310                 315                 320

Gln Cys Ser Cys Pro Glu Gly Tyr Ser Gly Pro Asn Cys Glu Ile Ala
                325                 330                 335

Glu His Ala Cys Leu Ser Asp Pro Cys His Asn Arg Gly Ser Cys Lys
            340                 345                 350

Glu Thr Ser Ser Gly Phe Glu Cys Glu Cys Ser Pro Gly Trp Thr Gly
        355                 360                 365

Pro Thr Cys Ser Thr Asn Ile Asp Asp Cys Ser Pro Asn Asn Cys Ser
370                 375                 380

His Gly Gly Thr Cys Gln Asp Leu Val Asn Gly Phe Lys Cys Val Cys
385                 390                 395                 400

Pro Pro Gln Trp Thr Gly Lys Thr Cys Gln Leu Asp Ala Asn Glu Cys
                405                 410                 415

Glu Ala Lys Pro Cys Val Asn Ala Arg Ser Cys Lys Asn Leu Ile Ala
            420                 425                 430

Ser Tyr Tyr Cys Asp Cys Leu Pro Gly Trp Met Gly Gln Asn Cys Asp
        435                 440                 445

Ile Asn Ile Asn Asp Cys Leu Gly Gln Cys Gln Asn Asp Ala Ser Cys
450                 455                 460

Arg Asp Leu Val Asn Gly Tyr Arg Cys Ile Cys Pro Pro Gly Tyr Ala
465                 470                 475                 480

Gly Asp His Cys Glu Arg Asp Ile Asp Glu Cys Ala Ser Asn Pro Cys
                485                 490                 495

Leu Asn Gly Gly His Cys Gln Asn Glu Ile Asn Arg Phe Gln Cys Leu
            500                 505                 510

Cys Pro Thr Gly Phe Ser Gly Asn Leu Cys Gln Leu Asp Ile Asp Tyr
        515                 520                 525

Cys Glu Pro Asn Pro Cys Gln Asn Gly Ala Gln Cys Tyr Asn Arg Ala
530                 535                 540

Ser Asp Tyr Phe Cys Lys Cys Pro Glu Asp Tyr Glu Gly Lys Asn Cys
545                 550                 555                 560

Ser His Leu Lys Asp His Cys Arg Thr Thr Thr Cys Glu Val Ile Asp
                565                 570                 575

Ser Cys Thr Val Ala Met Ala Ser Asn Asp Thr Pro Glu Gly Val Arg
            580                 585                 590

Tyr Ile Ser Ser Asn Val Cys Gly Pro His Gly Lys Cys Lys Ser Gln
```

-continued

```
                    595                 600                 605
Ser Gly Gly Lys Phe Thr Cys Asp Cys Asn Lys Gly Phe Thr Gly Thr
610                 615                 620

Tyr Cys His Glu Asn Ile Asn Asp Cys Glu Ser Asn Pro Cys Lys Asn
625                 630                 635                 640

Gly Gly Thr Cys Ile Asp Gly Val Asn Ser Tyr Lys Cys Ile Cys Ser
                    645                 650                 655

Asp Gly Trp Glu Gly Ala His Cys Glu Asn Asn Ile Asn Asp Cys Ser
                    660                 665                 670

Gln Asn Pro Cys His Tyr Gly Gly Thr Cys Arg Asp Leu Val Asn Asp
                675                 680                 685

Phe Tyr Cys Asp Cys Lys Asn Gly Trp Lys Gly Lys Thr Cys His Ser
690                 695                 700

Arg Asp Ser Gln Cys Asp Glu Ala Thr Cys Asn Asn Gly Gly Thr Cys
705                 710                 715                 720

Tyr Asp Glu Val Asp Thr Phe Lys Cys Met Cys Pro Gly Gly Trp Glu
                    725                 730                 735

Gly Thr Thr Cys Asn Ile Ala Arg Asn Ser Ser Cys Leu Pro Asn Pro
                    740                 745                 750

Cys His Asn Gly Gly Thr Cys Val Val Asn Gly Asp Ser Phe Thr Cys
                755                 760                 765

Val Cys Lys Glu Gly Trp Glu Gly Pro Ile Cys Thr Gln Asn Thr Asn
770                 775                 780

Asp Cys Ser Pro His Pro Cys Tyr Asn Ser Gly Thr Cys Val Asp Gly
785                 790                 795                 800

Asp Asn Trp Tyr Arg Cys Glu Cys Ala Pro Gly Phe Ala Gly Pro Asp
                    805                 810                 815

Cys Arg Ile Asn Ile Asn Glu Cys Gln Ser Ser Pro Cys Ala Phe Gly
                    820                 825                 830

Ala Thr Cys Val Asp Glu Ile Asn Gly Tyr Gln Cys Ile Cys Pro Pro
                835                 840                 845

Gly His Ser Gly Ala Lys Cys His Glu Val Ser Gly Arg Ser Cys Ile
                850                 855                 860

Thr Met Gly Arg Val Ile Leu Asp Gly Ala Lys Trp Asp Asp Asp Cys
865                 870                 875                 880

Asn Thr Cys Gln Cys Leu Asn Gly Arg Val Ala Cys Ser Lys Val Trp
                    885                 890                 895

Cys Gly Pro Arg Pro Cys Arg Leu His Lys Ser His Asn Glu Cys Pro
                    900                 905                 910

Ser Gly Gln Ser Cys Ile Pro Val Leu Asp Asp Gln Cys Phe Val Arg
                915                 920                 925

Pro Cys Thr Gly Val Gly Glu Cys Arg Ser Ser Leu Gln Pro Val
                930                 935                 940

Lys Thr Lys Cys Thr Ser Asp Ser Tyr Tyr Gln Asp Asn Cys Ala Asn
945                 950                 955                 960

Ile Thr Phe Thr Phe Asn Lys Glu Met Met Ser Pro Gly Leu Thr Thr
                    965                 970                 975

Glu His Ile Cys Ser Glu Leu Arg Asn Leu Asn Ile Leu Lys Asn Val
                980                 985                 990

Ser Ala Glu Tyr Ser Ile Tyr Ile Ala Cys Glu Pro Ser Leu Ser Ala
                995                 1000                1005

Asn Asn Glu Ile His Val Ala Ile Ser Ala Glu Asp Ile Arg Asp
     1010                1015                1020
```

```
Asp Gly Asn Pro Val Lys Glu Ile Thr Asp Lys Ile Ile Asp Leu
        1025                1030                1035

Val Ser Lys Arg Asp Gly Asn Ser Ser Leu Ile Ala Ala Val Ala
        1040                1045                1050

Glu Val Arg Val Gln Arg Arg Pro Leu Lys Asn Arg Thr Asp Phe
        1055                1060                1065

Leu Val Pro Leu Leu Ser Ser Val Leu Thr Val Ala Trp Val Cys
        1070                1075                1080

Cys Leu Val Thr Ala Phe Tyr Trp Cys Val Arg Lys Arg Arg Lys
        1085                1090                1095

Pro Ser Ser His Thr His Ser Ala Pro Glu Asp Asn Thr Thr Asn
        1100                1105                1110

Asn Val Arg Glu Gln Leu Asn Gln Ile Lys Asn Pro Ile Glu Lys
        1115                1120                1125

His Gly Ala Asn Thr Val Pro Ile Lys Asp Tyr Glu Asn Lys Asn
        1130                1135                1140

Ser Lys Met Ser Lys Ile Arg Thr His Asn Ser Glu Val Glu Glu
        1145                1150                1155

Asp Asp Met Asp Lys His Gln Gln Lys Val Arg Phe Ala Lys Gln
        1160                1165                1170

Pro Val Tyr Thr Leu Val Asp Arg Glu Glu Lys Ala Pro Ser Gly
        1175                1180                1185

Thr Pro Thr Lys His Pro Asn Trp Thr Asn Lys Gln Asp Asn Arg
        1190                1195                1200

Asp Leu Glu Ser Ala Gln Ser Leu Asn Arg Met Glu Tyr Ile Val
        1205                1210                1215

<210> SEQ ID NO 3
<211> LENGTH: 1238
<212> TYPE: PRT
<213> ORGANISM: Homo sapiens

<400> SEQUENCE: 3

Met Arg Ala Gln Gly Arg Gly Arg Leu Pro Arg Arg Leu Leu Leu
1               5                   10                  15

Leu Ala Leu Trp Val Gln Ala Ala Arg Pro Met Gly Tyr Phe Glu Leu
                20                  25                  30

Gln Leu Ser Ala Leu Arg Asn Val Asn Gly Glu Leu Leu Ser Gly Ala
                35                  40                  45

Cys Cys Asp Gly Asp Gly Arg Thr Thr Arg Ala Gly Gly Cys Gly His
        50                  55                  60

Asp Glu Cys Asp Thr Tyr Val Arg Val Cys Leu Lys Glu Tyr Gln Ala
65                  70                  75                  80

Lys Val Thr Pro Thr Gly Pro Cys Ser Tyr Gly His Gly Ala Thr Pro
                85                  90                  95

Val Leu Gly Gly Asn Ser Phe Tyr Leu Pro Pro Ala Gly Ala Ala Gly
                100                 105                 110

Asp Arg Ala Arg Ala Arg Ala Arg Ala Gly Gly Asp Gln Asp Pro Gly
                115                 120                 125

Leu Val Val Ile Pro Phe Gln Phe Ala Trp Pro Arg Ser Phe Thr Leu
                130                 135                 140

Ile Val Glu Ala Trp Asp Trp Asp Asn Asp Thr Thr Pro Asn Glu Glu
145                 150                 155                 160

Leu Leu Ile Glu Arg Val Ser His Ala Gly Met Ile Asn Pro Glu Asp
```

```
              165                 170                 175
Arg Trp Lys Ser Leu His Phe Ser Gly His Val Ala His Leu Glu Leu
            180                 185                 190

Gln Ile Arg Val Arg Cys Asp Glu Asn Tyr Tyr Ser Ala Thr Cys Asn
            195                 200                 205

Lys Phe Cys Arg Pro Arg Asn Asp Phe Phe Gly His Tyr Thr Cys Asp
        210                 215                 220

Gln Tyr Gly Asn Lys Ala Cys Met Asp Gly Trp Met Gly Lys Glu Cys
225                 230                 235                 240

Lys Glu Ala Val Cys Lys Gln Gly Cys Asn Leu Leu His Gly Gly Cys
                245                 250                 255

Thr Val Pro Gly Glu Cys Arg Cys Ser Tyr Gly Trp Gln Gly Arg Phe
            260                 265                 270

Cys Asp Glu Cys Val Pro Tyr Pro Gly Cys Val His Gly Ser Cys Val
        275                 280                 285

Glu Pro Trp Gln Cys Asn Cys Glu Thr Asn Trp Gly Gly Leu Leu Cys
        290                 295                 300

Asp Lys Asp Leu Asn Tyr Cys Gly Ser His His Pro Cys Thr Asn Gly
305                 310                 315                 320

Gly Thr Cys Ile Asn Ala Glu Pro Asp Gln Tyr Arg Cys Thr Cys Pro
                325                 330                 335

Asp Gly Tyr Ser Gly Arg Asn Cys Glu Lys Ala Glu His Ala Cys Thr
            340                 345                 350

Ser Asn Pro Cys Ala Asn Gly Gly Ser Cys His Glu Val Pro Ser Gly
            355                 360                 365

Phe Glu Cys His Cys Pro Ser Gly Trp Ser Gly Pro Thr Cys Ala Leu
        370                 375                 380

Asp Ile Asp Glu Cys Ala Ser Asn Pro Cys Ala Ala Gly Gly Thr Cys
385                 390                 395                 400

Val Asp Gln Val Asp Gly Phe Glu Cys Ile Cys Pro Glu Gln Trp Val
                405                 410                 415

Gly Ala Thr Cys Gln Leu Asp Ala Asn Glu Cys Glu Gly Lys Pro Cys
            420                 425                 430

Leu Asn Ala Phe Ser Cys Lys Asn Leu Ile Gly Gly Tyr Tyr Cys Asp
        435                 440                 445

Cys Ile Pro Gly Trp Lys Gly Ile Asn Cys His Ile Asn Val Asn Asp
        450                 455                 460

Cys Arg Gly Gln Cys Gln His Gly Gly Thr Cys Lys Asp Leu Val Asn
465                 470                 475                 480

Gly Tyr Gln Cys Val Cys Pro Arg Gly Phe Gly Gly Arg His Cys Glu
                485                 490                 495

Leu Glu Arg Asp Glu Cys Ala Ser Ser Pro Cys His Ser Gly Gly Leu
            500                 505                 510

Cys Glu Asp Leu Ala Asp Gly Phe His Cys His Cys Pro Gln Gly Phe
        515                 520                 525

Ser Gly Pro Leu Cys Glu Val Asp Val Asp Leu Cys Glu Pro Ser Pro
        530                 535                 540

Cys Arg Asn Gly Ala Arg Cys Tyr Asn Leu Glu Gly Asp Tyr Tyr Cys
545                 550                 555                 560

Ala Cys Pro Asp Asp Phe Gly Gly Lys Asn Cys Ser Val Pro Arg Glu
                565                 570                 575

Pro Cys Pro Gly Gly Ala Cys Arg Val Ile Asp Gly Cys Gly Ser Asp
            580                 585                 590
```

```
Ala Gly Pro Gly Met Pro Gly Thr Ala Ala Ser Gly Val Cys Gly Pro
        595                 600                 605
His Gly Arg Cys Val Ser Gln Pro Gly Gly Asn Phe Ser Cys Ile Cys
        610                 615                 620
Asp Ser Gly Phe Thr Gly Thr Tyr Cys His Glu Asn Ile Asp Asp Cys
625                 630                 635                 640
Leu Gly Gln Pro Cys Arg Asn Gly Gly Thr Cys Ile Asp Glu Val Asp
                    645                 650                 655
Ala Phe Arg Cys Phe Cys Pro Ser Gly Trp Glu Gly Glu Leu Cys Asp
                    660                 665                 670
Thr Asn Pro Asn Asp Cys Leu Pro Asp Pro Cys His Ser Arg Gly Arg
                    675                 680                 685
Cys Tyr Asp Leu Val Asn Asp Phe Tyr Cys Ala Cys Asp Asp Gly Trp
        690                 695                 700
Lys Gly Lys Thr Cys His Ser Arg Glu Phe Gln Cys Asp Ala Tyr Thr
705                 710                 715                 720
Cys Ser Asn Gly Gly Thr Cys Tyr Asp Ser Gly Asp Thr Phe Arg Cys
                    725                 730                 735
Ala Cys Pro Pro Gly Trp Lys Gly Ser Thr Cys Ala Val Ala Lys Asn
                    740                 745                 750
Ser Ser Cys Leu Pro Asn Pro Cys Val Asn Gly Gly Thr Cys Val Gly
        755                 760                 765
Ser Gly Ala Ser Phe Ser Cys Ile Cys Arg Asp Gly Trp Glu Gly Arg
        770                 775                 780
Thr Cys Thr His Asn Thr Asn Asp Cys Asn Pro Leu Pro Cys Tyr Asn
785                 790                 795                 800
Gly Gly Ile Cys Val Asp Gly Val Asn Trp Phe Arg Cys Glu Cys Ala
                    805                 810                 815
Pro Gly Phe Ala Gly Pro Asp Cys Arg Ile Asn Ile Asp Glu Cys Gln
                    820                 825                 830
Ser Ser Pro Cys Ala Tyr Gly Ala Thr Cys Val Asp Glu Ile Asn Gly
        835                 840                 845
Tyr Arg Cys Ser Cys Pro Gly Arg Ala Gly Pro Arg Cys Gln Glu
        850                 855                 860
Val Ile Gly Phe Gly Arg Ser Cys Trp Ser Arg Gly Thr Pro Phe Pro
865                 870                 875                 880
His Gly Ser Ser Trp Val Glu Asp Cys Asn Ser Cys Arg Cys Leu Asp
                    885                 890                 895
Gly Arg Arg Asp Cys Ser Lys Val Trp Cys Gly Trp Lys Pro Cys Leu
                    900                 905                 910
Leu Ala Gly Gln Pro Glu Ala Leu Ser Ala Gln Cys Pro Leu Gly Gln
        915                 920                 925
Arg Cys Leu Glu Lys Ala Pro Gly Gln Cys Leu Arg Pro Cys Glu
        930                 935                 940
Ala Trp Gly Glu Cys Gly Ala Glu Glu Pro Ser Thr Pro Cys Leu
945                 950                 955                 960
Pro Arg Ser Gly His Leu Asp Asn Asn Cys Ala Arg Leu Thr Leu His
                    965                 970                 975
Phe Asn Arg Asp His Val Pro Gln Gly Thr Thr Val Gly Ala Ile Cys
                    980                 985                 990
Ser Gly Ile Arg Ser Leu Pro Ala  Thr Arg Ala Val Ala  Arg Asp Arg
        995                 1000                1005
```

-continued

Leu Leu Val Leu Leu Cys Asp Arg Ala Ser Ser Gly Ala Ser Ala
    1010                1015                1020

Val Glu Val Ala Val Ser Phe Ser Pro Ala Arg Asp Leu Pro Asp
1025                1030                1035

Ser Ser Leu Ile Gln Gly Ala Ala His Ala Ile Val Ala Ala Ile
    1040                1045                1050

Thr Gln Arg Gly Asn Ser Ser Leu Leu Leu Ala Val Thr Glu Val
    1055                1060                1065

Lys Val Glu Thr Val Val Thr Gly Gly Ser Ser Thr Gly Leu Leu
    1070                1075                1080

Val Pro Val Leu Cys Gly Ala Phe Ser Val Leu Trp Leu Ala Cys
    1085                1090                1095

Val Val Leu Cys Val Trp Trp Thr Arg Lys Arg Arg Lys Glu Arg
    1100                1105                1110

Glu Arg Ser Arg Leu Pro Arg Glu Glu Ser Ala Asn Asn Gln Trp
    1115                1120                1125

Ala Pro Leu Asn Pro Ile Arg Asn Pro Ile Glu Arg Pro Gly Gly
    1130                1135                1140

His Lys Asp Val Leu Tyr Gln Cys Lys Asn Phe Thr Pro Pro Pro
    1145                1150                1155

Arg Arg Ala Asp Glu Ala Leu Pro Gly Pro Ala Gly His Ala Ala
    1160                1165                1170

Val Arg Glu Asp Glu Asp Glu Asp Leu Gly Arg Gly Glu Glu
    1175                1180                1185

Asp Ser Leu Glu Ala Glu Lys Phe Leu Ser His Lys Phe Thr Lys
    1190                1195                1200

Asp Pro Gly Arg Ser Pro Gly Arg Pro Ala His Trp Ala Ser Gly
    1205                1210                1215

Pro Lys Val Asp Asn Arg Ala Val Arg Ser Ile Asn Glu Ala Arg
    1220                1225                1230

Tyr Ala Gly Lys Glu
    1235

<210> SEQ ID NO 4
<211> LENGTH: 1247
<212> TYPE: PRT
<213> ORGANISM: Unknown
<220> FEATURE:
<223> OTHER INFORMATION: Mus sp.

<400> SEQUENCE: 4

Met Arg Ala Arg Gly Trp Gly Arg Leu Pro Arg Arg Leu Leu Leu
1               5                   10                  15

Leu Val Leu Cys Val Gln Ala Thr Arg Pro Met Gly Tyr Phe Glu Leu
            20                  25                  30

Gln Leu Ser Ala Leu Arg Asn Val Asn Gly Glu Leu Leu Ser Gly Ala
        35                  40                  45

Cys Cys Asp Gly Asp Gly Arg Thr Thr Arg Ala Gly Gly Cys Gly Arg
    50                  55                  60

Asp Glu Cys Asp Thr Tyr Val Arg Val Cys Leu Lys Glu Tyr Gln Ala
65                  70                  75                  80

Lys Val Thr Pro Thr Gly Pro Cys Ser Tyr Gly Tyr Gly Ala Thr Pro
                85                  90                  95

Val Leu Gly Gly Asn Ser Phe Tyr Leu Pro Pro Ala Gly Ala Ala Gly
            100                 105                 110

```
Asp Arg Ala Arg Ala Arg Ser Arg Thr Gly Gly His Gln Asp Pro Gly
            115                 120                 125
Leu Val Val Ile Pro Phe Gln Phe Ala Trp Pro Arg Ser Phe Thr Leu
        130                 135                 140
Ile Val Glu Ala Trp Asp Trp Asp Asn Asp Thr Thr Pro Asp Glu Glu
145                 150                 155                 160
Leu Leu Ile Glu Arg Val Ser His Ala Gly Met Ile Asn Pro Glu Asp
                165                 170                 175
Arg Trp Lys Ser Leu His Phe Ser Gly His Val Ala His Leu Glu Leu
            180                 185                 190
Gln Ile Arg Val Arg Cys Asp Glu Asn Tyr Tyr Ser Ala Thr Cys Asn
        195                 200                 205
Lys Phe Cys Arg Pro Arg Asn Asp Phe Phe Gly His Tyr Thr Cys Asp
    210                 215                 220
Gln Tyr Gly Asn Lys Ala Cys Met Asp Gly Trp Met Gly Lys Glu Cys
225                 230                 235                 240
Lys Glu Ala Val Cys Lys Gln Gly Cys Asn Leu Leu His Gly Gly Cys
                245                 250                 255
Thr Val Pro Gly Glu Cys Arg Cys Ser Tyr Gly Trp Gln Gly Lys Phe
            260                 265                 270
Cys Asp Glu Cys Val Pro Tyr Pro Gly Cys Val His Gly Ser Cys Val
        275                 280                 285
Glu Pro Trp His Cys Asp Cys Glu Thr Asn Trp Gly Gly Leu Leu Cys
    290                 295                 300
Asp Lys Asp Leu Asn Tyr Cys Gly Ser His His Pro Cys Val Asn Gly
305                 310                 315                 320
Gly Thr Cys Ile Asn Ala Glu Pro Asp Gln Tyr Leu Cys Ala Cys Pro
                325                 330                 335
Asp Gly Tyr Leu Gly Lys Asn Cys Glu Arg Ala Glu His Ala Cys Ala
            340                 345                 350
Ser Asn Pro Cys Ala Asn Gly Gly Ser Cys His Glu Val Pro Ser Gly
        355                 360                 365
Phe Glu Cys His Cys Pro Ser Gly Trp Ser Gly Pro Thr Cys Ala Leu
    370                 375                 380
Asp Ile Asp Glu Cys Ala Ser Asn Pro Cys Ala Ala Gly Gly Thr Cys
385                 390                 395                 400
Val Asp Gln Val Asp Gly Phe Glu Cys Ile Cys Pro Glu Gln Trp Val
                405                 410                 415
Gly Ala Thr Cys Gln Leu Asp Ala Asn Glu Cys Glu Gly Lys Pro Cys
            420                 425                 430
Leu Asn Ala Phe Ser Cys Lys Asn Leu Ile Gly Gly Tyr Tyr Cys Asp
        435                 440                 445
Cys Leu Pro Gly Trp Lys Gly Ile Asn Cys Gln Ile Asn Ile Asn Asp
    450                 455                 460
Cys His Gly Gln Cys Gln His Gly Gly Thr Cys Lys Asp Leu Val Asn
465                 470                 475                 480
Gly Tyr Gln Cys Val Cys Pro Arg Gly Phe Gly Gly Arg His Cys Glu
                485                 490                 495
Leu Glu Tyr Asp Lys Cys Ala Ser Pro Cys Arg Arg Gly Gly Ile
            500                 505                 510
Cys Glu Asp Leu Val Asp Gly Phe Arg Cys His Cys Pro Arg Gly Leu
        515                 520                 525
Ser Gly Leu His Cys Glu Val Asp Met Asp Leu Cys Glu Pro Ser Pro
```

-continued

```
                530                 535                 540
Cys Leu Asn Gly Ala Arg Cys Tyr Asn Leu Glu Gly Asp Tyr Tyr Cys
545                 550                 555                 560

Ala Cys Pro Glu Asp Phe Gly Gly Lys Asn Cys Ser Val Pro Arg Asp
                565                 570                 575

Thr Cys Pro Gly Gly Ala Cys Arg Val Ile Asp Gly Cys Gly Phe Glu
                580                 585                 590

Ala Gly Ser Arg Ala Arg Gly Val Ala Pro Ser Gly Ile Cys Gly Pro
                595                 600                 605

His Gly His Cys Val Ser Leu Pro Gly Gly Asn Phe Ser Cys Ile Cys
                610                 615                 620

Asp Ser Gly Phe Thr Gly Thr Tyr Cys His Glu Asn Ile Asp Asp Cys
625                 630                 635                 640

Met Gly Gln Pro Cys Arg Asn Gly Gly Thr Cys Ile Asp Glu Val Asp
                645                 650                 655

Ser Phe Arg Cys Phe Cys Pro Ser Gly Trp Glu Gly Glu Leu Cys Asp
                660                 665                 670

Ile Asn Pro Asn Asp Cys Leu Pro Asp Pro Cys His Ser Arg Gly Arg
                675                 680                 685

Cys Tyr Asp Leu Val Asn Asp Phe Tyr Cys Ala Cys Asp Asp Gly Trp
                690                 695                 700

Lys Gly Lys Thr Cys His Ser Arg Glu Phe Gln Cys Asp Ala Tyr Thr
705                 710                 715                 720

Cys Ser Asn Gly Gly Thr Cys Tyr Asp Ser Gly Asp Thr Phe Arg Cys
                725                 730                 735

Ala Cys Pro Pro Gly Trp Lys Gly Ser Thr Cys Thr Ile Ala Lys Asn
                740                 745                 750

Ser Ser Cys Val Pro Asn Pro Cys Val Asn Gly Gly Thr Cys Val Gly
                755                 760                 765

Ser Gly Asp Ser Phe Ser Cys Ile Cys Arg Asp Gly Trp Glu Gly Arg
                770                 775                 780

Thr Cys Thr His Asn Thr Asn Asp Cys Asn Pro Leu Pro Cys Tyr Asn
785                 790                 795                 800

Gly Gly Ile Cys Val Asp Gly Val Asn Trp Phe Arg Cys Glu Cys Ala
                805                 810                 815

Pro Gly Phe Ala Gly Pro Asp Cys Arg Ile Asn Ile Asp Glu Cys Gln
                820                 825                 830

Ser Ser Pro Cys Ala Tyr Gly Ala Thr Cys Val Asp Glu Ile Asn Gly
                835                 840                 845

Tyr Arg Cys Ser Cys Pro Pro Gly Arg Ser Gly Pro Arg Cys Gln Glu
850                 855                 860

Val Val Ile Phe Thr Arg Pro Cys Trp Ser Arg Gly Met Ser Phe Pro
865                 870                 875                 880

His Gly Ser Ser Trp Met Glu Asp Cys Asn Ser Cys Arg Cys Leu Asp
                885                 890                 895

Gly His Arg Asp Cys Ser Lys Val Trp Cys Gly Trp Lys Pro Cys Leu
                900                 905                 910

Leu Ser Gly Gln Pro Ser Asp Pro Ser Ala Gln Cys Pro Pro Gly Gln
                915                 920                 925

Gln Cys Gln Glu Lys Ala Val Gly Gln Cys Leu Gln Pro Pro Cys Glu
                930                 935                 940

Asn Trp Gly Glu Cys Thr Ala Glu Glu Pro Leu Pro Pro Ser Thr Pro
945                 950                 955                 960
```

-continued

```
Cys Gln Pro Arg Ser Ser His Leu Asp Asn Asn Cys Ala Arg Leu Thr
            965                 970                 975

Leu Arg Phe Asn Arg Asp Gln Val Pro Gln Gly Thr Thr Val Gly Ala
            980                 985                 990

Ile Cys Ser Gly Ile Arg Ala Leu Pro Ala Thr Arg Ala Ala Ala His
            995                1000                1005

Asp Arg Leu Leu Leu Leu Leu Cys Asp Arg Ala Ser Ser Gly Ala
           1010                1015                1020

Ser Ala Val Glu Val Ala Met Ser Phe Ser Pro Ala Arg Asp Leu
           1025                1030                1035

Pro Asp Ser Ser Leu Ile Gln Ser Thr Ala His Ala Ile Val Ala
           1040                1045                1050

Ala Ile Thr Gln Arg Gly Asn Ser Ser Leu Leu Leu Ala Val Thr
           1055                1060                1065

Glu Val Lys Val Glu Thr Val Met Gly Gly Ser Ser Thr Gly
           1070                1075                1080

Leu Leu Val Pro Val Leu Cys Ser Val Phe Ser Val Leu Trp Leu
           1085                1090                1095

Ala Cys Val Val Ile Cys Val Trp Trp Thr Arg Lys Arg Arg Lys
           1100                1105                1110

Glu Arg Glu Arg Ser Arg Leu Pro Arg Asp Glu Ser Thr Asn Asn
           1115                1120                1125

Gln Trp Ala Pro Leu Asn Pro Ile Arg Asn Pro Ile Glu Arg Pro
           1130                1135                1140

Gly Gly Ser Gly Leu Gly Thr Gly Gly His Lys Asp Ile Leu Tyr
           1145                1150                1155

Gln Cys Lys Asn Phe Thr Pro Pro Pro Arg Arg Ala Gly Glu Ala
           1160                1165                1170

Leu Pro Gly Pro Ala Gly His Gly Ala Gly Gly Glu Asp Glu Glu
           1175                1180                1185

Asp Glu Glu Leu Ser Arg Gly Asp Gly Asp Ser Pro Glu Ala Glu
           1190                1195                1200

Lys Phe Ile Ser His Lys Phe Thr Lys Asp Pro Ser Cys Ser Leu
           1205                1210                1215

Gly Arg Pro Ala Cys Trp Ala Pro Gly Pro Lys Val Asp Asn Arg
           1220                1225                1230

Ala Val Arg Ser Thr Lys Asp Val Arg Arg Ala Gly Arg Glu
           1235                1240                1245

<210> SEQ ID NO 5
<211> LENGTH: 365
<212> TYPE: PRT
<213> ORGANISM: Artificial Sequence
<220> FEATURE:
<223> OTHER INFORMATION: Synthetic polypeptide

<400> SEQUENCE: 5

Ala Asp Leu Gly Ser Gln Phe Glu Leu Glu Ile Leu Ser Met Gln Asn
1               5                   10                  15

Val Asn Gly Glu Leu Gln Asn Gly Asn Cys Cys Gly Gly Val Arg Asn
                20                  25                  30

Pro Gly Asp Arg Lys Cys Thr Arg Asp Glu Cys Asp Thr Tyr Phe Lys
            35                  40                  45

Val Cys Leu Lys Glu Tyr Gln Ser Arg Val Thr Ala Gly Gly Pro Cys
        50                  55                  60
```

Ser Phe Gly Ser Gly Ser Thr Pro Val Ile Gly Asn Thr Phe Asn
65                  70                  75                  80

Leu Lys Ala Ser Arg Gly Asn Asp Arg Asn Arg Ile Val Leu Pro Phe
            85                  90                  95

Ser Phe Ala Trp Pro Arg Ser Tyr Thr Leu Leu Val Glu Ala Trp Asp
            100                 105                 110

Ser Ser Asn Asp Thr Ile Gln Pro Asp Ser Ile Ile Glu Lys Ala Ser
            115                 120                 125

His Ser Gly Met Ile Asn Pro Ser Arg Gln Trp Gln Thr Leu Lys Gln
130                 135                 140

Asn Thr Gly Ile Ala His Phe Glu Tyr Gln Ile Arg Val Thr Cys Asp
145                 150                 155                 160

Asp His Tyr Tyr Gly Phe Gly Cys Asn Lys Phe Cys Arg Pro Arg Asp
                165                 170                 175

Asp Phe Phe Gly His Tyr Ala Cys Asp Gln Asn Gly Asn Lys Thr Cys
            180                 185                 190

Met Glu Gly Trp Met Gly Pro Asp Cys Asn Lys Ala Ile Cys Arg Gln
            195                 200                 205

Gly Cys Ser Pro Lys His Gly Ser Cys Lys Leu Pro Gly Asp Cys Arg
210                 215                 220

Cys Gln Tyr Gly Trp Gln Gly Leu Tyr Cys Asp Lys Cys Ile Pro His
225                 230                 235                 240

Pro Gly Cys Val His Gly Thr Cys Asn Glu Pro Trp Gln Cys Leu Cys
                245                 250                 255

Glu Thr Asn Trp Gly Gly Gln Leu Cys Asp Lys Asp Leu Asn Tyr Cys
            260                 265                 270

Gly Thr His Gln Pro Cys Leu Asn Arg Gly Thr Cys Ser Asn Thr Gly
            275                 280                 285

Pro Asp Lys Tyr Gln Cys Ser Cys Pro Glu Gly Tyr Ser Gly Pro Asn
290                 295                 300

Cys Glu Ile Ala Glu His Ala Cys Leu Ser Asp Pro Cys His Asn Arg
305                 310                 315                 320

Gly Ser Cys Lys Glu Thr Ser Ser Gly Phe Glu Cys Glu Cys Ser Pro
                325                 330                 335

Gly Trp Thr Gly Pro Thr Cys Ser Thr Asn Ile Asp Asp Glu Phe Gly
            340                 345                 350

Leu Val Pro Arg Gly Ser Gly His His His His His
            355                 360                 365

<210> SEQ ID NO 6
<211> LENGTH: 344
<212> TYPE: PRT
<213> ORGANISM: Artificial Sequence
<220> FEATURE:
<223> OTHER INFORMATION: Synthetic polypeptide

<400> SEQUENCE: 6

Gln Phe Glu Leu Glu Ile Leu Ser Met Gln Asn Val Asn Gly Glu Leu
1               5                   10                  15

Gln Asn Gly Asn Cys Cys Gly Gly Ala Arg Asn Pro Gly Asp Arg Lys
            20                  25                  30

Cys Thr Arg Asp Glu Cys Asp Thr Tyr Phe Lys Val Cys Leu Lys Glu
            35                  40                  45

Tyr Gln Ser Arg Val Thr Ala Gly Gly Pro Cys Ser Phe Gly Ser Gly
50                  55                  60

-continued

Ser Thr Pro Val Ile Gly Gly Asn Thr Phe Asn Leu Lys Ala Ser Arg
 65                  70                  75                  80

Gly Asn Asp Arg Asn Arg Ile Val Leu Pro Phe Ser Phe Ala Trp Pro
                 85                  90                  95

Arg Ser Tyr Thr Leu Leu Val Glu Ala Trp Asp Ser Ser Asn Asp Thr
            100                 105                 110

Val Gln Pro Asp Ser Ile Ile Glu Lys Ala Ser His Ser Gly Met Ile
        115                 120                 125

Asn Pro Ser Arg Gln Trp Gln Thr Leu Lys Gln Asn Thr Gly Val Ala
130                 135                 140

His Phe Glu Tyr Gln Ile Arg Val Thr Cys Asp Asp Tyr Tyr Tyr Gly
145                 150                 155                 160

Phe Gly Cys Asn Lys Phe Cys Arg Pro Arg Asp Asp Phe Phe Gly His
                165                 170                 175

Tyr Ala Cys Asp Gln Asn Gly Asn Lys Thr Cys Met Glu Gly Trp Met
            180                 185                 190

Gly Pro Glu Cys Asn Arg Ala Ile Cys Arg Gln Gly Cys Ser Pro Lys
        195                 200                 205

His Gly Ser Cys Lys Leu Pro Gly Asp Cys Arg Cys Gln Tyr Gly Trp
210                 215                 220

Gln Gly Leu Tyr Cys Asp Lys Cys Ile Pro His Pro Gly Cys Val His
225                 230                 235                 240

Gly Ile Cys Asn Glu Pro Trp Gln Cys Leu Cys Glu Thr Asn Trp Gly
                245                 250                 255

Gly Gln Leu Cys Asp Lys Asp Leu Asn Tyr Cys Gly Thr His Gln Pro
            260                 265                 270

Cys Leu Asn Gly Gly Thr Cys Ser Asn Thr Gly Pro Asp Lys Tyr Gln
        275                 280                 285

Cys Ser Cys Pro Glu Gly Tyr Ser Gly Pro Asn Cys Glu Ile Ala Glu
        290                 295                 300

His Ala Cys Leu Ser Asp Pro Cys His Asn Arg Gly Ser Cys Lys Glu
305                 310                 315                 320

Thr Ser Leu Gly Phe Glu Cys Glu Cys Ser Pro Gly Trp Thr Gly Pro
                325                 330                 335

Thr Cys Ser Thr Asn Ile Asp Asp
            340

<210> SEQ ID NO 7
<211> LENGTH: 383
<212> TYPE: PRT
<213> ORGANISM: Artificial Sequence
<220> FEATURE:
<223> OTHER INFORMATION: Synthetic polypeptide

<400> SEQUENCE: 7

Ala Asp Leu Gly Ser Met Gly Tyr Phe Glu Leu Gln Leu Ser Ala Leu
 1               5                  10                  15

Arg Asn Val Asn Gly Glu Leu Leu Ser Gly Ala Cys Cys Asp Gly Asp
                20                  25                  30

Gly Arg Thr Thr Arg Ala Gly Gly Cys Gly Arg Asp Glu Cys Asp Thr
            35                  40                  45

Tyr Val Arg Val Cys Leu Lys Glu Tyr Gln Ala Lys Val Thr Pro Thr
        50                  55                  60

Gly Pro Cys Ser Tyr Gly Tyr Gly Ala Thr Pro Val Leu Gly Gly Asn
 65                  70                  75                  80

-continued

```
Ser Phe Tyr Leu Pro Pro Ala Gly Ala Gly Asp Arg Ala Arg Ala
                 85                  90                  95

Arg Ser Arg Thr Gly Gly His Gln Asp Pro Gly Leu Val Val Ile Pro
            100                 105                 110

Phe Gln Phe Ala Trp Pro Arg Ser Phe Thr Leu Ile Val Glu Ala Trp
        115                 120                 125

Asp Trp Asp Asn Asp Thr Thr Pro Asp Glu Leu Leu Ile Glu Arg
130                 135                 140

Val Ser His Ala Gly Met Ile Asn Pro Glu Asp Arg Trp Lys Ser Leu
145                 150                 155                 160

His Phe Ser Gly His Val Ala His Leu Glu Leu Gln Ile Arg Val Arg
                165                 170                 175

Cys Asp Glu Asn Tyr Tyr Ser Ala Thr Cys Asn Lys Phe Cys Arg Pro
            180                 185                 190

Arg Asn Asp Phe Phe Gly His Tyr Thr Cys Asp Gln Tyr Gly Asn Lys
        195                 200                 205

Ala Cys Met Asp Gly Trp Met Gly Lys Glu Cys Lys Glu Ala Val Cys
    210                 215                 220

Lys Gln Gly Cys Asn Leu Leu His Gly Gly Cys Thr Val Pro Gly Glu
225                 230                 235                 240

Cys Arg Cys Ser Tyr Gly Trp Gln Gly Lys Phe Cys Asp Glu Cys Val
                245                 250                 255

Pro Tyr Pro Gly Cys Val His Gly Ser Cys Val Glu Pro Trp His Cys
            260                 265                 270

Asp Cys Glu Thr Asn Trp Gly Gly Leu Leu Cys Asp Lys Asp Leu Asn
        275                 280                 285

Tyr Cys Gly Ser His His Pro Cys Val Asn Gly Gly Thr Cys Ile Asn
    290                 295                 300

Ala Glu Pro Asp Gln Tyr Leu Cys Ala Cys Pro Asp Gly Tyr Leu Gly
305                 310                 315                 320

Lys Asn Cys Glu Arg Ala Glu His Ala Cys Ala Ser Asn Pro Cys Ala
                325                 330                 335

Asn Gly Gly Ser Cys His Glu Val Pro Ser Gly Phe Glu Cys His Cys
            340                 345                 350

Pro Ser Gly Trp Asn Gly Pro Thr Cys Ala Leu Asp Ile Asp Glu Glu
        355                 360                 365

Phe Gly Leu Val Pro Arg Gly Ser Gly His His His His His
    370                 375                 380

<210> SEQ ID NO 8
<211> LENGTH: 381
<212> TYPE: PRT
<213> ORGANISM: Artificial Sequence
<220> FEATURE:
<223> OTHER INFORMATION: Synthetic polypeptide

<400> SEQUENCE: 8

Ala Arg Pro Met Gly Tyr Phe Glu Leu Gln Leu Ser Ala Leu Arg Asn
1               5                   10                  15

Val Asn Gly Glu Leu Leu Ser Gly Ala Cys Cys Asp Gly Asp Gly Arg
            20                  25                  30

Thr Thr Arg Ala Gly Gly Cys Gly His Asp Glu Cys Asp Thr Tyr Val
        35                  40                  45

Arg Val Cys Leu Lys Glu Tyr Gln Ala Lys Val Thr Pro Thr Gly Pro
    50                  55                  60
```

```
Cys Ser Tyr Gly His Gly Ala Thr Pro Val Leu Gly Asn Ser Phe
 65                  70                  75                  80

Tyr Leu Pro Pro Ala Gly Ala Ala Gly Asp Arg Ala Arg Ala Arg Ala
                 85                  90                  95

Arg Ala Gly Gly Asp Gln Asp Pro Gly Leu Val Val Ile Pro Phe Gln
            100                 105                 110

Phe Ala Trp Pro Arg Ser Phe Thr Leu Ile Val Glu Ala Trp Asp Trp
            115                 120                 125

Asp Asn Asp Thr Thr Pro Asn Glu Glu Leu Leu Ile Glu Arg Val Ser
130                 135                 140

His Ala Gly Met Ile Asn Pro Glu Asp Arg Trp Lys Ser Leu His Phe
145                 150                 155                 160

Ser Gly His Val Ala His Leu Glu Leu Gln Ile Arg Val Arg Cys Asp
                165                 170                 175

Glu Asn Tyr Tyr Ser Ala Thr Cys Asn Lys Phe Cys Arg Pro Arg Asn
            180                 185                 190

Asp Phe Phe Gly His Tyr Thr Cys Asp Gln Tyr Gly Asn Lys Ala Cys
            195                 200                 205

Met Asp Gly Trp Met Gly Lys Glu Cys Lys Glu Ala Val Cys Lys Gln
210                 215                 220

Gly Cys Asn Leu Leu His Gly Gly Cys Thr Val Pro Gly Glu Cys Arg
225                 230                 235                 240

Cys Ser Tyr Gly Trp Gln Gly Arg Phe Cys Asp Glu Cys Val Pro Tyr
                245                 250                 255

Pro Gly Cys Val His Gly Ser Cys Val Glu Pro Trp Gln Cys Asn Cys
            260                 265                 270

Glu Thr Asn Trp Gly Gly Leu Leu Cys Asp Lys Asp Leu Asn Tyr Cys
            275                 280                 285

Gly Ser His His Pro Cys Thr Asn Gly Gly Thr Cys Ile Asn Ala Glu
290                 295                 300

Pro Asp Gln Tyr Arg Cys Thr Cys Pro Asp Gly Tyr Ser Gly Arg Asn
305                 310                 315                 320

Cys Glu Lys Ala Glu His Ala Cys Thr Ser Asn Pro Cys Ala Asn Gly
                325                 330                 335

Gly Ser Cys His Glu Val Pro Ser Gly Phe Glu Cys His Cys Pro Ser
            340                 345                 350

Gly Trp Ser Gly Pro Thr Cys Ala Leu Asp Ile Asp Glu Cys Phe Gly
            355                 360                 365

Leu Val Pro Arg Gly Ser Gly His His His His His
370                 375                 380
```

<210> SEQ ID NO 9
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 9

```
Glu Val Gln Leu Val Glu Ser Gly Gly Gly Leu Val Gln Pro Gly Gly
  1               5                  10                  15

Ser Leu Arg Leu Ser Cys Ala Ala Ser Gly Phe Thr Phe Ser Asn Tyr
             20                  25                  30

Gly Ile His Trp Val Arg Gln Ala Pro Gly Lys Gly Leu Glu Trp Val
         35                  40                  45
```

Gly Trp Ile Thr Pro Asp Gly Gly Tyr Thr Asp Tyr Ala Asp Ser Val
            50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ala Gly Ser Trp Phe Ala Tyr Trp Gly Gln Gly Thr Leu Val
            100                 105                 110

Thr Val Ser Ser
        115

<210> SEQ ID NO 10
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 10

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Pro Asp Gly Gly Tyr Thr Asp Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ala Gly Ser Leu Phe Ala Tyr Trp Gly Gln Gly Thr Leu Val
            100                 105                 110

Thr Val Ser Ser
        115

<210> SEQ ID NO 11
<211> LENGTH: 116
<212> TYPE: PRT
<213> ORGANISM: Artificial Sequence
<220> FEATURE:
<223> OTHER INFORMATION: Synthetic polypeptide

<400> SEQUENCE: 11

Glu Val Gln Leu Val Glu Ser Gly Gly Gly Leu Val Gln Pro Gly Gly
 1               5                  10                  15

Ser Leu Arg Leu Ser Cys Ala Ala Ser Gly Phe Thr Phe Ser Asn Tyr
            20                  25                  30

Gly Ile His Trp Val Arg Gln Ala Pro Gly Lys Gly Leu Glu Trp Val
        35                  40                  45

Gly Trp Ile Thr Gly Asn Gly Gly Tyr Ser Asp Tyr Ala Asp Ser Val
    50                  55                  60

Lys Gly Arg Phe Thr Ile Ser Ala Asp Thr Ser Lys Asn Thr Ala Tyr
 65                  70                  75                  80

Leu Gln Met Asn Ser Leu Arg Ala Glu Asp Thr Ala Val Tyr Tyr Cys
                85                  90                  95

Ala Arg Ala Gly Ser Trp Phe Ala Tyr Trp Gly Gln Gly Thr Leu Val

```
                   100                 105                 110
Thr Val Ser Ser
        115

<210> SEQ ID NO 12
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 12

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Asp Ile His Trp Val Arg Gln Ala Pro Gly Lys Gly Leu Glu Trp Val
        35                  40                  45

Gly Gly Ile Ser Pro Ala Asp Gly Asp Thr Asp Tyr Ala Asn Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Asp Tyr Asp Val Arg Ser Val Gly Ser Gly Met Asp Tyr
            100                 105                 110

Trp Gly Gln Gly Thr Leu Val Thr Val Ser Ser
        115                 120

<210> SEQ ID NO 13
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 13

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Asp Ile His Trp Val Arg Gln Ala Pro Gly Lys Gly Leu Glu Trp Val
        35                  40                  45

Gly Gly Ile Ser Pro Ala Asp Gly Asp Thr Asp Tyr Ala Asn Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Asp Tyr Asp Val Arg Thr Val Gly Ser Gly Met Asp Tyr
            100                 105                 110

Trp Gly Gln Gly Thr Leu Val Thr Val Ser Ser
        115                 120

<210> SEQ ID NO 14
<211> LENGTH: 123
<212> TYPE: PRT
<213> ORGANISM: Artificial Sequence
<220> FEATURE:
```

<223> OTHER INFORMATION: Synthetic polypeptide

<400> SEQUENCE: 14

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Asp Ile His Trp Val Arg Gln Ala Pro Gly Lys Gly Leu Glu Trp Val
        35                  40                  45

Gly Gly Ile Ser Pro Ala Asp Gly Asp Thr Asp Tyr Ala Asn Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Asp Tyr Asp Val Arg Ser Val Gly Ser Gly Met Asp Tyr
            100                 105                 110

Trp Gly Gln Gly Thr Leu Val Thr Val Ser Ser
        115                 120

<210> SEQ ID NO 15
<211> LENGTH: 123
<212> TYPE: PRT
<213> ORGANISM: Artificial Sequence
<220> FEATURE:
<223> OTHER INFORMATION: Synthetic polypeptide

<400> SEQUENCE: 15

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Tyr
            20                  25                  30

Asp Ile His Trp Val Arg Gln Ala Pro Gly Lys Gly Leu Glu Trp Val
        35                  40                  45

Gly Gly Ile Ser Pro Ala Asp Gly Asp Thr Asp Tyr Ala Asn Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asn Asp Tyr Asp Val Arg Phe Val Gly Ser Gly Met Asp Tyr
            100                 105                 110

Trp Gly Gln Gly Thr Leu Val Thr Val Ser Ser
        115                 120

<210> SEQ ID NO 16
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 16

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Asn Ser
            20                  25                  30

Asp Ile His Trp Val Arg Gln Ala Pro Gly Lys Gly Leu Glu Trp Val

```
                    35                  40                  45
Gly Gly Ile Thr Pro Ala Asp Gly Tyr Thr Asp Tyr Ala Asp Ser Val
        50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Arg Ser Tyr Trp Asn Asn Ser Pro Gly Ser Gly Phe Asp Tyr Trp
                100                 105                 110
Gly Gln Gly Thr Leu Val Thr Val Ser Ser
            115                 120
```

<210> SEQ ID NO 17
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 17

```
Glu Val Gln Leu Val Glu Ser Gly Gly Gly Leu Val Gln Pro Gly Gly
 1               5                  10                  15
Ser Leu Arg Leu Ser Cys Ala Ala Ser Gly Phe Thr Phe Thr Asn Ser
                20                  25                  30
Asp Ile His Trp Val Arg Gln Ala Pro Gly Lys Gly Leu Glu Trp Val
                    35                  40                  45
Gly Gly Ile Thr Pro Ala Asp Gly Tyr Thr Asp Tyr Ala Asp Ser Val
        50                  55                  60
Lys Gly Arg Phe Thr Ile Ser Ala Asp Thr Ser Lys Asn Thr Ala Tyr
 65                  70                  75                  80
Leu Gln Met Asn Ser Leu Arg Ala Glu Asp Thr Ala Val Tyr Tyr Cys
                 85                  90                  95
Ala Arg Ser Tyr Trp Ser Ser Pro Gly Ser Ala Phe Asp Tyr Trp
                100                 105                 110
Gly Gln Gly Thr Leu Val Thr Val Ser Ser
            115                 120
```

<210> SEQ ID NO 18
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 18

```
Asp Ile Gln Met Thr Gln Ser Pro Ser Ser Leu Ser Ala Ser Val Gly
 1               5                  10                  15
Asp Arg Val Thr Ile Thr Cys Arg Ala Ser Gln Asp Val Ser Thr Ala
                20                  25                  30
Val Ala Trp Tyr Gln Gln Lys Pro Gly Lys Ala Pro Lys Leu Leu Ile
                    35                  40                  45
Tyr Ser Ala Ser Phe Leu Tyr Ser Gly Val Pro Ser Arg Phe Ser Gly
        50                  55                  60
Ser Gly Ser Gly Thr Asp Phe Thr Leu Thr Ile Ser Ser Leu Gln Pro
 65                  70                  75                  80
Glu Asp Phe Ala Thr Tyr Tyr Cys Gln Gln Ser Tyr Thr Thr Pro Pro
                 85                  90                  95
```

```
Thr Phe Gly Gln Gly Thr Lys Val Glu Ile Lys
            100                 105
```

<210> SEQ ID NO 19
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 19

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Tyr Thr Thr Ala Thr
                85                  90                  95

Thr Phe Gly Gln Gly Thr Lys Val Glu Ile Lys
            100                 105
```

<210> SEQ ID NO 20
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 20

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105
```

<210> SEQ ID NO 21
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 21

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
```

```
                    20                  25                  30

Val Ala Trp Tyr Gln Gln Lys Pro Gly Lys Ala Pro Lys Leu Leu Ile
            35                  40                  45

Tyr Ser Ala Ser Phe Leu Tyr Ser Gly Val Pro Ser Arg Phe Ser Gly
        50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Thr Pro Pro
                85                  90                  95

Thr Phe Gly Gln Gly Thr Lys Val Glu Ile Lys
            100                 105

<210> SEQ ID NO 22
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 22

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Ser Ala Pro
                85                  90                  95

Thr Phe Gly Gln Gly Thr Lys Val Glu Ile Lys
            100                 105

<210> SEQ ID NO 23
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 23

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Trp Thr Ala Pro Pro
                85                  90                  95

Thr Phe Gly Gln Gly Thr Lys Val Glu Ile Lys
            100                 105
```

<210> SEQ ID NO 24
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 24

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Phe Thr Ala Pro Pro
                85                  90                  95

Thr Phe Gly Gln Gly Thr Lys Val Glu Ile Lys
            100                 105
```

<210> SEQ ID NO 25
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 25

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
        35                  40                  45

Tyr Ser Ala Ser Phe Leu Tyr Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Ser Tyr Thr Pro Pro
                85                  90                  95

Thr Phe Gly Gln Gly Thr Lys Val Glu Ile Lys
            100                 105
```

<210> SEQ ID NO 26
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 26

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Asp Val Ser Thr Ala
            20                  25                  30

Val Ala Trp Tyr Gln Gln Lys Pro Gly Lys Ala Pro Lys Leu Leu Ile
```

```
            35                  40                  45

Tyr Ser Ala Ser Phe Leu Tyr Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Ser Tyr Ile Ser Pro Ser
                 85                  90                  95

Thr Phe Gly Gln Gly Thr Lys Val Glu Ile Lys
            100                 105
```

<210> SEQ ID NO 27
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 27

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                 20                  25                  30

Leu Ala Trp Tyr Gln Gln Lys Pro Gly Lys Ala Pro Lys Leu Leu Ile
             35                  40                  45

Tyr Gly Ala Ser Ser Arg Ala Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Tyr Ser Ser Pro Leu
                 85                  90                  95

Thr Phe Gly Gln Gly Thr Lys Val Glu Ile Lys
            100                 105
```

<210> SEQ ID NO 28
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 28

```
Asp Ile Gln Met Thr Gln Ser Pro Ser Ser Leu Ser Ala Ser Val Gly
 1               5                  10                  15

Asp Arg Val Thr Ile Thr Cys Arg Ala Ser Gln Ser Ile Ser Ser Tyr
                 20                  25                  30

Leu Ala Trp Tyr Gln Gln Lys Pro Gly Lys Ala Pro Lys Leu Leu Ile
             35                  40                  45

Tyr Gly Ala Ser Ser Arg Ala Ser Gly Val Pro Ser Arg Phe Ser Gly
     50                  55                  60

Ser Gly Ser Gly Thr Asp Phe Thr Leu Thr Ile Ser Ser Leu Gln Pro
 65                  70                  75                  80

Glu Asp Phe Ala Thr Tyr Tyr Cys Gln Gln Tyr Leu Ser Ser Pro Ile
                 85                  90                  95

Thr Phe Gly Gln Gly Thr Lys Val Glu Ile Lys
            100                 105
```

<210> SEQ ID NO 29
<211> LENGTH: 122

<212> TYPE: PRT
<213> ORGANISM: Artificial Sequence
<220> FEATURE:
<223> OTHER INFORMATION: Synthetic polypeptide

<400> SEQUENCE: 29

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Asn
            20                  25                  30

Tyr Met Ser Trp Val Arg Gln Ala Pro Gly Lys Gly Leu Glu Trp Val
        35                  40                  45

Ser Thr Ile Trp Tyr Gln Ser Gly Thr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Pro Trp Ser Gly Glu Gly Phe Gly Met Asp Val Trp
            100                 105                 110

Gly Gln Gly Thr Leu Val Thr Val Ser Ser
        115                 120

<210> SEQ ID NO 30
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 30

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Thr Ser Asn
            20                  25                  30

Tyr Met Ser Trp Val Arg Gln Ala Pro Gly Lys Gly Leu Glu Trp Val
        35                  40                  45

Ser Thr Ile Trp Tyr Gln Ser Gly Thr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Asp Ser Pro Trp Pro Ser Lys Gly Phe Gly Met Asp Val Trp
            100                 105                 110

Gly Gln Gly Thr Leu Val Thr Val Ser Ser
        115                 120

<210> SEQ ID NO 31
<211> LENGTH: 5
<212> TYPE: PRT
<213> ORGANISM: Artificial Sequence
<220> FEATURE:
<223> OTHER INFORMATION: Synthetic peptide

<400> SEQUENCE: 31

Ala Asp Leu Gly Ser
1               5

```
<210> SEQ ID NO 32
<211> LENGTH: 30
<212> TYPE: PRT
<213> ORGANISM: Homo sapiens

<400> SEQUENCE: 32

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr
            20                  25                  30

<210> SEQ ID NO 33
<211> LENGTH: 14
<212> TYPE: PRT
<213> ORGANISM: Homo sapiens

<400> SEQUENCE: 33

Trp Val Arg Gln Ala Pro Gly Gln Gly Leu Glu Trp Met Gly
1               5                   10

<210> SEQ ID NO 34
<211> LENGTH: 32
<212> TYPE: PRT
<213> ORGANISM: Homo sapiens

<400> SEQUENCE: 34

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala Arg
            20                  25                  30

<210> SEQ ID NO 35
<211> LENGTH: 11
<212> TYPE: PRT
<213> ORGANISM: Homo sapiens

<400> SEQUENCE: 35

Trp Gly Gln Gly Thr Leu Val Thr Val Ser Ser
1               5                   10

<210> SEQ ID NO 36
<211> LENGTH: 25
<212> TYPE: PRT
<213> ORGANISM: Homo sapiens

<400> SEQUENCE: 36

Gln Val Gln Leu Val Gln Ser Gly Ala Glu Val Lys Lys Pro Gly Ala
1               5                   10                  15

Ser Val Lys Val Ser Cys Lys Ala Ser
            20                  25

<210> SEQ ID NO 37
<211> LENGTH: 13
<212> TYPE: PRT
<213> ORGANISM: Homo sapiens

<400> SEQUENCE: 37

Trp Val Arg Gln Ala Pro Gly Gln Gly Leu Glu Trp Met
1               5                   10

<210> SEQ ID NO 38
<211> LENGTH: 31
<212> TYPE: PRT
<213> ORGANISM: Homo sapiens
```

```
<400> SEQUENCE: 38

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys Ala
            20                  25                  30

<210> SEQ ID NO 39
<211> LENGTH: 30
<212> TYPE: PRT
<213> ORGANISM: Homo sapiens

<400> SEQUENCE: 39

Arg Val Thr Ile Thr Ala Asp Thr Ser Thr Ser Thr Ala Tyr Met Glu
1               5                   10                  15

Leu Ser Ser Leu Arg Ser Glu Asp Thr Ala Val Tyr Tyr Cys
            20                  25                  30

<210> SEQ ID NO 40
<211> LENGTH: 30
<212> TYPE: PRT
<213> ORGANISM: Homo sapiens

<400> SEQUENCE: 40

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Val Ser
            20                  25                  30

<210> SEQ ID NO 41
<211> LENGTH: 14
<212> TYPE: PRT
<213> ORGANISM: Homo sapiens

<400> SEQUENCE: 41

Trp Ile Arg Gln Pro Pro Gly Lys Gly Leu Glu Trp Ile Gly
1               5                   10

<210> SEQ ID NO 42
<211> LENGTH: 32
<212> TYPE: PRT
<213> ORGANISM: Homo sapiens

<400> SEQUENCE: 42

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala Arg
            20                  25                  30

<210> SEQ ID NO 43
<211> LENGTH: 25
<212> TYPE: PRT
<213> ORGANISM: Homo sapiens

<400> SEQUENCE: 43

Gln Val Gln Leu Gln Glu Ser Gly Pro Gly Leu Val Lys Pro Ser Gln
1               5                   10                  15

Thr Leu Ser Leu Thr Cys Thr Val Ser
            20                  25

<210> SEQ ID NO 44
<211> LENGTH: 13
```

<212> TYPE: PRT
<213> ORGANISM: Homo sapiens

<400> SEQUENCE: 44

Trp Ile Arg Gln Pro Pro Gly Lys Gly Leu Glu Trp Ile
1               5                   10

<210> SEQ ID NO 45
<211> LENGTH: 31
<212> TYPE: PRT
<213> ORGANISM: Homo sapiens

<400> SEQUENCE: 45

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys Ala
            20                  25                  30

<210> SEQ ID NO 46
<211> LENGTH: 30
<212> TYPE: PRT
<213> ORGANISM: Homo sapiens

<400> SEQUENCE: 46

Arg Val Thr Ile Ser Val Asp Thr Ser Lys Asn Gln Phe Ser Leu Lys
1               5                   10                  15

Leu Ser Ser Val Thr Ala Ala Asp Thr Ala Val Tyr Tyr Cys
            20                  25                  30

<210> SEQ ID NO 47
<211> LENGTH: 30
<212> TYPE: PRT
<213> ORGANISM: Homo sapiens

<400> SEQUENCE: 47

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ser
            20                  25                  30

<210> SEQ ID NO 48
<211> LENGTH: 14
<212> TYPE: PRT
<213> ORGANISM: Homo sapiens

<400> SEQUENCE: 48

Trp Val Arg Gln Ala Pro Gly Lys Gly Leu Glu Trp Val Ser
1               5                   10

<210> SEQ ID NO 49
<211> LENGTH: 32
<212> TYPE: PRT
<213> ORGANISM: Homo sapiens

<400> SEQUENCE: 49

Arg Phe Thr Ile Ser Arg Asp Asn Ser Lys Asn Thr Leu Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 50
<211> LENGTH: 25
<212> TYPE: PRT

-continued

<213> ORGANISM: Homo sapiens

<400> SEQUENCE: 50

Glu Val Gln Leu Val Glu Ser Gly Gly Gly Leu Val Gln Pro Gly Gly
1               5                   10                  15
Ser Leu Arg Leu Ser Cys Ala Ala Ser
            20                  25

<210> SEQ ID NO 51
<211> LENGTH: 13
<212> TYPE: PRT
<213> ORGANISM: Homo sapiens

<400> SEQUENCE: 51

Trp Val Arg Gln Ala Pro Gly Lys Gly Leu Glu Trp Val
1               5                   10

<210> SEQ ID NO 52
<211> LENGTH: 31
<212> TYPE: PRT
<213> ORGANISM: Homo sapiens

<400> SEQUENCE: 52

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys Ala
            20                  25                  30

<210> SEQ ID NO 53
<211> LENGTH: 30
<212> TYPE: PRT
<213> ORGANISM: Homo sapiens

<400> SEQUENCE: 53

Arg Phe Thr Ile Ser Arg Asp Asn Ser Lys Asn Thr Leu Tyr Leu Gln
1               5                   10                  15
Met Asn Ser Leu Arg Ala Glu Asp Thr Ala Val Tyr Tyr Cys
            20                  25                  30

<210> SEQ ID NO 54
<211> LENGTH: 30
<212> TYPE: PRT
<213> ORGANISM: Homo sapiens

<400> SEQUENCE: 54

Glu Val Gln Leu Val Glu Ser Gly Gly Gly Leu Val Gln Pro Gly Gly
1               5                   10                  15
Ser Leu Arg Leu Ser Cys Ala Ala Ser Gly Phe Asn Ile Lys
            20                  25                  30

<210> SEQ ID NO 55
<211> LENGTH: 32
<212> TYPE: PRT
<213> ORGANISM: Homo sapiens

<400> SEQUENCE: 55

Arg Phe Thr Ile Ser Ala Asp Thr Ser Lys Asn Thr Ala Tyr Leu Gln
1               5                   10                  15
Met Asn Ser Leu Arg Ala Glu Asp Thr Ala Val Tyr Tyr Cys Ser Arg
            20                  25                  30

<210> SEQ ID NO 56

<211> LENGTH: 31
<212> TYPE: PRT
<213> ORGANISM: Homo sapiens

<400> SEQUENCE: 56

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ser
            20                  25                  30

<210> SEQ ID NO 57
<211> LENGTH: 32
<212> TYPE: PRT
<213> ORGANISM: Homo sapiens

<400> SEQUENCE: 57

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala Arg
            20                  25                  30

<210> SEQ ID NO 58
<211> LENGTH: 31
<212> TYPE: PRT
<213> ORGANISM: Homo sapiens

<400> SEQUENCE: 58

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys Ala
            20                  25                  30

<210> SEQ ID NO 59
<211> LENGTH: 30
<212> TYPE: PRT
<213> ORGANISM: Homo sapiens

<400> SEQUENCE: 59

Arg Phe Thr Ile Ser Ala Asp Thr Ser Lys Asn Thr Ala Tyr Leu Gln
1               5                   10                  15

Met Asn Ser Leu Arg Ala Glu Asp Thr Ala Val Tyr Tyr Cys
            20                  25                  30

<210> SEQ ID NO 60
<211> LENGTH: 23
<212> TYPE: PRT
<213> ORGANISM: Homo sapiens

<400> SEQUENCE: 60

Asp Ile Gln Met Thr Gln Ser Pro Ser Ser Leu Ser Ala Ser Val Gly
1               5                   10                  15

Asp Arg Val Thr Ile Thr Cys
            20

<210> SEQ ID NO 61
<211> LENGTH: 15
<212> TYPE: PRT
<213> ORGANISM: Homo sapiens

<400> SEQUENCE: 61

Trp Tyr Gln Gln Lys Pro Gly Lys Ala Pro Lys Leu Leu Ile Tyr
1               5                   10                  15

<210> SEQ ID NO 62
<211> LENGTH: 32
<212> TYPE: PRT
<213> ORGANISM: Homo sapiens

<400> SEQUENCE: 62

Gly Val Pro Ser Arg Phe Ser Gly Ser Gly Ser Gly Thr Asp Phe Thr
1               5                   10                  15

Leu Thr Ile Ser Ser Leu Gln Pro Glu Asp Phe Ala Thr Tyr Tyr Cys
            20                  25                  30

<210> SEQ ID NO 63
<211> LENGTH: 10
<212> TYPE: PRT
<213> ORGANISM: Homo sapiens

<400> SEQUENCE: 63

Phe Gly Gln Gly Thr Lys Val Glu Ile Lys
1               5                   10

<210> SEQ ID NO 64
<211> LENGTH: 23
<212> TYPE: PRT
<213> ORGANISM: Homo sapiens

<400> SEQUENCE: 64

Asp Ile Val Met Thr Gln Ser Pro Leu Ser Leu Pro Val Thr Pro Gly
1               5                   10                  15

Glu Pro Ala Ser Ile Ser Cys
            20

<210> SEQ ID NO 65
<211> LENGTH: 15
<212> TYPE: PRT
<213> ORGANISM: Homo sapiens

<400> SEQUENCE: 65

Trp Tyr Leu Gln Lys Pro Gly Gln Ser Pro Gln Leu Leu Ile Tyr
1               5                   10                  15

<210> SEQ ID NO 66
<211> LENGTH: 32
<212> TYPE: PRT
<213> ORGANISM: Homo sapiens

<400> SEQUENCE: 66

Gly Val Pro Asp Arg Phe Ser Gly Ser Gly Ser Gly Thr Asp Phe Thr
1               5                   10                  15

Leu Lys Ile Ser Arg Val Glu Ala Glu Asp Val Gly Val Tyr Tyr Cys
            20                  25                  30

<210> SEQ ID NO 67
<211> LENGTH: 23
<212> TYPE: PRT
<213> ORGANISM: Homo sapiens

<400> SEQUENCE: 67

Glu Ile Val Leu Thr Gln Ser Pro Gly Thr Leu Ser Leu Ser Pro Gly
1               5                   10                  15

Glu Arg Ala Thr Leu Ser Cys
            20

```
<210> SEQ ID NO 68
<211> LENGTH: 15
<212> TYPE: PRT
<213> ORGANISM: Homo sapiens

<400> SEQUENCE: 68

Trp Tyr Gln Gln Lys Pro Gly Gln Ala Pro Arg Leu Leu Ile Tyr
1               5                   10                  15

<210> SEQ ID NO 69
<211> LENGTH: 32
<212> TYPE: PRT
<213> ORGANISM: Homo sapiens

<400> SEQUENCE: 69

Gly Ile Pro Asp Arg Phe Ser Gly Ser Gly Ser Gly Thr Asp Phe Thr
1               5                   10                  15

Leu Thr Ile Ser Arg Leu Glu Pro Glu Asp Phe Ala Val Tyr Tyr Cys
            20                  25                  30

<210> SEQ ID NO 70
<211> LENGTH: 23
<212> TYPE: PRT
<213> ORGANISM: Homo sapiens

<400> SEQUENCE: 70

Asp Ile Val Met Thr Gln Ser Pro Asp Ser Leu Ala Val Ser Leu Gly
1               5                   10                  15

Glu Arg Ala Thr Ile Asn Cys
            20

<210> SEQ ID NO 71
<211> LENGTH: 15
<212> TYPE: PRT
<213> ORGANISM: Homo sapiens

<400> SEQUENCE: 71

Trp Tyr Gln Gln Lys Pro Gly Gln Pro Pro Lys Leu Leu Ile Tyr
1               5                   10                  15

<210> SEQ ID NO 72
<211> LENGTH: 32
<212> TYPE: PRT
<213> ORGANISM: Homo sapiens

<400> SEQUENCE: 72

Gly Val Pro Asp Arg Phe Ser Gly Ser Gly Ser Gly Thr Asp Phe Thr
1               5                   10                  15

Leu Thr Ile Ser Ser Leu Gln Ala Glu Asp Val Ala Val Tyr Tyr Cys
            20                  25                  30

<210> SEQ ID NO 73
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 73

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Ser Val Lys Pro Met
            20                  25                  30
```

```
Tyr Met Thr Trp Val Arg Gln Ala Pro Gly Lys Gly Leu Glu Trp Val
            35                  40                  45

Ser Thr Ile Trp Tyr Gln Ser Gly Thr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Pro Trp Ser Gly Glu Gly Phe Gly Met Asp Val Trp
                100                 105                 110

Gly Gln Gly Thr Leu Val Thr Val Ser Ser
            115                 120

<210> SEQ ID NO 74
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 74

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Phe Ile Ser Asn
                20                  25                  30

Tyr Val Ser Trp Val Arg Gln Ala Pro Gly Lys Gly Leu Glu Trp Val
            35                  40                  45

Ser Thr Ile Trp Tyr Gln Ser Gly Thr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Pro Trp Ser Gly Glu Gly Phe Gly Met Asp Val Trp
                100                 105                 110

Gly Gln Gly Thr Leu Val Thr Val Ser Ser
            115                 120

<210> SEQ ID NO 75
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 75

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Thr Pro Leu
                20                  25                  30

Tyr Met Ser Trp Val Arg Gln Ala Pro Gly Lys Gly Leu Glu Trp Val
            35                  40                  45

Ser Thr Ile Trp Tyr Gln Ser Gly Thr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95
```

Ala Arg Ser Ser Pro Trp Ser Gly Glu Gly Phe Gly Met Asp Val Trp
            100                 105                 110

Gly Gln Gly Thr Leu Val Thr Val Ser Ser
        115                 120

<210> SEQ ID NO 76
<211> LENGTH: 122
<212> TYPE: PRT
<213> ORGANISM: Artificial Sequence
<220> FEATURE:
<223> OTHER INFORMATION: Synthetic polypeptide

<400> SEQUENCE: 76

Glu Val Gln Leu Val Glu Ser Gly Gly Gly Leu Val Gln Pro Gly Gly
1               5                   10                  15

Ser Leu Arg Leu Ser Cys Ala Ala Ser Gly Phe Thr Val Thr Pro Met
            20                  25                  30

Tyr Met Ser Trp Val Arg Gln Ala Pro Gly Lys Gly Leu Glu Trp Val
        35                  40                  45

Ser Thr Ile Trp Tyr Gln Ser Gly Thr Thr Asp Tyr Ala Asp Ser Val
    50                  55                  60

Lys Gly Arg Phe Thr Ile Ser Ala Asp Thr Ser Lys Asn Thr Ala Tyr
65                  70                  75                  80

Leu Gln Met Asn Ser Leu Arg Ala Glu Asp Thr Ala Val Tyr Tyr Cys
                85                  90                  95

Ala Arg Ser Ser Pro Trp Ser Gly Glu Gly Phe Gly Met Asp Val Trp
            100                 105                 110

Gly Gln Gly Thr Leu Val Thr Val Ser Ser
        115                 120

<210> SEQ ID NO 77
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 77

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Ser Pro Leu
                85                  90                  95

Thr Phe Gly Gln Gly Thr Lys Val Glu Ile Lys
            100                 105

<210> SEQ ID NO 78
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 78

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr His Ser Ser Pro Leu
                85                  90                  95

Thr Phe Gly Gln Gly Thr Lys Val Glu Ile Lys
            100                 105

<210> SEQ ID NO 79
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 79

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Gln Gln Tyr Ser Ser Ser Pro Leu
                85                  90                  95

Thr Phe Gly Gln Gly Thr Lys Val Glu Ile Lys
            100                 105

<210> SEQ ID NO 80
<211> LENGTH: 107
<212> TYPE: PRT
<213> ORGANISM: Artificial Sequence
<220> FEATURE:
<223> OTHER INFORMATION: Synthetic polypeptide

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Ser Ile Ser Ser Tyr
            20                  25                  30

Leu Ala Trp Tyr Gln Gln Lys Pro Gly Lys Ala Pro Lys Leu Leu Ile
        35                  40                  45

Tyr Gly Ala Ser Ser Arg Ala Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

```
Glu Asp Phe Ala Thr Tyr Tyr Cys Gln Gln Tyr Ser Ser Ser Pro Leu
                85                  90                  95

Thr Phe Gly Gln Gly Thr Lys Val Glu Ile Lys
            100                 105

<210> SEQ ID NO 81
<211> LENGTH: 10
<212> TYPE: PRT
<213> ORGANISM: Artificial Sequence
<220> FEATURE:
<223> OTHER INFORMATION: Synthetic peptide

<400> SEQUENCE: 81

Gly Phe Thr Phe Ser Asn Tyr Gly Ile His
1               5                   10

<210> SEQ ID NO 82
<211> LENGTH: 17
<212> TYPE: PRT
<213> ORGANISM: Artificial Sequence
<220> FEATURE:
<223> OTHER INFORMATION: Synthetic peptide

<400> SEQUENCE: 82

Trp Ile Thr Pro Asp Gly Gly Tyr Thr Asp Tyr Ala Asp Ser Val Lys
1               5                   10                  15

Gly

<210> SEQ ID NO 83
<211> LENGTH: 17
<212> TYPE: PRT
<213> ORGANISM: Artificial Sequence
<220> FEATURE:
<223> OTHER INFORMATION: Synthetic peptide

<400> SEQUENCE: 83

Trp Ile Thr Gly Asn Gly Gly Tyr Ser Asp Tyr Ala Asp Ser Val Lys
1               5                   10                  15

Gly

<210> SEQ ID NO 84
<211> LENGTH: 17
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(17)
<223> OTHER INFORMATION: Variant residues given in the sequence have no
      preference with respect to those in the annotations for variant
      positions
<220> FEATURE:
<221> NAME/KEY: VARIANT
<222> LOCATION: (4)..(4)
<223> OTHER INFORMATION: Pro or Gly
<220> FEATURE:
<221> NAME/KEY: VARIANT
<222> LOCATION: (5)..(5)
<223> OTHER INFORMATION: Asp or Asn
<220> FEATURE:
<221> NAME/KEY: VARIANT
<222> LOCATION: (9)..(9)
<223> OTHER INFORMATION: Thr or Ser

<400> SEQUENCE: 84

Trp Ile Thr Xaa Xaa Gly Gly Tyr Xaa Asp Tyr Ala Asp Ser Val Lys
```

```
                 1               5                  10                 15

Gly

<210> SEQ ID NO 85
<211> LENGTH: 7
<212> TYPE: PRT
<213> ORGANISM: Artificial Sequence
<220> FEATURE:
<223> OTHER INFORMATION: Synthetic peptide

<400> SEQUENCE: 85

Ala Gly Ser Trp Phe Ala Tyr
1               5

<210> SEQ ID NO 86
<211> LENGTH: 7
<212> TYPE: PRT
<213> ORGANISM: Artificial Sequence
<220> FEATURE:
<223> OTHER INFORMATION: Synthetic peptide

<400> SEQUENCE: 86

Ala Gly Ser Leu Phe Ala Tyr
1               5

<210> SEQ ID NO 87
<211> LENGTH: 7
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(7)
<223> OTHER INFORMATION: Variant residues given in the sequence have no
      preference with respect to those in the annotations for variant
      positions
<220> FEATURE:
<221> NAME/KEY: VARIANT
<222> LOCATION: (4)..(4)
<223> OTHER INFORMATION: Trp or Leu

<400> SEQUENCE: 87

Ala Gly Ser Xaa Phe Ala Tyr
1               5

<210> SEQ ID NO 88
<211> LENGTH: 10
<212> TYPE: PRT
<213> ORGANISM: Artificial Sequence
<220> FEATURE:
<223> OTHER INFORMATION: Synthetic peptide

<400> SEQUENCE: 88

Gly Phe Thr Phe Thr Ser Tyr Asp Ile His
1               5                  10

<210> SEQ ID NO 89
<211> LENGTH: 17
<212> TYPE: PRT
<213> ORGANISM: Artificial Sequence
<220> FEATURE:
<223> OTHER INFORMATION: Synthetic peptide

<400> SEQUENCE: 89

Gly Ile Ser Pro Ala Asp Gly Asp Thr Asp Tyr Ala Asn Ser Val Lys
1               5                  10                 15
```

Gly

<210> SEQ ID NO 90
<211> LENGTH: 14
<212> TYPE: PRT
<213> ORGANISM: Artificial Sequence
<220> FEATURE:
<223> OTHER INFORMATION: Synthetic peptide

<400> SEQUENCE: 90

Asn Asp Tyr Asp Val Arg Ser Val Gly Ser Gly Met Asp Tyr
1               5                   10

<210> SEQ ID NO 91
<211> LENGTH: 14
<212> TYPE: PRT
<213> ORGANISM: Artificial Sequence
<220> FEATURE:
<223> OTHER INFORMATION: Synthetic peptide

<400> SEQUENCE: 91

Asn Asp Tyr Asp Val Arg Thr Val Gly Ser Gly Met Asp Tyr
1               5                   10

<210> SEQ ID NO 92
<211> LENGTH: 14
<212> TYPE: PRT
<213> ORGANISM: Artificial Sequence
<220> FEATURE:
<223> OTHER INFORMATION: Synthetic peptide

<400> SEQUENCE: 92

Asn Asp Tyr Asp Val Arg Phe Val Gly Ser Gly Met Asp Tyr
1               5                   10

<210> SEQ ID NO 93
<211> LENGTH: 14
<212> TYPE: PRT
<213> ORGANISM: Artificial Sequence
<220> FEATURE:
<223> OTHER INFORMATION: Synthetic peptide

<400> SEQUENCE: 93

Asn Asp Tyr Asp Val Arg Tyr Phe Gly Ser Gly Met Asp Tyr
1               5                   10

<210> SEQ ID NO 94
<211> LENGTH: 14
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(14)
<223> OTHER INFORMATION: Variant residues given in the sequence have no
      preference with respect to those in the annotations for variant
      positions
<220> FEATURE:
<221> NAME/KEY: VARIANT
<222> LOCATION: (7)..(7)
<223> OTHER INFORMATION: Ser or Thr or Phe or Tyr
<220> FEATURE:
<221> NAME/KEY: VARIANT
<222> LOCATION: (8)..(8)
<223> OTHER INFORMATION: Val or Phe

<400> SEQUENCE: 94

Asn Asp Tyr Asp Val Arg Xaa Xaa Gly Ser Gly Met Asp Tyr

```
<210> SEQ ID NO 95
<211> LENGTH: 10
<212> TYPE: PRT
<213> ORGANISM: Artificial Sequence
<220> FEATURE:
<223> OTHER INFORMATION: Synthetic peptide

<400> SEQUENCE: 95

Gly Phe Thr Phe Thr Asn Ser Asp Ile His
1               5                   10

<210> SEQ ID NO 96
<211> LENGTH: 17
<212> TYPE: PRT
<213> ORGANISM: Artificial Sequence
<220> FEATURE:
<223> OTHER INFORMATION: Synthetic peptide

<400> SEQUENCE: 96

Gly Phe Thr Phe Ala Asp Gly Tyr Thr Asp Tyr Ala Asp Ser Val Lys
1               5                   10                  15

Gly

<210> SEQ ID NO 97
<211> LENGTH: 13
<212> TYPE: PRT
<213> ORGANISM: Artificial Sequence
<220> FEATURE:
<223> OTHER INFORMATION: Synthetic peptide

<400> SEQUENCE: 97

Ser Tyr Trp Asn Asn Ser Pro Gly Ser Gly Phe Asp Tyr
1               5                   10

<210> SEQ ID NO 98
<211> LENGTH: 13
<212> TYPE: PRT
<213> ORGANISM: Artificial Sequence
<220> FEATURE:
<223> OTHER INFORMATION: Synthetic peptide

<400> SEQUENCE: 98

Ser Tyr Trp Ser Ser Ser Pro Gly Ser Ala Phe Asp Tyr
1               5                   10

<210> SEQ ID NO 99
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(13)
<223> OTHER INFORMATION: Variant residues given in the sequence have no
      preference with respect to those in the annotations for variant
      positions
<220> FEATURE:
<221> NAME/KEY: VARIANT
<222> LOCATION: (4)..(5)
<223> OTHER INFORMATION: Asn or Ser
<220> FEATURE:
<221> NAME/KEY: VARIANT
<222> LOCATION: (10)..(10)
<223> OTHER INFORMATION: Gly or Ala

<400> SEQUENCE: 99
```

```
Ser Tyr Trp Xaa Xaa Ser Pro Gly Ser Xaa Phe Asp Tyr
1               5                   10
```

<210> SEQ ID NO 100
<211> LENGTH: 10
<212> TYPE: PRT
<213> ORGANISM: Artificial Sequence
<220> FEATURE:
<223> OTHER INFORMATION: Synthetic peptide

<400> SEQUENCE: 100

```
Gly Phe Thr Phe Thr Ser Asn Tyr Met Ser
1               5                   10
```

<210> SEQ ID NO 101
<211> LENGTH: 10
<212> TYPE: PRT
<213> ORGANISM: Artificial Sequence
<220> FEATURE:
<223> OTHER INFORMATION: Synthetic peptide

<400> SEQUENCE: 101

```
Gly Phe Ser Val Lys Pro Met Tyr Met Thr
1               5                   10
```

<210> SEQ ID NO 102
<211> LENGTH: 10
<212> TYPE: PRT
<213> ORGANISM: Artificial Sequence
<220> FEATURE:
<223> OTHER INFORMATION: Synthetic peptide

<400> SEQUENCE: 102

```
Gly Phe Thr Phe Ile Ser Asn Tyr Val Ser
1               5                   10
```

<210> SEQ ID NO 103
<211> LENGTH: 10
<212> TYPE: PRT
<213> ORGANISM: Artificial Sequence
<220> FEATURE:
<223> OTHER INFORMATION: Synthetic peptide

<400> SEQUENCE: 103

```
Gly Phe Thr Val Thr Pro Leu Tyr Met Ser
1               5                   10
```

<210> SEQ ID NO 104
<211> LENGTH: 10
<212> TYPE: PRT
<213> ORGANISM: Artificial Sequence
<220> FEATURE:
<223> OTHER INFORMATION: Synthetic peptide

<400> SEQUENCE: 104

```
Gly Phe Thr Val Thr Pro Met Tyr Met Ser
1               5                   10
```

<210> SEQ ID NO 105
<211> LENGTH: 10
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(10)

```
<223> OTHER INFORMATION: Variant residues given in the sequence have no
      preference with respect to those in the annotations for variant
      positions
<220> FEATURE:
<221> NAME/KEY: VARIANT
<222> LOCATION: (3)..(3)
<223> OTHER INFORMATION: Thr or Ser
<220> FEATURE:
<221> NAME/KEY: VARIANT
<222> LOCATION: (4)..(4)
<223> OTHER INFORMATION: Phe or Val
<220> FEATURE:
<221> NAME/KEY: VARIANT
<222> LOCATION: (5)..(5)
<223> OTHER INFORMATION: Thr or Lys or Ile
<220> FEATURE:
<221> NAME/KEY: VARIANT
<222> LOCATION: (6)..(6)
<223> OTHER INFORMATION: Ser or Pro
<220> FEATURE:
<221> NAME/KEY: VARIANT
<222> LOCATION: (7)..(7)
<223> OTHER INFORMATION: Asn or Met or Leu
<220> FEATURE:
<221> NAME/KEY: VARIANT
<222> LOCATION: (9)..(9)
<223> OTHER INFORMATION: Met or Val
<220> FEATURE:
<221> NAME/KEY: VARIANT
<222> LOCATION: (10)..(10)
<223> OTHER INFORMATION: Ser or Thr

<400> SEQUENCE: 105

Gly Phe Xaa Xaa Xaa Xaa Xaa Tyr Xaa Xaa
1               5                   10

<210> SEQ ID NO 106
<211> LENGTH: 17
<212> TYPE: PRT
<213> ORGANISM: Artificial Sequence
<220> FEATURE:
<223> OTHER INFORMATION: Synthetic peptide

<400> SEQUENCE: 106

Thr Ile Trp Tyr Gln Ser Gly Thr Thr Asp Tyr Ala Asp Ser Val Lys
1               5                   10                  15

Gly

<210> SEQ ID NO 107
<211> LENGTH: 13
<212> TYPE: PRT
<213> ORGANISM: Artificial Sequence
<220> FEATURE:
<223> OTHER INFORMATION: Synthetic peptide

<400> SEQUENCE: 107

Ser Ser Pro Trp Ser Gly Glu Gly Phe Gly Met Asp Val
1               5                   10

<210> SEQ ID NO 108
<211> LENGTH: 13
<212> TYPE: PRT
<213> ORGANISM: Artificial Sequence
<220> FEATURE:
<223> OTHER INFORMATION: Synthetic peptide

<400> SEQUENCE: 108

Asp Ser Pro Trp Pro Ser Lys Gly Phe Gly Met Asp Val
1               5                   10
```

```
<210> SEQ ID NO 109
<211> LENGTH: 13
<212> TYPE: PRT
<213> ORGANISM: Artificial Sequence
<220> FEATURE:
<223> OTHER INFORMATION: Synthetic peptide
<220> FEATURE:
<221> NAME/KEY: VARIANT
<222> LOCATION: (1)..(1)
<223> OTHER INFORMATION: Ser or Asp
<220> FEATURE:
<221> NAME/KEY: misc_feature
<222> LOCATION: (1)..(13)
<223> OTHER INFORMATION: Variant residues given in the sequence have no
      preference with respect to those in the annotations for variant
      positions
<220> FEATURE:
<221> NAME/KEY: VARIANT
<222> LOCATION: (5)..(5)
<223> OTHER INFORMATION: Ser or Pro
<220> FEATURE:
<221> NAME/KEY: VARIANT
<222> LOCATION: (6)..(6)
<223> OTHER INFORMATION: Gly or Ser
<220> FEATURE:
<221> NAME/KEY: VARIANT
<222> LOCATION: (7)..(7)
<223> OTHER INFORMATION: Glu or Lys

<400> SEQUENCE: 109

Xaa Ser Pro Trp Xaa Xaa Xaa Gly Phe Gly Met Asp Val
1               5                   10

<210> SEQ ID NO 110
<211> LENGTH: 11
<212> TYPE: PRT
<213> ORGANISM: Artificial Sequence
<220> FEATURE:
<223> OTHER INFORMATION: Synthetic peptide

<400> SEQUENCE: 110

Arg Ala Ser Gln Asp Val Ser Thr Ala Val Ala
1               5                   10

<210> SEQ ID NO 111
<211> LENGTH: 7
<212> TYPE: PRT
<213> ORGANISM: Artificial Sequence
<220> FEATURE:
<223> OTHER INFORMATION: Synthetic peptide

<400> SEQUENCE: 111

Ser Ala Ser Phe Leu Tyr Ser
1               5

<210> SEQ ID NO 112
<211> LENGTH: 9
<212> TYPE: PRT
<213> ORGANISM: Artificial Sequence
<220> FEATURE:
<223> OTHER INFORMATION: Synthetic peptide

<400> SEQUENCE: 112

Gln Gln Ser Tyr Thr Thr Pro Pro Thr
1               5

<210> SEQ ID NO 113
<211> LENGTH: 9
<212> TYPE: PRT
<213> ORGANISM: Artificial Sequence
<220> FEATURE:
```

```
<223> OTHER INFORMATION: Synthetic peptide

<400> SEQUENCE: 113

Gln Gln Tyr Tyr Thr Thr Ala Thr Thr
1               5

<210> SEQ ID NO 114
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(9)
<223> OTHER INFORMATION: Variant residues given in the sequence have no
      preference with respect to those in the annotations for variant
      positions
<220> FEATURE:
<221> NAME/KEY: VARIANT
<222> LOCATION: (3)..(3)
<223> OTHER INFORMATION: Ser or Tyr
<220> FEATURE:
<221> NAME/KEY: VARIANT
<222> LOCATION: (7)..(7)
<223> OTHER INFORMATION: Pro or Ala
<220> FEATURE:
<221> NAME/KEY: VARIANT
<222> LOCATION: (8)..(8)
<223> OTHER INFORMATION: Pro or Thr

<400> SEQUENCE: 114

Gln Gln Xaa Tyr Thr Thr Xaa Xaa Thr
1               5

<210> SEQ ID NO 115
<211> LENGTH: 11
<212> TYPE: PRT
<213> ORGANISM: Artificial Sequence
<220> FEATURE:
<223> OTHER INFORMATION: Synthetic peptide

<400> SEQUENCE: 115

Arg Ala Ser Gln Asp Val Ser Thr Ala Val Ala
1               5                   10

<210> SEQ ID NO 116
<211> LENGTH: 7
<212> TYPE: PRT
<213> ORGANISM: Artificial Sequence
<220> FEATURE:
<223> OTHER INFORMATION: Synthetic peptide

<400> SEQUENCE: 116

Ser Ala Ser Phe Leu Tyr Ser
1               5

<210> SEQ ID NO 117
<211> LENGTH: 9
<212> TYPE: PRT
<213> ORGANISM: Artificial Sequence
<220> FEATURE:
<223> OTHER INFORMATION: Synthetic peptide

<400> SEQUENCE: 117

Gln Gln Ser Tyr Thr Thr Pro Pro Thr
1               5

<210> SEQ ID NO 118
```

```
<211> LENGTH: 9
<212> TYPE: PRT
<213> ORGANISM: Artificial Sequence
<220> FEATURE:
<223> OTHER INFORMATION: Synthetic peptide

<400> SEQUENCE: 118

Gln Gln Ser Tyr Thr Ser Ala Pro Thr
1               5

<210> SEQ ID NO 119
<211> LENGTH: 9
<212> TYPE: PRT
<213> ORGANISM: Artificial Sequence
<220> FEATURE:
<223> OTHER INFORMATION: Synthetic peptide

<400> SEQUENCE: 119

Gln Gln Ser Trp Thr Ala Pro Pro Thr
1               5

<210> SEQ ID NO 120
<211> LENGTH: 9
<212> TYPE: PRT
<213> ORGANISM: Artificial Sequence
<220> FEATURE:
<223> OTHER INFORMATION: Synthetic peptide

<400> SEQUENCE: 120

Gln Gln Ser Phe Thr Ala Pro Pro Thr
1               5

<210> SEQ ID NO 121
<211> LENGTH: 9
<212> TYPE: PRT
<213> ORGANISM: Artificial Sequence
<220> FEATURE:
<223> OTHER INFORMATION: Synthetic peptide

<400> SEQUENCE: 121

Gln Gln Ser Tyr Ile Ser Pro Pro Thr
1               5

<210> SEQ ID NO 122
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(9)
<223> OTHER INFORMATION: Variant residues given in the sequence have no
      preference with respect to those in the annotations for variant
      positions
<220> FEATURE:
<221> NAME/KEY: VARIANT
<222> LOCATION: (4)..(4)
<223> OTHER INFORMATION: Tyr or Trp or Phe
<220> FEATURE:
<221> NAME/KEY: VARIANT
<222> LOCATION: (5)..(5)
<223> OTHER INFORMATION: Thr or Ile
<220> FEATURE:
<221> NAME/KEY: VARIANT
<222> LOCATION: (6)..(6)
<223> OTHER INFORMATION: Thr or Ser or Ala
<220> FEATURE:
<221> NAME/KEY: VARIANT
<222> LOCATION: (7)..(7)
<223> OTHER INFORMATION: Pro or Ala
```

<400> SEQUENCE: 122

Gln Gln Ser Xaa Xaa Xaa Xaa Pro Thr
1               5

<210> SEQ ID NO 123
<211> LENGTH: 11
<212> TYPE: PRT
<213> ORGANISM: Artificial Sequence
<220> FEATURE:
<223> OTHER INFORMATION: Synthetic peptide

<400> SEQUENCE: 123

Arg Ala Ser Gln Asp Val Ser Thr Ala Val Ala
1               5                   10

<210> SEQ ID NO 124
<211> LENGTH: 7
<212> TYPE: PRT
<213> ORGANISM: Artificial Sequence
<220> FEATURE:
<223> OTHER INFORMATION: Synthetic peptide

<400> SEQUENCE: 124

Ser Ala Ser Phe Leu Tyr Ser
1               5

<210> SEQ ID NO 125
<211> LENGTH: 9
<212> TYPE: PRT
<213> ORGANISM: Artificial Sequence
<220> FEATURE:
<223> OTHER INFORMATION: Synthetic peptide

<400> SEQUENCE: 125

Gln Gln Ser Tyr Thr Thr Pro Pro Thr
1               5

<210> SEQ ID NO 126
<211> LENGTH: 9
<212> TYPE: PRT
<213> ORGANISM: Artificial Sequence
<220> FEATURE:
<223> OTHER INFORMATION: Synthetic peptide

<400> SEQUENCE: 126

Gln Gln Ser Tyr Ile Ser Pro Ser Thr
1               5

<210> SEQ ID NO 127
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(9)
<223> OTHER INFORMATION: Variant residues given in the sequence have no
      preference with respect to those in the annotations for variant
      positions
<220> FEATURE:
<221> NAME/KEY: VARIANT
<222> LOCATION: (5)..(5)
<223> OTHER INFORMATION: Thr or Ile
<220> FEATURE:
<221> NAME/KEY: VARIANT
<222> LOCATION: (6)..(6)
<223> OTHER INFORMATION: Thr or Ser

```
<220> FEATURE:
<221> NAME/KEY: VARIANT
<222> LOCATION: (8)..(8)
<223> OTHER INFORMATION: Pro or Ser

<400> SEQUENCE: 127

Gln Gln Ser Tyr Xaa Xaa Pro Xaa Thr
1               5

<210> SEQ ID NO 128
<211> LENGTH: 11
<212> TYPE: PRT
<213> ORGANISM: Artificial Sequence
<220> FEATURE:
<223> OTHER INFORMATION: Synthetic peptide

<400> SEQUENCE: 128

Arg Ala Ser Gln Ser Ile Ser Ser Tyr Leu Ala
1               5                   10

<210> SEQ ID NO 129
<211> LENGTH: 7
<212> TYPE: PRT
<213> ORGANISM: Artificial Sequence
<220> FEATURE:
<223> OTHER INFORMATION: Synthetic peptide

<400> SEQUENCE: 129

Gly Ala Ser Ser Arg Ala Ser
1               5

<210> SEQ ID NO 130
<211> LENGTH: 9
<212> TYPE: PRT
<213> ORGANISM: Artificial Sequence
<220> FEATURE:
<223> OTHER INFORMATION: Synthetic peptide

<400> SEQUENCE: 130

Gln Gln Tyr Tyr Ser Ser Pro Leu Thr
1               5

<210> SEQ ID NO 131
<211> LENGTH: 9
<212> TYPE: PRT
<213> ORGANISM: Artificial Sequence
<220> FEATURE:
<223> OTHER INFORMATION: Synthetic peptide

<400> SEQUENCE: 131

Gln Gln Tyr Leu Ser Ser Pro Ile Thr
1               5

<210> SEQ ID NO 132
<211> LENGTH: 9
<212> TYPE: PRT
<213> ORGANISM: Artificial Sequence
<220> FEATURE:
<223> OTHER INFORMATION: Synthetic peptide

<400> SEQUENCE: 132

Gln Gln Tyr Ser Ser Ser Pro Leu Thr
1               5

<210> SEQ ID NO 133
<211> LENGTH: 9
<212> TYPE: PRT
```

```
<213> ORGANISM: Artificial Sequence
<220> FEATURE:
<223> OTHER INFORMATION: Synthetic peptide

<400> SEQUENCE: 133

Gln Gln Tyr His Ser Ser Pro Leu Thr
1               5

<210> SEQ ID NO 134
<211> LENGTH: 9
<212> TYPE: PRT
<213> ORGANISM: Artificial Sequence
<220> FEATURE:
<223> OTHER INFORMATION: Synthetic peptide
<220> FEATURE:
<221> NAME/KEY: misc_feature
<222> LOCATION: (1)..(9)
<223> OTHER INFORMATION: Variant residues given in the sequence have no
      preference with respect to those in the annotations for variant
      positions
<220> FEATURE:
<221> NAME/KEY: VARIANT
<222> LOCATION: (4)..(4)
<223> OTHER INFORMATION: Tyr or Leu or Ser or His
<220> FEATURE:
<221> NAME/KEY: VARIANT
<222> LOCATION: (8)..(8)
<223> OTHER INFORMATION: Leu or Ile

<400> SEQUENCE: 134

Gln Gln Tyr Xaa Ser Ser Pro Xaa Thr
1               5

<210> SEQ ID NO 135
<211> LENGTH: 11
<212> TYPE: PRT
<213> ORGANISM: Homo sapiens

<400> SEQUENCE: 135

Phe Gly Gln Gly Thr Lys Val Glu Ile Lys Arg
1               5                   10

<210> SEQ ID NO 136
<211> LENGTH: 14
<212> TYPE: PRT
<213> ORGANISM: Homo sapiens

<400> SEQUENCE: 136

Trp Val Arg Gln Ala Pro Gly Lys Gly Leu Glu Trp Val Gly
1               5                   10

<210> SEQ ID NO 137
<211> LENGTH: 6
<212> TYPE: PRT
<213> ORGANISM: Artificial Sequence
<220> FEATURE:
<223> OTHER INFORMATION: Synthetic peptide

<400> SEQUENCE: 137

Leu Val Pro Arg Gly Ser
1               5

<210> SEQ ID NO 138
<211> LENGTH: 6
<212> TYPE: PRT
<213> ORGANISM: Artificial Sequence
<220> FEATURE:
<223> OTHER INFORMATION: Synthetic 6xHis tag
```

```
<400> SEQUENCE: 138

His His His His His His
1               5
```

ANTI-JAGGED ANTIBODIES AND METHODS OF USE

CROSS REFERENCE TO RELATED APPLICATIONS

This application is a non-provisional application filed under 37 C.F.R. § 1.53(b)(1), claiming priority under 35 U.S.C. § 119(e) to U.S. Provisional Application Ser. No. 61/682,640, filed Aug. 13, 2012, and U.S. Provisional Application Ser. No. 61/784,332, filed Mar. 14, 2013, the contents of which are hereby incorporated by reference in their entirety.

SEQUENCE LISTING

The instant application contains a Sequence Listing which has been submitted in ASCII format via EFS-Web and is hereby incorporated by reference in its entirety. Said ASCII copy, created on Mar. 15, 2018, is named 2018-03-15_01146-0026-00US_SEQLIST_REVISED_ST25.txt, and is 116,061 bytes in size.

FIELD OF THE INVENTION

The present invention relates to anti-Jagged antibodies and methods of using the same.

BACKGROUND

The Notch signaling pathway regulates a diverse array of cell functions (Kopan et al., Cell 137, 216-233 (2009)). Four Notch receptors have been identified in mammals, i.e., Notch 1-4, that share basic structural elements that include an extracellular domain, a transmembrane domain, and an intracellular domain. Similarly, the canonical ligands of Notch share certain structural similarities but a number of non-canonical ligands of Notch have also been identified (Kopan et al., Cell 137, 216-233 (2009)). The five canonical ligands in mammals are Delta-like 1, Delta-like 3, Delta-like 4, Jagged1 and Jagged2. Binding of a Notch ligand to the extracellular domain of a Notch receptor sets a signaling cascade in motion that begins with proteolytic cleavage at the extracellular S2 site by an alpha secretase of the ADAM (a disintegrin and metalloprotease) family. Cleavage at S2 is followed by proteolytic cleavage by a gamma secretase at the intracellular S3 site, which results in release of the intracellular domain and downstream events that ultimately activate Notch-dependent transcription factors such as Hes1 and Hey.

Because aberrant Notch expression and signaling has been implicated in a number of diseases, including cancer (Koch et al., Cell. Mol. Life Sci. 64, 2746-2762 (2007)), modulators of Notch signaling have been investigated as possible therapeutic agents for such diseases. For example, gamma secretase inhibitors have been tested in clinical trials for their effectiveness in treating various malignancies (Shih et al, Cancer Res. 67, 1879-1882 (2007)). Gamma secretase inhibitors prevent cleavage at S3 and thereby prevent signaling through Notch receptors. However, gamma secretase inhibitors do not distinguish individual Notch family members and therefore inhibit signaling through multiple receptors at once, as well as through unrelated pathways (Beel et al., Cell. Mol. Life Sci. 65, 1311-1334 (2008)). Consequently, administration of gamma secretase inhibitors is associated with intestinal toxicity marked by weight loss and intestinal goblet cell metaplasia, indicative of a role for Notch in determining cell fate by maintaining proliferation of intestinal crypt progenitor cells and prohibiting differentiation to a secretory cell fate (See van Es et al., Nature 435:959-963 (2005)). Similarly, inhibition of both Notch1 and Notch2 signaling via conditional Notch gene knockout (Riccio et al., EMBO Rep. 9:377-383 (2008)) or via antagonist antibody inhibition (US Patent Application Publication No. 2010/0080808) also causes intestinal goblet cell metaplasia.

Because of serious toxicity associated with inhibitors of multiple Notch receptors, there is a great need in the art for targeted inhibition of signaling through specific receptors.

SUMMARY

The invention provides anti-Jagged antibodies and methods of using the same.

In one aspect, the invention provides an isolated antibody that binds to Jagged1. In one embodiment, the antibody is an antagonist of Jagged1-mediated signaling. In one embodiment, the antibody comprises at least one, two, three, four, five, or six HVRs selected from: (a) HVR-H1 comprising the amino acid sequence of SEQ ID NO:81; (b) HVR-H2 comprising an amino acid sequence of SEQ ID NO:84; (c) HVR-H3 comprising an amino acid sequence of SEQ ID NO:87; (d) HVR-L1 comprising the amino acid sequence of SEQ ID NO:110; (e) HVR-L2 comprising the amino acid sequence of SEQ ID NO:111; and (f) HVR-L3 comprising an amino acid sequence of SEQ ID NO:114. In one embodiment, the antibody comprises: (a) an HVR-H1 comprising the amino acid sequence of SEQ ID NO:81; (b) an HVR-H2 comprising the amino acid sequence of SEQ ID NO:82; (c) an HVR-H3 comprising the amino acid sequence of SEQ ID NO:85; (d) an HVR-L1 comprising the amino acid sequence of SEQ ID NO:110; (e) an HVR-L2 comprising the amino acid sequence of SEQ ID NO:111; and (f) an HVR-L3 comprising the amino acid sequence of SEQ ID NO:112. In one embodiment, the antibody comprises: (a) an HVR-H1 comprising the amino acid sequence of SEQ ID NO:81; (b) an HVR-H2 comprising the amino acid sequence of SEQ ID NO:82; (c) an HVR-H3 comprising the amino acid sequence of SEQ ID NO:86; (d) an HVR-L1 comprising the amino acid sequence of SEQ ID NO:110; (e) an HVR-L2 comprising the amino acid sequence of SEQ ID NO:111; and (f) an HVR-L3 comprising the amino acid sequence of SEQ ID NO:113. In one embodiment, the antibody comprises: (a) an HVR-H1 comprising the amino acid sequence of SEQ ID NO:81; (b) an HVR-H2 comprising the amino acid sequence of SEQ ID NO:83; (c) an HVR-H3 comprising the amino acid sequence of SEQ ID NO:85; (d) an HVR-L1 comprising the amino acid sequence of SEQ ID NO:110; (e) an HVR-L2 comprising the amino acid sequence of SEQ ID NO:111; and (f) an HVR-L3 comprising the amino acid sequence of SEQ ID NO:112.

In another aspect, the invention provides an isolated antibody that binds to Jagged2. In one embodiment, the antibody is an antagonist of Jagged2-mediated signaling. In one embodiment, the antibody comprises at least one, two, three, four, five, or six HVRs selected from: (a) HVR-H1 comprising the amino acid sequence of SEQ ID NO:88; (b) HVR-H2 comprising the amino acid sequence of SEQ ID NO:89; (c) HVR-H3 comprising an amino acid sequence of SEQ ID NO:94; (d) HVR-L1 comprising the amino acid sequence of SEQ ID NO:115; (e) HVR-L2 comprising the amino acid sequence of SEQ ID NO:116; and (f) HVR-L3 comprising an amino acid sequence of SEQ ID NO:122. In one embodiment, the antibody comprises: (a) an HVR-H1 comprising the amino acid sequence of SEQ ID NO:88; (b) an HVR-H2 comprising the amino acid sequence of SEQ ID NO:89; (c) an HVR-H3 comprising the amino acid sequence of SEQ ID NO:90; (d) an HVR-L1 comprising the amino acid sequence of SEQ ID NO:115; (e) an HVR-L2 comprising the amino acid sequence of SEQ ID NO:116; and (f) an HVR-L3 comprising the amino acid sequence of SEQ ID NO:117. In one embodiment, the antibody comprises: (a) an HVR-H1 comprising the amino acid sequence of SEQ ID NO:88; (b) an HVR-H2 comprising the amino acid sequence of SEQ ID NO:89; (c) an HVR-H3 comprising the amino acid sequence of SEQ ID NO:91; (d) an HVR-L1 comprising the amino acid sequence of SEQ ID NO:115; (e) an HVR-L2 comprising the amino acid sequence of SEQ ID NO:116; and (f) an HVR-L3 comprising the amino acid sequence of SEQ ID NO:118. In one embodiment, the antibody comprises: (a) an HVR-H1 comprising the amino acid sequence of SEQ ID NO:88; (b) an HVR-H2 comprising the amino acid sequence of SEQ ID NO:89; (c) an HVR-H3 comprising the amino acid sequence of SEQ ID NO:90; (d) an HVR-L1 comprising the amino acid sequence of SEQ ID NO:115; (e) an HVR-L2 comprising the amino acid sequence of SEQ ID NO:116; and (f) an HVR-L3 comprising the amino acid sequence of SEQ ID NO:119. In one embodiment, the antibody comprises: (a) an HVR-H1 comprising the amino acid sequence of SEQ ID NO:88; (b) an HVR-H2 comprising the amino acid sequence of SEQ ID NO:89; (c) an HVR-H3 comprising the amino acid sequence of SEQ ID NO:92; (d) an HVR-L1 comprising the amino acid sequence of SEQ ID NO:115; (e) an HVR-L2 comprising the amino acid sequence of SEQ ID NO:116; and (f) an HVR-L3 comprising the amino acid sequence of SEQ ID NO:120. In one embodiment, the antibody comprises: (a) an HVR-H1 comprising the amino acid sequence of SEQ ID NO:88; (b) an HVR-H2 comprising the amino acid sequence of SEQ ID NO:89; (c) an HVR-H3 comprising the amino acid sequence of SEQ ID NO:93; (d) an HVR-L1 comprising the amino acid sequence of SEQ ID NO:115; (e) an HVR-L2 comprising the amino acid sequence of SEQ ID NO:116; and (f) an HVR-L3 comprising the amino acid sequence of SEQ ID NO:121.

In another aspect, the invention provides an isolated antibody that binds to Jagged1 and Jagged2 (Jagged1/2). In one embodiment, the antibody is an antagonist of Jagged1/2-mediated signaling. In one embodiment, the antibody comprises at least one, two, three, four, five, or six HVRs selected from: (a) an HVR-H1 comprising the amino acid sequence of SEQ ID NO:95; (b) an HVR-H2 comprising the amino acid sequence of SEQ ID NO:96; (c) an HVR-H3 comprising an amino acid sequence of SEQ ID NO:99; (d) an HVR-L1 comprising the amino acid sequence of SEQ ID NO:123; (e) an HVR-L2 comprising the amino acid sequence of SEQ ID NO:124; and (f) an HVR-L3 comprising an amino acid sequence of SEQ ID NO:127. In one embodiment, the antibody comprises: (a) an HVR-H1 comprising the amino acid sequence of SEQ ID NO:95; (b) an HVR-H2 comprising the amino acid sequence of SEQ ID NO:96; (c) an HVR-H3 comprising the amino acid sequence of SEQ ID NO:97; (d) an HVR-L1 comprising the amino acid sequence of SEQ ID NO:123; (e) an HVR-L2 comprising the amino acid sequence of SEQ ID NO:124; and (f) an HVR-L3 comprising the amino acid sequence of SEQ ID NO:125. In one embodiment, the antibody comprises: (a) an HVR-H1 comprising the amino acid sequence of SEQ ID NO:95; (b) an HVR-H2 comprising the amino acid sequence of SEQ ID NO:96; (c) an HVR-H3 comprising the amino acid sequence of SEQ ID NO:98; (d) an HVR-L1 comprising the amino acid sequence of SEQ ID NO:123; (e) an HVR-L2 comprising the amino acid sequence of SEQ ID NO:124; and (f) an HVR-L3 comprising the amino acid sequence of SEQ ID NO:126.

In another embodiment, the antibody comprises at least one, two, three, four, five, or six HVRs selected from: (a) an HVR-H1 comprising an amino acid sequence of SEQ ID NO:105; (b) an HVR-H2 comprising the amino acid sequence of SEQ ID NO:106; (c) an HVR-H3 comprising an amino acid sequence of SEQ ID NO:109; (d) an HVR-L1 comprising the amino acid sequence of SEQ ID NO:128; (e) an HVR-L2 comprising the amino acid sequence of SEQ ID NO:129; and (f) an HVR-L3 comprising an amino acid sequence of SEQ ID NO:134. In one embodiment, the antibody comprises: (a) an HVR-H1 comprising the amino acid sequence of SEQ ID NO:100; (b) an HVR-H2 comprising the amino acid sequence of SEQ ID NO:106; (c) an HVR-H3 comprising the amino acid sequence of SEQ ID NO:107; (d) an HVR-L1 comprising the amino acid sequence of SEQ ID NO:128; (e) an HVR-L2 comprising the amino acid sequence of SEQ ID NO:129; and (f) an HVR-L3 comprising the amino acid sequence of SEQ ID NO:130. In one embodiment, the antibody comprises: (a) an HVR-H1 comprising the amino acid sequence of SEQ ID NO:100; (b) an HVR-H2 comprising the amino acid sequence of SEQ ID NO:106; (c) an HVR-H3 comprising the amino acid sequence of SEQ ID NO:108; (d) an HVR-L1 comprising the amino acid sequence of SEQ ID NO:128; (e) an HVR-L2 comprising the amino acid sequence of SEQ ID NO:129; and (f) an HVR-L3 comprising the amino acid sequence of SEQ ID NO:131. In one embodiment, the antibody comprises: (a) an HVR-H1 comprising the amino acid sequence of SEQ ID NO:101; (b) an HVR-H2 comprising the amino acid sequence of SEQ ID NO:106; (c) an HVR-H3 comprising the amino acid sequence of SEQ ID NO:107; (d) an HVR-L1 comprising the amino acid sequence of SEQ ID NO:128; (e) an HVR-L2 comprising the amino acid sequence of SEQ ID NO:129; and (f) an HVR-L3 comprising the amino acid sequence of SEQ ID NO:132. In one embodiment, the antibody comprises: (a) an HVR-H1 comprising the amino acid sequence of SEQ ID NO:102; (b) an HVR-H2 comprising the amino acid sequence of SEQ ID NO:106; (c) an HVR-H3 comprising the amino acid sequence of SEQ ID NO:107; (d) an HVR-L1 comprising the amino acid sequence of SEQ ID NO:128; (e) an HVR-L2 comprising the amino acid sequence of SEQ ID NO:129; and (f) an HVR-L3 comprising the amino acid sequence of SEQ ID NO:133. In one embodiment, the antibody comprises: (a) an HVR-H1 comprising the amino acid sequence of SEQ ID NO:103; (b) an HVR-H2 comprising the amino acid sequence of SEQ ID NO:106; (c) an HVR-H3 comprising the amino acid sequence of SEQ ID NO:107; (d) an HVR-L1 comprising the amino acid sequence of SEQ ID NO:128; (e) an HVR-L2 comprising the amino acid sequence of SEQ ID NO:129; and (f) an HVR-L3 comprising the amino acid sequence of SEQ ID NO:132. In one embodiment, the antibody comprises: (a) an HVR-H1 comprising the amino acid sequence of SEQ ID NO:104; (b) an HVR-H2 comprising the amino acid sequence of SEQ ID NO:106; (c) an HVR-H3 comprising the amino acid sequence of SEQ ID NO:107; (d) an HVR-L1 comprising the amino acid sequence of SEQ ID NO:128; (e) an HVR-L2 comprising the amino acid sequence of SEQ ID NO:129; and (f) an HVR-L3 comprising the amino acid sequence of SEQ ID NO:132.

In certain embodiments of the invention, any of the above embodiments is a monoclonal antibody. In certain embodiments, any of the above embodiments is a human, humanized, or chimeric antibody. In certain embodiments, any of the above embodiments is an antibody fragment.

In another aspect, the invention provides an isolated antibody as described above, further comprising a light chain variable domain framework FR1 comprising the amino acid sequence of SEQ ID NO:60; FR2 comprising the amino acid sequence of SEQ ID NO:61; FR3 comprising the amino acid sequence of SEQ ID NO:62; and FR4 comprising the amino acid sequence of SEQ ID NO:135. In some embodiments, the antibody comprises a heavy chain variable domain framework FR1 comprising the amino acid sequence of SEQ ID NO:50; FR2 comprising the amino acid sequence of SEQ ID NO:136; FR3 comprising the amino acid sequence of SEQ ID NO:57; and FR4 comprising the amino acid sequence of SEQ ID NO:35. In some embodiments, the antibody comprises a heavy chain variable domain framework FR1 comprising the amino acid sequence of SEQ ID NO:50; FR2 comprising the amino acid sequence of SEQ ID NO:48; FR3 comprising the amino acid sequence of SEQ ID NO:57; and FR4 comprising the amino acid sequence of SEQ ID NO:35.

In another aspect, the invention provides an isolated antibody that binds to Jagged1, comprising (a) a VH sequence having at least 95% sequence identity to the amino acid sequence of SEQ ID NO:10; (b) a VL sequence having at least 95% sequence identity to the amino acid sequence of SEQ ID NO:19; or (c) a VH sequence as in (a) and a VL sequence as in (b). In some embodiments, the antibody comprises a VH sequence of SEQ ID NO:10. In some embodiments, the antibody comprises a VL sequence of SEQ ID NO:19. In some embodiments, the antibody comprises a VH sequence of SEQ ID NO:10 and a VL sequence of SEQ ID NO:19. In some embodiments, the antibody comprises (a) a VH sequence having at least 95% sequence identity to the amino acid sequence of SEQ ID NO:11; (b) a VL sequence having at least 95% sequence identity to the amino acid sequence of SEQ ID NO:20; or (c) a VH sequence as in (a) and a VL sequence as in (b). In some embodiments, the antibody comprises a VH sequence of SEQ ID NO:11. In some embodiments, the antibody comprises a VL sequence of SEQ ID NO:20. In some embodiments, the antibody comprises a VH sequence of SEQ ID NO:11 and a VL sequence of SEQ ID NO:20.

In another aspect, the invention provides an isolated antibody that binds to Jagged1, comprising (a) a VH sequence having at least 95% sequence identity to the amino acid sequence of SEQ ID NO:15; (b) a VL sequence having at least 95% sequence identity to the amino acid sequence of SEQ ID NO:24; or (c) a VH sequence as in (a) and a VL sequence as in (b). In some embodiments, the antibody comprises a VH sequence of SEQ ID NO:15. In some embodiments, the antibody comprises a VL sequence of SEQ ID NO:24. In some embodiments, the antibody comprises a VH sequence of SEQ ID NO:15 and a VL sequence of SEQ ID NO:24.

Any of the above embodiments may be a full-length IgG1 antibody.

In another aspect, the invention provides an isolated antibody that competes with any of the above embodiments for specific binding to Jagged1. In another aspect, the invention provides an isolated antibody that competes with any of the above embodiments for specific binding to Jagged2. In another aspect, the invention provides an isolated nucleic acid encoding an isolated antibody of the above embodiments. In a further aspect, the invention provides a host cell comprising the isolated nucleic acid encoding the antibody. In a further aspect, the invention provides a method of producing an antibody comprising culturing the host cell so that the antibody is produced.

In another aspect, the invention provides an immunoconjugate comprising an antibody of any of the above embodiments and a cytotoxic agent.

In another aspect, the invention provides a pharmaceutical formulation comprising an antibody of any of the above embodiments and a pharmaceutically acceptable carrier.

In another aspect, an antibody of any of the above embodiments is provided for use as a medicament. In some embodiments, an antibody of any of the above embodiments is provided for use in treating a cancer. In some embodiments, an antibody of any of the above embodiments is provided for use in reducing cancer cell growth.

In another aspect, a method of inhibiting Jagged1-mediated signaling is provided. In one embodiment, a method of inhibiting Jagged1-mediated signaling in vitro is provided. In one embodiment, a method of inhibiting Jagged1-mediated signaling in vivo is provided.

In another aspect, a method of treating an individual having a cancer comprising administering to the individual an effective amount of an antibody of any of the above embodiments. In one embodiment, the cancer is selected from the group consisting of: breast cancer, lung cancer, brain cancer, cervical cancer, colon cancer, liver cancer, bile duct cancer, pancreatic cancer, skin cancer, B-cell malignancies, and T-cell malignancies.

BRIEF DESCRIPTION OF THE FIGURES

FIG. 1 shows exemplary amino acid sequences of human and murine Jagged1 protein.

FIG. 2 shows exemplary amino acid sequences of human and murine Jagged2 protein.

FIGS. 3A-D show the amino acid sequences of peptides used for phage antibody library screening and selection. All proteins were expressed as a secreted protein in BEVS cells and their sequences are listed in the N-terminal to C-terminal direction. (A) Amino acid sequence of expressed protein murine Jagged 1-DSL-EGF1-4 (Q34-D377). The bold font at the N-terminus represents a short linker sequence (ADLGS) (SEQ ID NO: 31). The bold font at the C-terminus represents a short linker sequence (EFG), a thrombin cleavage site (LVPRGS) (SEQ ID NO: 137), a G spacer and the 6-His tag (SEQ ID NO: 138). (B) Amino acid sequence of expressed protein human Jag1-DSL-EGF1-4. Only the Jag1 sequence is shown although the antigen also contained a TEV protease cleavage site and 6-His tag (SEQ ID NO: 138) at the C-terminus. (C) Amino acid sequence of expressed protein murine Jag2-DSL-EGF1-4 (M27-E388). The bold font at the N-terminus represents a short linker sequence (ADLGS) (SEQ ID NO: 31). The bold font at the C-terminus represents a short linker sequence (EFG), a thrombin cleavage site (LVPRGS) (SEQ ID NO: 137), a G spacer and the 6-His tag (SEQ ID NO: 138). (D) Amino acid sequence of expressed protein human Jag2-DSL-EGF1-4 (R2-E388). The bold font at the C-terminus represents a short linker sequence (EFG), a thrombin cleavage site (LVPRGS) (SEQ ID NO: 137), a G spacer and the 6-His tag (SEQ ID NO: 138).

Figure 4A-1:
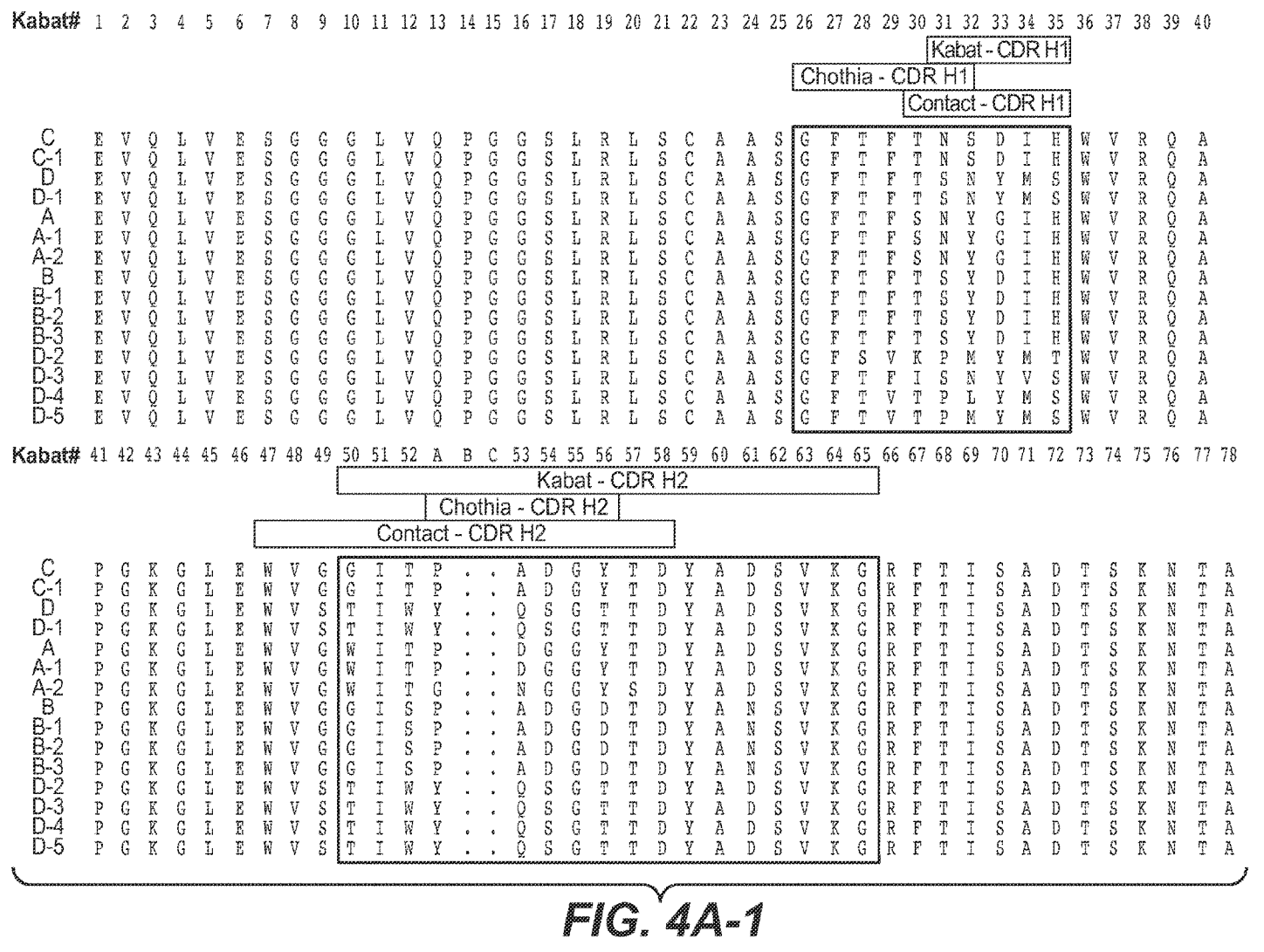
Figure 4A-2:
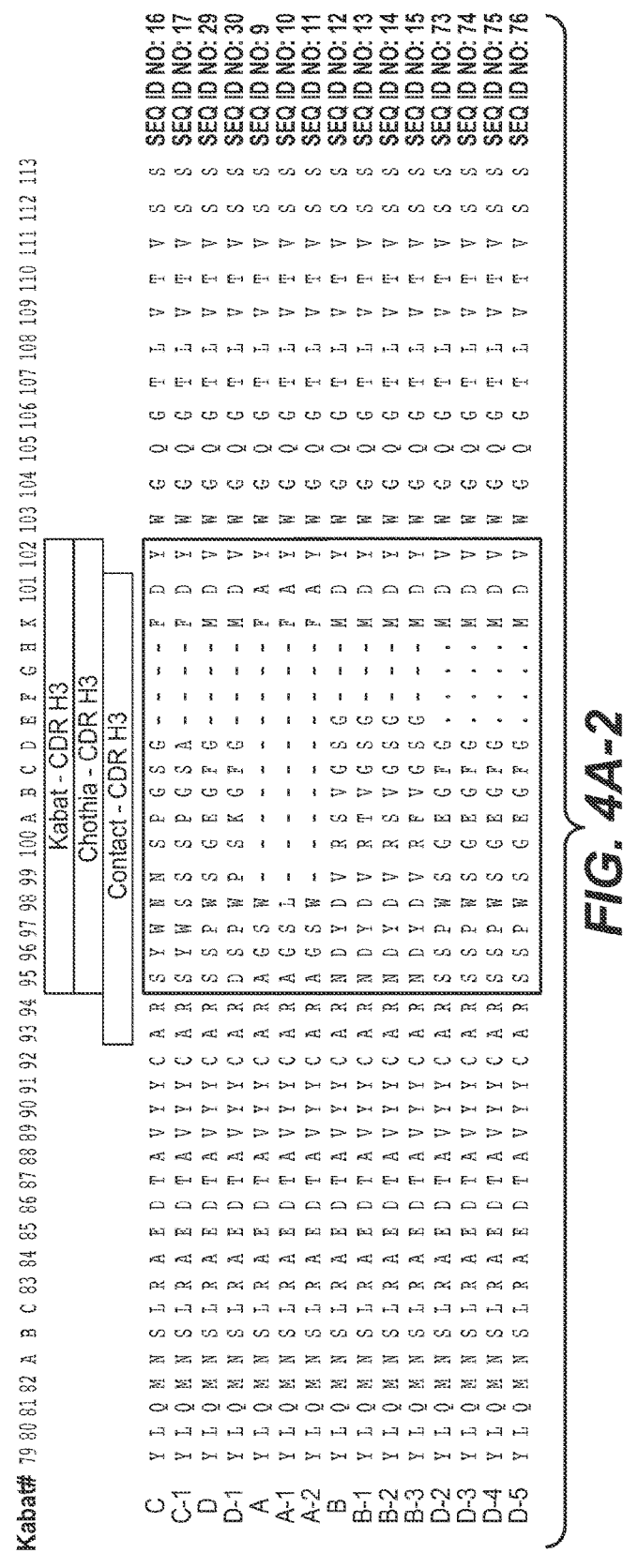
Figure 4B-1:
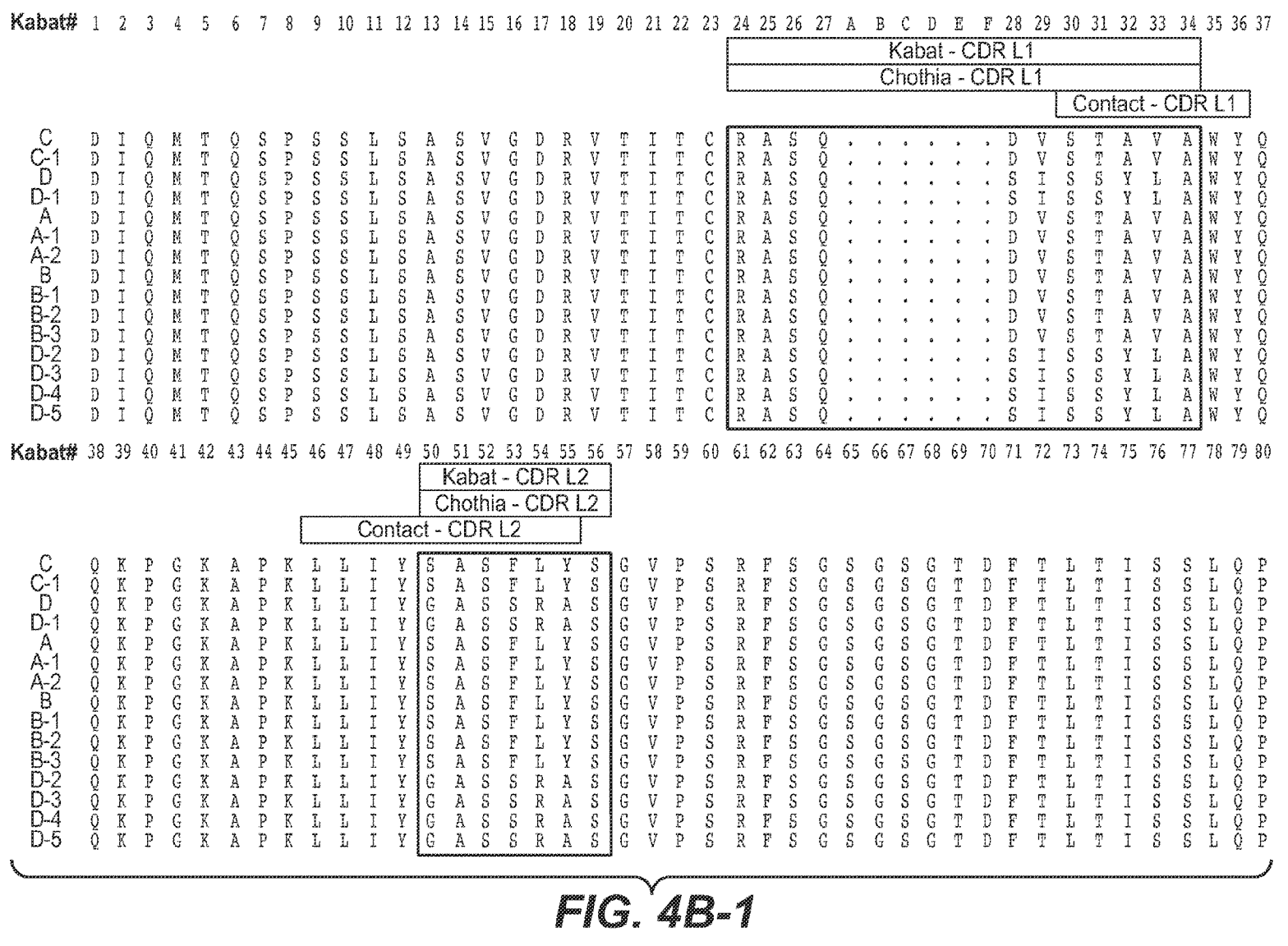

FIGS. 4A-1-B-2 show an alignment of the amino acid sequences for the heavy (FIG. 4A-1 and FIG. 4A-2) and light (FIG. 4B-1 and FIG. 4B-2) chain variable domains of anti-Jagged antibodies (Example 1-2). Amino acid positions of the complementarity determining regions (CDRs) are indicated.

FIGS. 5A-B show exemplary acceptor human variable heavy (VH) consensus framework sequences for use in practicing the instant invention. Sequence identifiers are as follows:
  human VH subgroup I consensus framework "A" minus Kabat CDRs (SEQ ID NOs:32, 33, 34, 35).
  human VH subgroup I consensus frameworks "B," "C," and "D" minus extended hypervariable regions (SEQ ID NOs:36, 37, 34, 35; SEQ ID NOs:36, 37, 38, 35; and SEQ ID NOs:36, 37, 39, 35).
  human VH subgroup II consensus framework "A" minus Kabat CDRs (SEQ ID NOs:40, 41, 42, 35).
  human VH subgroup II consensus frameworks "B," "C," and "D" minus extended hypervariable regions (SEQ ID NOs:43, 44, 42, 35; SEQ ID NOs:43, 44, 45, 35; and SEQ ID NOs:43, 44, 46, and 35).
  human VH subgroup III consensus framework "A" minus Kabat CDRs (SEQ ID NOs:47, 48, 49, 35).
  human VH subgroup III consensus frameworks "B," "C," and "D" minus extended hypervariable regions (SEQ ID NOs:50, 51, 49, 35; SEQ ID NOs:50, 51, 52, 35; and SEQ ID NOs:50, 51, 53, 35).
  human VH acceptor framework "A" minus Kabat CDRs (SEQ ID NOs:54, 48, 55, 35).
  human VH acceptor frameworks "B" and "C" minus extended hypervariable regions (SEQ ID NOs:50, 51, 55, 35; and SEQ ID NOs:50, 51, 56, 35).
  human VH acceptor 2 framework "A" minus Kabat CDRs (SEQ ID NOs:54, 48, 57, 35).
  human VH acceptor 2 framework "B," "C," and "D" minus extended hypervariable regions (SEQ ID NOs: 50, 51, 57, 35; SEQ ID NOs:50, 51, 58, 35; and SEQ ID NOs:50, 51, 59, 35).

FIGS. 7A-F show the H1, H2, and H3 heavy chain hypervariable region (HVR) sequences of anti-Jagged antibodies, as described in the Examples. Amino acid positions are numbered according to the Kabat numbering system as described below.

FIGS. 8A-E show the L1, L2, and L3 light chain HVR sequences of anti-Jagged antibodies, as described in the Examples. Amino acid positions are numbered according to the Kabat numbering system as described below.

FIG. 9 shows light and heavy chain framework sequences of anti-Jagged antibodies described in the Examples. Numbers in superscript indicate amino acid positions according to Kabat.

FIGS. 10A-B show binding specificity of antibodies obtained from the first (FIG. 10A) and second (FIG. 10B) round of screening. (A) Results of ELISA assays measuring binding of antibody D-1 (left panel) and C-1 (right panel) to human Jagged1 (hJag-1), human Jagged2 (hJag-2), murine Jagged2 (mJag-2), human Delta-like 1 (hDLL-1), murine Delta-like 1 (mDLL-1), or human Delta-like 4 (hDLL-4). Antibody concentrations are indicated on the x-axis and OD650 on the y-axis. (B) Results of ELISA assays measuring binding specificity of Antibodies A and B, both identified during further screening using human Jag1-DSL-EGF1-4 (FIG. 3B) for antibody A and murine and human Jag2-DSL-EGF1-4 (FIGS. 3C and D) for antibody B. Black columns=binding to human Jagged1; gray columns=binding to human Jagged2. C-1 served as a control for binding to both Jagged1 and Jagged2.

FIG. 11 shows binding constants for antibodies A, A-1, A-2, B, B-1, B-2, B-3, C, C-1, D, D-1, and D-2 binding to purified human Jagged1 (human Jag1), human Jagged2 (human Jag2), and mouse Jagged2 (mouse Jag2).

FIGS. 15A-B show normal intestinal histology of following anti-Jagged antibody treatment. (A) Intestinal samples of mice treated as described in Example 6 were isolated and stained with hematoxylin and eosin (FIG. 15A, H & E) or with Alcian Blue (FIG. 15A, Alcian Blue). (B) Sections of intestine samples were stained with primary antibodies to either lysozyme or Ki-67 (FIG. 15B)

FIGS. 16A-1-B-2 show inhibition of human lung cancer cell growth by an anti-Jagged1 antagonist antibody in vivo. Mice bearing human lung cancer xenografts were injected twice per week intraperitoneally (IP) with 20mpk anti-gD isotype control antibody (Isotype control Ab) or with anti-Jagged1 antibody A-2 (Anti-Jag1), with the injections starting after average tumor volumes (measured with calipers) reached approximately 180 mm$^3$. Tumor volumes (y-axis) were subsequently measured for 19 days. FIG. 16A-1 and FIG. 16A-2: The average tumor volumes for each group (n=10) were plotted over time (x-axis) using a linear mixed effects model (FIG. 16A-1). Tumor volumes for each mouse in each group are depicted in the two panels in FIG. 16A-2. FIG. 16B-1 and FIG. 16B-2: Total body weight of each mouse was measured and graphed as the percentage change averaged for each group (FIG. 16B-1) or for each mouse in each group (FIG. 16B-2).

DETAILED DESCRIPTION OF EMBODIMENTS OF THE INVENTION

I. Definitions

Figure 6:
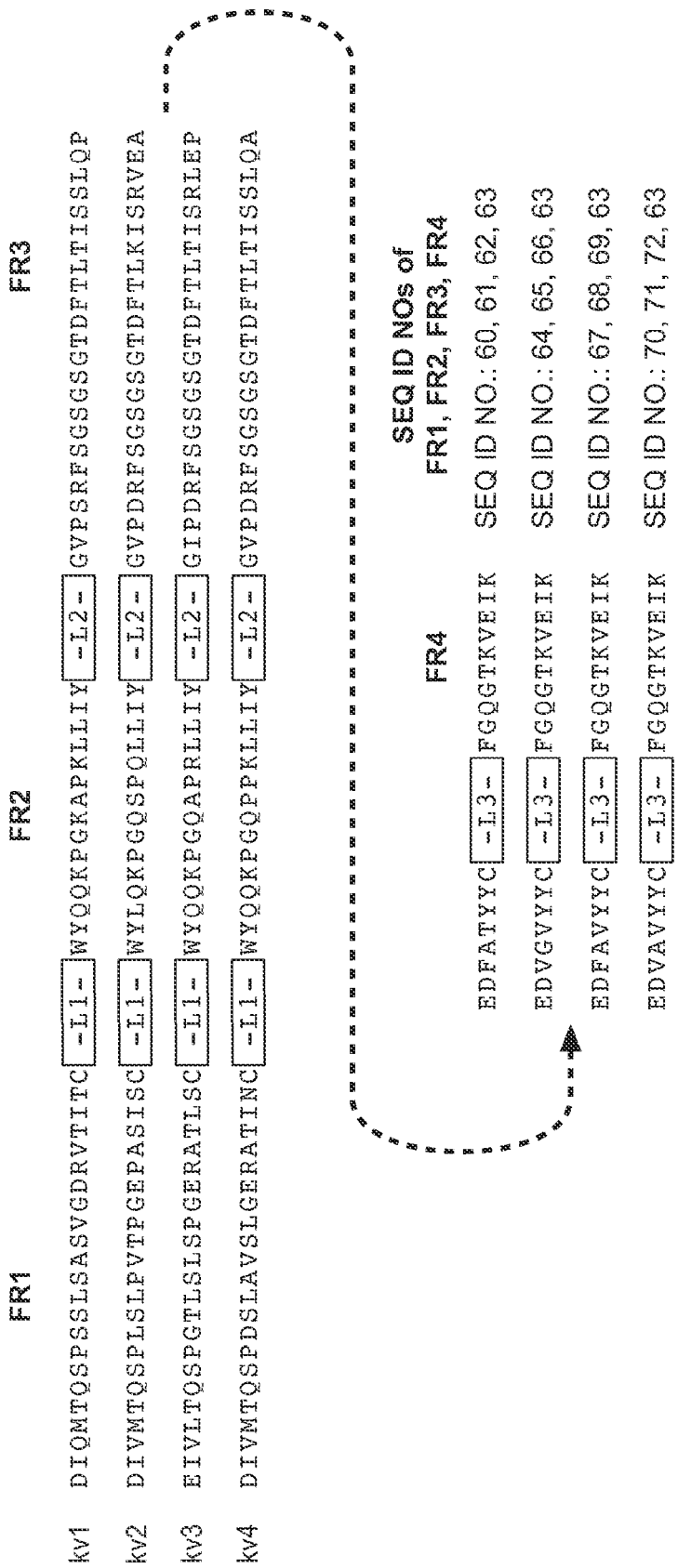
FIG. 6 shows exemplary acceptor human variable light (VL) consensus framework sequences for use in practicing the instant invention. Sequence identifiers are as follows:
  human VL kappa subgroup I consensus framework (κv1): SEQ ID NOs:60, 61, 62, 63
  human VL kappa subgroup II consensus framework (κv2): SEQ ID NOs:64, 65, 66, 63
  human VL kappa subgroup III consensus framework (κv3): SEQ ID NOs:67, 68, 69, 63
  human VL kappa subgroup IV consensus framework (κv4): SEQ ID NOs:70, 71, 72, 63

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of noncovalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant (Kd). Affinity can be measured by common methods known in the art, including those described herein. Specific illustrative and exemplary embodiments for measuring binding affinity are described in the following.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The terms "anti-Jagged antibody" and "an antibody that binds to Jagged" refer to an antibody that is capable of binding Jagged1, Jagged2, or Jagged1 and 2 (Jagged1/2) with sufficient affinity such that the antibody is useful as a diagnostic and/or therapeutic agent in targeting Jagged. In one embodiment, the extent of binding of an anti-Jagged antibody to an unrelated, non-Jagged protein is less than about 10% of the binding of the antibody to Jagged as measured, e.g., by a radioimmunoassay (RIA). In certain embodiments, an antibody that binds to Jagged has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M). In certain embodiments, an anti-Jagged antibody binds to an epitope of Jagged that is conserved among Jagged from different species.

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

A "blocking" antibody or an "antagonist" antibody is one which significantly inhibits (either partially or completely) a biological activity of the antigen it binds.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

An "antibody that binds to the same epitope" as a reference antibody refers to an antibody that blocks binding of the reference antibody to its antigen in a competition assay by 50% or more, and conversely, the reference antibody blocks binding of the antibody to its antigen in a competition assay by 50% or more. An exemplary competition assay is provided herein.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and µ, respectively.

The term "cytotoxic agent" as used herein refers to a substance that inhibits or prevents a cellular function and/or causes cell death or destruction. Cytotoxic agents include, but are not limited to, radioactive isotopes (e.g., At$^{211}$, I$^{131}$, I$^{125}$, Y$^{90}$, Re$^{186}$, Re$^{188}$, sm$^{153}$, Bi$^{212}$, P$^{32}$, Pb$^{212}$ and radioactive isotopes of Lu); chemotherapeutic agents or drugs (e.g., methotrexate, adriamicin, vinca alkaloids (vincristine, vinblastine, etoposide), doxorubicin, melphalan, mitomycin C, chlorambucil, daunorubicin or other intercalating agents); growth inhibitory agents; enzymes and fragments thereof such as nucleolytic enzymes; antibiotics; toxins such as small molecule toxins or enzymatically active toxins of bacterial, fungal, plant or animal origin, including fragments and/or variants thereof; and the various antitumor or anticancer agents disclosed below.

"Effector functions" refer to those biological activities attributable to the Fc region of an antibody, which vary with the antibody isotype. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

An "effective amount" of an agent, e.g., a pharmaceutical formulation, refers to an amount effective, at dosages and for periods of time necessary, to achieve the desired therapeutic or prophylactic result.

The term "Fc region" herein is used to define a C-terminal region of an immunoglobulin heavy chain that contains at least a portion of the constant region. The term includes native sequence Fc regions and variant Fc regions. In one embodiment, a human IgG heavy chain Fc region extends from Cys226, or from Pro230, to the carboxyl-terminus of the heavy chain. However, the C-terminal lysine (Lys447) of the Fc region may or may not be present. Unless otherwise specified herein, numbering of amino acid residues in the Fc region or constant region is according to the EU numbering system, also called the EU index, as described in Kabat et al., *Sequences of Proteins of Immunological Interest*, 5th Ed. Public Health Service, National Institutes of Health, Bethesda, Md., 1991.

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1 (L1)-FR2-H2(L2)-FR3-H3(L3)-FR4.

The terms "full length antibody," "intact antibody," and "whole antibody" are used herein interchangeably to refer to an antibody having a structure substantially similar to a native antibody structure or having heavy chains that contain an Fc region as defined herein.

The terms "host cell," "host cell line," and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human antibody" is one which possesses an amino acid sequence which corresponds to that of an antibody produced by a human or a human cell or derived from a non-human source that utilizes human antibody repertoires or other human antibody-encoding sequences. This definition of a human antibody specifically excludes a humanized antibody comprising non-human antigen-binding residues.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat et al., *Sequences of Proteins of Immunological Interest*, Fifth Edition, NIH Publication 91-3242, Bethesda Md. (1991), vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR" as used herein refers to each of the regions of an antibody variable domain which are hypervariable in sequence ("complementarity determining regions" or "CDRs") and/or form structurally defined loops ("hypervariable loops") and/or contain the antigen-contacting residues ("antigen contacts"). Generally, antibodies comprise six HVRs: three in the VH (H1, H2, H3), and three in the VL (L1, L2, L3). Exemplary HVRs herein include:

(a) hypervariable loops occurring at amino acid residues 26-32 (L1), 50-52 (L2), 91-96 (L3), 26-32 (H1), 53-55 (H2), and 96-101 (H3) (Chothia and Lesk, *J. Mol. Biol.* 196:901-917 (1987));

(b) CDRs occurring at amino acid residues 24-34 (L1), 50-56 (L2), 89-97 (L3), 31-35b (H1), 50-65 (H2), and 95-102 (H3) (Kabat et al., *Sequences of Proteins of Immunological Interest*, 5th Ed. Public Health Service, National Institutes of Health, Bethesda, Md. (1991));

(c) antigen contacts occurring at amino acid residues 27c-36 (L1), 46-55 (L2), 89-96 (L3), 30-35b (H1), 47-58 (H2), and 93-101 (H3) (MacCallum et al. *J. Mol. Biol.* 262: 732-745 (1996)); and (d) combinations of (a), (b), and/or (c), including HVR amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

An "immunoconjugate" is an antibody conjugated to one or more heterologous molecule(s), including but not limited to a cytotoxic agent.

An "individual" or "subject" is a mammal Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman et al., *J. Chromatogr. B* 848:79-87 (2007).

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-Jagged antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

A "naked antibody" refers to an antibody that is not conjugated to a heterologous moiety (e.g., a cytotoxic moiety) or radiolabel. The naked antibody may be present in a pharmaceutical formulation.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3). Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

The term "package insert" is used to refer to instructions customarily included in commercial packages of therapeutic products, that contain information about the indications, usage, dosage, administration, combination therapy, contraindications and/or warnings concerning the use of such therapeutic products.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

$$100 \text{ times the fraction } X/Y$$

where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The term "pharmaceutical formulation" refers to a preparation which is in such form as to permit the biological activity of an active ingredient contained therein to be effective, and which contains no additional components which are unacceptably toxic to a subject to which the formulation would be administered.

A "pharmaceutically acceptable carrier" refers to an ingredient in a pharmaceutical formulation, other than an active ingredient, which is nontoxic to a subject. A pharmaceutically acceptable carrier includes, but is not limited to, a buffer, excipient, stabilizer, or preservative.

Figures 1, 16A:
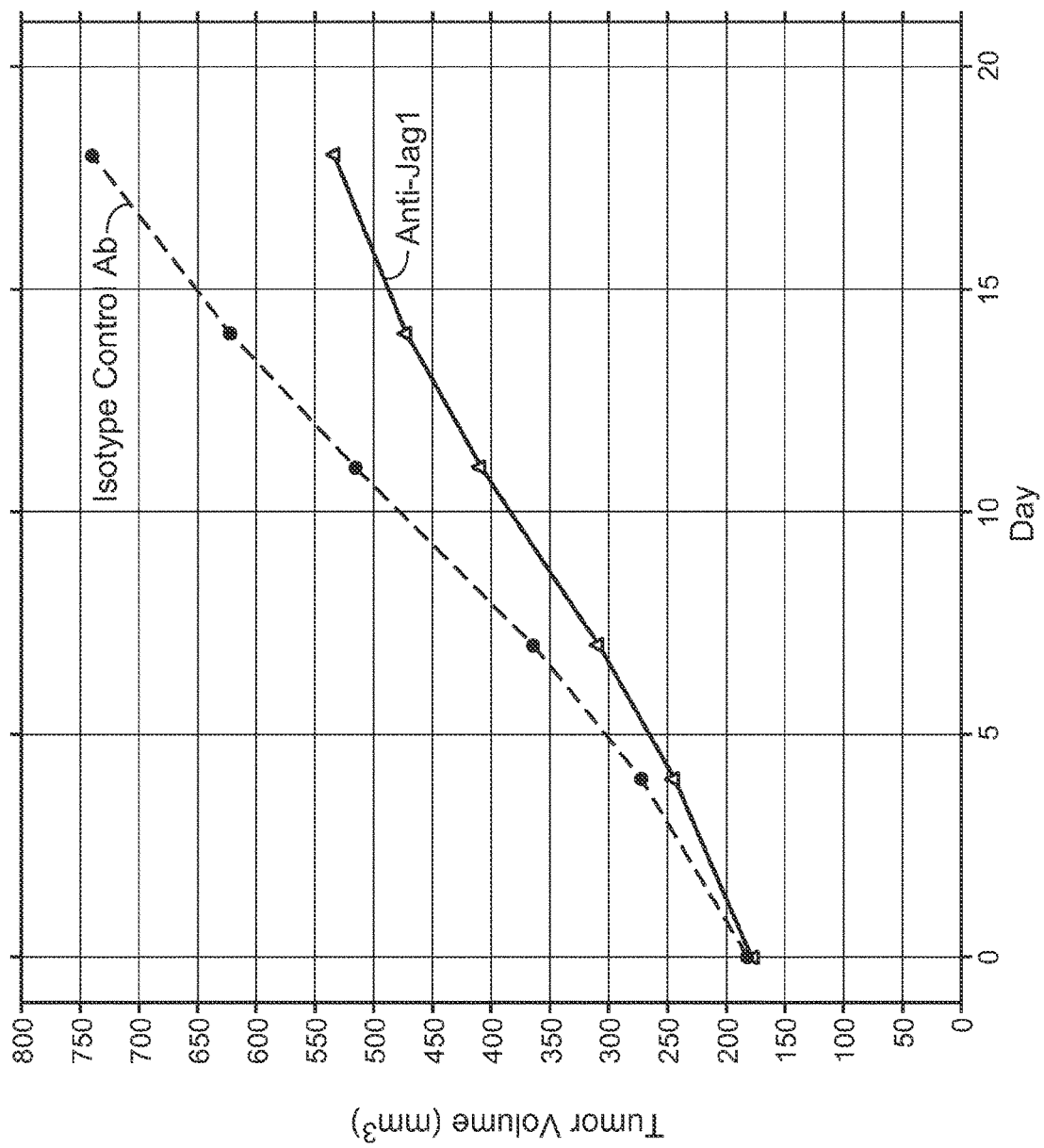
Figures 2, 16A:
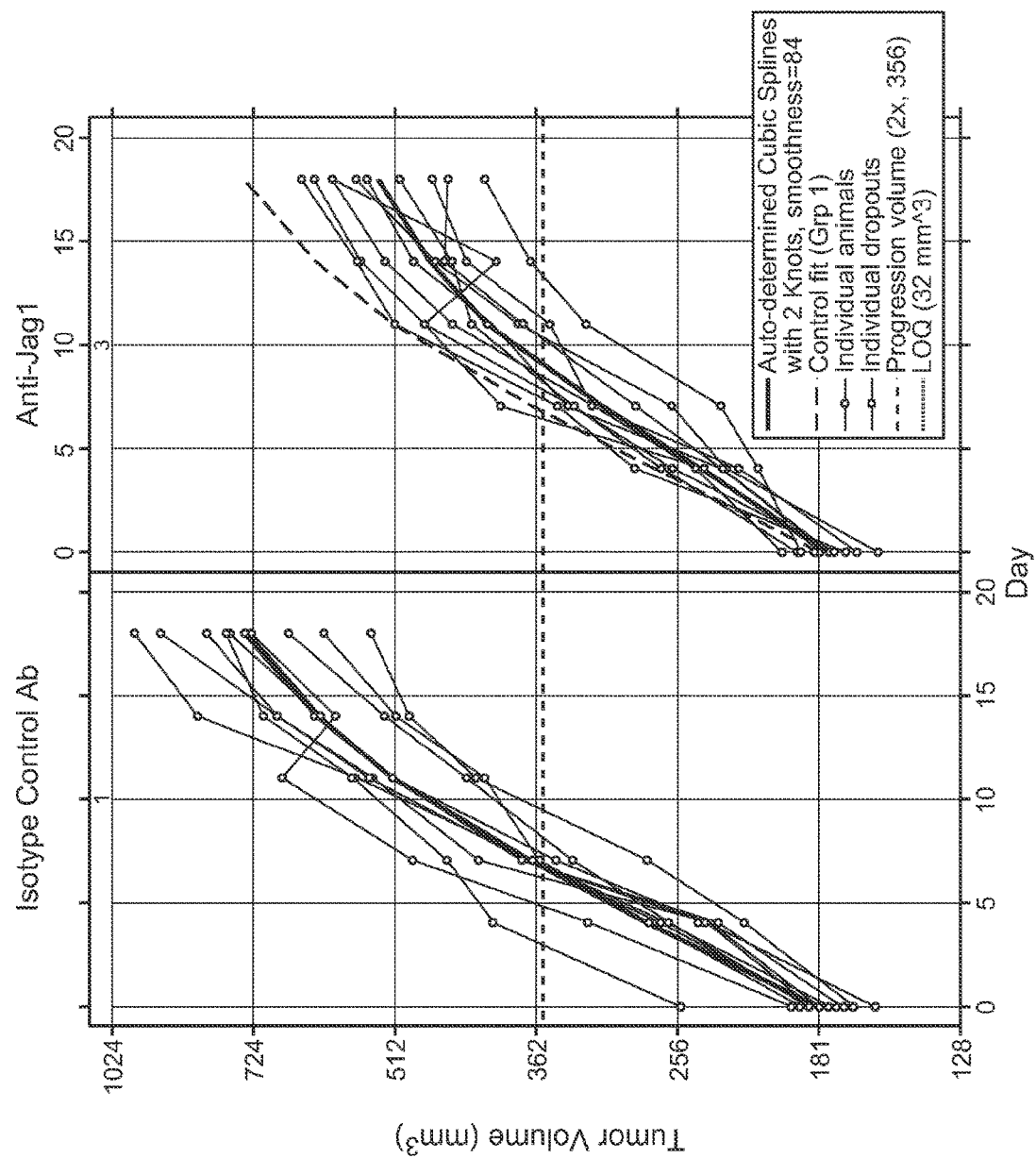

The term "Jagged" or "Jag," as used herein, refers to any native Jagged from any vertebrate source, including mammals such as primates (e.g. humans) and rodents (e.g., mice and rats), unless otherwise indicated. The term encompasses "full-length," unprocessed Jagged as well as any form of Jagged that results from processing in the cell. The term also encompasses naturally occurring variants of Jagged, e.g., splice variants or allelic variants. The amino acid sequence of an exemplary human and murine Jagged1 and Jagged2 is shown in FIGS. 1 and 2 (SEQ ID NOS:1-4), respectively.

As used herein, "treatment" (and grammatical variations thereof such as "treat" or "treating") refers to clinical intervention in an attempt to alter the natural course of the individual being treated, and can be performed either for prophylaxis or during the course of clinical pathology. Desirable effects of treatment include, but are not limited to, preventing occurrence or recurrence of disease, alleviation of symptoms, diminishment of any direct or indirect pathological consequences of the disease, preventing metastasis, decreasing the rate of disease progression, amelioration or palliation of the disease state, and remission or improved prognosis. In some embodiments, antibodies of the invention are used to delay development of a disease or to slow the progression of a disease.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt et al. *Kuby Immunology*, 6$^{th}$ ed., W.H. Freeman and Co., page 91 (2007).) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively. See, e.g., Portolano et al., *J. Immunol.* 150:880-887 (1993); Clarkson et al., *Nature* 352:624-628 (1991).

The term "vector," as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors."

II. Compositions and Methods

In one aspect, the invention is based, in part, on the identification of anti-Jagged antibodies and fragments thereof. In certain embodiments, antibodies that bind to at least one Jagged are provided. Antibodies of the invention are useful, e.g., for the diagnosis or treatment of cancer. Accordingly, the invention provides methods, compositions, kits, and articles of manufacture related to anti-Jagged antibodies.

A. Exemplary Anti-Jagged Antibodies

In one aspect, the invention provides isolated antibodies that bind to Jagged. In certain embodiments, the anti-Jagged antibody is an anti-Jagged1 antibody.

In one aspect, the invention provides an anti-Jagged1 antibody comprising at least one, two, three, four, five, or six HVRs selected from:

(a) HVR-H1 comprising the amino acid sequence of SEQ ID NO:81;
(b) HVR-H2 comprising an amino acid sequence of SEQ ID NO:84;
(c) HVR-H3 comprising an amino acid sequence of SEQ ID NO:87;
(d) HVR-L1 comprising the amino acid sequence of SEQ ID NO:110;
(e) HVR-L2 comprising the amino acid sequence of SEQ ID NO:111; and
(f) HVR-L3 comprising an amino acid sequence of SEQ ID NO:114.

In a further aspect, the anti-Jagged1 antibody comprises an HVR-H1 comprising the amino acid sequence of SEQ ID NO:81 and at least one, two, three, four, or five HVRs selected from (b), (c), (d), (e) and (f) above. In one embodiment, the antibody comprises (a), (b), (c), (d), (e) and (f) above, wherein with respect to (b) (c), and (f) any one or more of the following embodiments are contemplated: HVR-H2 comprises an amino acid sequence selected from SEQ ID NOs: 82-83; HVR-H3 comprises an amino acid sequence selected from SEQ ID NOs: 85-86; and HVR-L3 comprises an amino acid sequence selected from SEQ ID NOs: 112-113.

In another embodiment, an antibody that specifically binds to Jagged1 is provided, wherein the antibody comprises:

(a) an HVR-H1 comprising the amino acid sequence of SEQ ID NO:81;
(b) an HVR-H2 comprising the amino acid sequence of SEQ ID NO:82;
(c) an HVR-H3 comprising the amino acid sequence of SEQ ID NO:85;
(d) an HVR-L1 comprising the amino acid sequence of SEQ ID NO:110;
(e) an HVR-L2 comprising the amino acid sequence of SEQ ID NO:111; and
(f) an HVR-L3 comprising the amino acid sequence of SEQ ID NO:112.

In another embodiment, an antibody that specifically binds to Jagged1 is provided, wherein the antibody comprises:

(a) an HVR-H1 comprising the amino acid sequence of SEQ ID NO:81;
(b) an HVR-H2 comprising the amino acid sequence of SEQ ID NO:82;
(c) an HVR-H3 comprising the amino acid sequence of SEQ ID NO:86;
(d) an HVR-L1 comprising the amino acid sequence of SEQ ID NO:110;
(e) an HVR-L2 comprising the amino acid sequence of SEQ ID NO:111; and
(f) an HVR-L3 comprising the amino acid sequence of SEQ ID NO:113.

In another embodiment, an antibody that specifically binds to Jagged1 is provided, wherein the antibody comprises:

(a) an HVR-H1 comprising the amino acid sequence of SEQ ID NO:81;
(b) an HVR-H2 comprising the amino acid sequence of SEQ ID NO:83;
(c) an HVR-H3 comprising the amino acid sequence of SEQ ID NO:85;
(d) an HVR-L1 comprising the amino acid sequence of SEQ ID NO:110;
(e) an HVR-L2 comprising the amino acid sequence of SEQ ID NO:111; and
(f) an HVR-L3 comprising the amino acid sequence of SEQ ID NO:112.

In certain embodiments, the anti-Jagged antibody is an anti-Jagged2 antibody.

In one aspect, the invention provides an anti-Jagged2 antibody comprising at least one, two, three, four, five, or six HVRs selected from:
(a) HVR-H1 comprising the amino acid sequence of SEQ ID NO:88;
(b) HVR-H2 comprising the amino acid sequence of SEQ ID NO:89;
(c) HVR-H3 comprising an amino acid sequence of SEQ ID NO:94;
(d) HVR-L1 comprising the amino acid sequence of SEQ ID NO:115;
(e) HVR-L2 comprising the amino acid sequence of SEQ ID NO:116; and
(f) HVR-L3 comprising an amino acid sequence of SEQ ID NO:122.

In a further aspect, the anti-Jagged2 antibody comprises an HVR-H1 comprising the amino acid sequence of SEQ ID NO:88 and at least one, two, three, four, or five HVRs selected from (b), (c), (d), (e) and (f) above. In one embodiment, the antibody comprises (a), (b), (c), (d), (e) and (f) above, wherein with respect to (c) and (f) any one or more of the following embodiments are contemplated: HVR-H3 comprises an amino acid sequence selected from SEQ ID NOs:90-93; and HVR-L3 comprises an amino acid sequence selected from SEQ ID NOs:117-121.

In one embodiment, an antibody that specifically binds to Jagged2 is provided, wherein the antibody comprises:
(a) an HVR-H1 comprising the amino acid sequence of SEQ ID NO:88;
(b) an HVR-H2 comprising the amino acid sequence of SEQ ID NO:89;
(c) an HVR-H3 comprising the amino acid sequence of SEQ ID NO:90;
(d) an HVR-L1 comprising the amino acid sequence of SEQ ID NO:115;
(e) an HVR-L2 comprising the amino acid sequence of SEQ ID NO:116; and
(f) an HVR-L3 comprising the amino acid sequence of SEQ ID NO:117.

In another embodiment, an antibody that specifically binds to Jagged2 is provided, wherein the antibody comprises:
(a) an HVR-H1 comprising the amino acid sequence of SEQ ID NO:88;
(b) an HVR-H2 comprising the amino acid sequence of SEQ ID NO:89;
(c) an HVR-H3 comprising the amino acid sequence of SEQ ID NO:91;
(d) an HVR-L1 comprising the amino acid sequence of SEQ ID NO:115;
(e) an HVR-L2 comprising the amino acid sequence of SEQ ID NO:116; and
(f) an HVR-L3 comprising the amino acid sequence of SEQ ID NO:118.

In another embodiment, an antibody that specifically binds to Jagged2 is provided, wherein the antibody comprises:
(a) an HVR-H1 comprising the amino acid sequence of SEQ ID NO:88;
(b) an HVR-H2 comprising the amino acid sequence of SEQ ID NO:89;
(c) an HVR-H3 comprising the amino acid sequence of SEQ ID NO:90;
(d) an HVR-L1 comprising the amino acid sequence of SEQ ID NO:115;
(e) an HVR-L2 comprising the amino acid sequence of SEQ ID NO:116; and
(f) an HVR-L3 comprising the amino acid sequence of SEQ ID NO:119.

In another embodiment, an antibody that specifically binds to Jagged2 is provided, wherein the antibody comprises:
(a) an HVR-H1 comprising the amino acid sequence of SEQ ID NO:88;
(b) an HVR-H2 comprising the amino acid sequence of SEQ ID NO:89;
(c) an HVR-H3 comprising the amino acid sequence of SEQ ID NO:92;
(d) an HVR-L1 comprising the amino acid sequence of SEQ ID NO:115;
(e) an HVR-L2 comprising the amino acid sequence of SEQ ID NO:116; and
(f) an HVR-L3 comprising the amino acid sequence of SEQ ID NO:120.

In another embodiment, an antibody that specifically binds to Jagged2 is provided, wherein the antibody comprises:
(a) an HVR-H1 comprising the amino acid sequence of SEQ ID NO:88;
(b) an HVR-H2 comprising the amino acid sequence of SEQ ID NO:89;
(c) an HVR-H3 comprising the amino acid sequence of SEQ ID NO:93;
(d) an HVR-L1 comprising the amino acid sequence of SEQ ID NO:115;
(e) an HVR-L2 comprising the amino acid sequence of SEQ ID NO:116; and
(f) an HVR-L3 comprising the amino acid sequence of SEQ ID NO:121.

In certain embodiments, the anti-Jagged antibody is an anti-Jagged1/2 antibody.

In one aspect, the invention provides an anti-Jagged1/2 antibody comprising at least one, two, three, four, five, or six HVRs selected from an HVR-H1 comprising the amino acid sequence of SEQ ID NO:95; HVR-H2 comprising the amino acid sequence of SEQ ID NO:96; HVR-H3 comprising an amino acid sequence of SEQ ID NO:99; HVR-L1 comprising the amino acid sequence of SEQ ID NO:123; HVR-L2 comprising the amino acid sequence of SEQ ID NO:124; and HVR-L3 comprising an amino acid sequence of SEQ ID NO:127.

In one embodiment, an antibody that specifically binds to Jagged1/2 is provided, wherein the antibody comprises:
(a) an HVR-H1 comprising the amino acid sequence of SEQ ID NO:95;
(b) an HVR-H2 comprising the amino acid sequence of SEQ ID NO:96;
(c) an HVR-H3 comprising the amino acid sequence of SEQ ID NO:97;
(d) an HVR-L1 comprising the amino acid sequence of SEQ ID NO:123;
(e) an HVR-L2 comprising the amino acid sequence of SEQ ID NO:124; and
(f) an HVR-L3 comprising the amino acid sequence of SEQ ID NO:125.

In one embodiment, an antibody that specifically binds to Jagged1/2 is provided, wherein the antibody comprises:
(a) an HVR-H1 comprising the amino acid sequence of SEQ ID NO:95;
(b) an HVR-H2 comprising the amino acid sequence of SEQ ID NO:96;
(c) an HVR-H3 comprising the amino acid sequence of SEQ ID NO:98;

(d) an HVR-L1 comprising the amino acid sequence of SEQ ID NO:123;

(e) an HVR-L2 comprising the amino acid sequence of SEQ ID NO:124; and (f) an HVR-L3 comprising the amino acid sequence of SEQ ID NO:126.

In another aspect, the invention provides an anti-Jagged1/2 antibody comprising at least one, two, three, four, five, or six HVRs selected from an HVR-H1 comprising an amino acid sequence of SEQ ID NO:105; HVR-H2 comprising the amino acid sequence of SEQ ID NO:106; HVR-H3 comprising an amino acid sequence of SEQ ID N0:109; HVR-L1 comprising the amino acid sequence of SEQ ID NO:128; HVR-L2 comprising the amino acid sequence of SEQ ID NO:129; and HVR-L3 comprising an amino acid sequence of SEQ ID NO:134.

In another embodiment, an antibody that specifically binds to Jagged1/2 is provided, wherein the antibody comprises:

(a) an HVR-H1 comprising the amino acid sequence of SEQ ID NO:100;

(b) an HVR-H2 comprising the amino acid sequence of SEQ ID NO:106;

(c) an HVR-H3 comprising the amino acid sequence of SEQ ID NO:107;

(d) an HVR-L1 comprising the amino acid sequence of SEQ ID NO:128;

(e) an HVR-L2 comprising the amino acid sequence of SEQ ID NO:129; and (f) an HVR-L3 comprising the amino acid sequence of SEQ ID NO:130.

In another embodiment, an antibody that specifically binds to Jagged1/2 is provided, wherein the antibody comprises:

(a) an HVR-H1 comprising the amino acid sequence of SEQ ID NO:100;

(b) an HVR-H2 comprising the amino acid sequence of SEQ ID NO:106;

(c) an HVR-H3 comprising the amino acid sequence of SEQ ID NO:108;

(d) an HVR-L1 comprising the amino acid sequence of SEQ ID NO:128;

(e) an HVR-L2 comprising the amino acid sequence of SEQ ID NO:129; and (f) an HVR-L3 comprising the amino acid sequence of SEQ ID NO:131.

In another embodiment, an antibody that specifically binds to Jagged1/2 is provided, wherein the antibody comprises:

(a) an HVR-H1 comprising the amino acid sequence of SEQ ID NO:101;

(b) an HVR-H2 comprising the amino acid sequence of SEQ ID NO:106;

(c) an HVR-H3 comprising the amino acid sequence of SEQ ID NO:107;

(d) an HVR-L1 comprising the amino acid sequence of SEQ ID NO:128;

(e) an HVR-L2 comprising the amino acid sequence of SEQ ID NO:129; and (f) an HVR-L3 comprising the amino acid sequence of SEQ ID NO:132.

In another embodiment, an antibody that specifically binds to Jagged1/2 is provided, wherein the antibody comprises:

(a) an HVR-H1 comprising the amino acid sequence of SEQ ID NO:102;

(b) an HVR-H2 comprising the amino acid sequence of SEQ ID NO:106;

(c) an HVR-H3 comprising the amino acid sequence of SEQ ID NO:107;

(d) an HVR-L1 comprising the amino acid sequence of SEQ ID NO:128;

(e) an HVR-L2 comprising the amino acid sequence of SEQ ID NO:129; and (f) an HVR-L3 comprising the amino acid sequence of SEQ ID NO:133.

In another embodiment, an antibody that specifically binds to Jagged1/2 is provided, wherein the antibody comprises:

(a) an HVR-H1 comprising the amino acid sequence of SEQ ID NO:103;

(b) an HVR-H2 comprising the amino acid sequence of SEQ ID NO:106;

(c) an HVR-H3 comprising the amino acid sequence of SEQ ID NO:107;

(d) an HVR-L1 comprising the amino acid sequence of SEQ ID NO:128;

(e) an HVR-L2 comprising the amino acid sequence of SEQ ID NO:129; and (f) an HVR-L3 comprising the amino acid sequence of SEQ ID NO:132.

In another embodiment, an antibody that specifically binds to Jagged1/2 is provided, wherein the antibody comprises:

(a) an HVR-H1 comprising the amino acid sequence of SEQ ID NO:104;

(b) an HVR-H2 comprising the amino acid sequence of SEQ ID NO:106;

(c) an HVR-H3 comprising the amino acid sequence of SEQ ID NO:107;

(d) an HVR-L1 comprising the amino acid sequence of SEQ ID NO:128;

(e) an HVR-L2 comprising the amino acid sequence of SEQ ID NO:129; and (f) an HVR-L3 comprising the amino acid sequence of SEQ ID NO:132.

In any of the above embodiments, an anti-Jagged antibody is humanized. In one embodiment, an anti-Jagged antibody comprises HVRs as in any of the above embodiments, and further comprises an acceptor human framework, e.g. a human immunoglobulin framework or a human consensus framework. In another embodiment, an anti-Jagged antibody comprises HVRs as in any of the above embodiments, and further comprises a VH comprising at least one, two, three, or four FRs selected from an FR1 comprising the amino acid sequence of SEQ ID NO:32, 36, 40, 43, 47, 50, or 54; an FR2 comprising the amino acid sequence of SEQ ID NO:33, 37, 41, 44, 48, 51 or 136; an FR3 comprising the amino acid sequence of SEQ ID NO:34, 38, 39, 42, 45, 46, 49, 52, 53, 55, 56, 57, 58, 59; and an FR4 comprising the amino acid sequence of SEQ ID NO:35. In another embodiment, an anti-Jagged antibody comprises HVRs as in any of the above embodiments, and further comprises a VL comprising at least one, two, three, or four FRs selected from an FR1 comprising the amino acid sequence of SEQ ID NO:60, 64, 67, or 70; an FR2 comprising the amino acid sequence of SEQ ID NO:61, 65, 68, or 71; an FR3 comprising the amino acid sequence of SEQ ID NO:62, 66, 69, or 72; and an FR4 comprising the amino acid sequence of SEQ ID NO: 63 or 135.

In another aspect, an anti-Jagged antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:9-17, 29-30 or 73-76. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Jagged antibody comprising that sequence retains the ability to bind to at least one Jagged. In certain embodiments, substitutions, insertions, or deletions occur in regions outside the HVRs (i.e., in the FRs). In certain embodiments, an anti-Jagged antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO:11. Optionally, the anti-Jagged antibody comprises the VH sequence in SEQ ID NO:11, including post-translational modifications of that sequence. In a particular embodiment, the VH comprises one, two or three HVRs selected from: (a) HVR-H1 comprising the amino acid sequence of SEQ ID NO:81, (b) HVR-H2 comprising the amino acid sequence of SEQ ID NO:83, and (c) HVR-H3 comprising the amino acid sequence of SEQ ID NO:85.

In another aspect, an anti-Jagged antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO:18-28 or 77-80. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-Jagged antibody comprising that sequence retains the ability to bind to Jagged. In certain embodiments, a total of 1 to 10 amino acids have been substituted, inserted and/or deleted in SEQ ID NO:20. In certain embodiments, the substitutions, insertions, or deletions occur in regions outside the HVRs (i.e., in the FRs). Optionally, the anti-Jagged antibody comprises the VL sequence in SEQ ID NO:20, including post-translational modifications of that sequence. In a particular embodiment, the VL comprises one, two or three HVRs selected from (a) HVR-L1 comprising the amino acid sequence of SEQ ID NO:110; (b) HVR-L2 comprising the amino acid sequence of SEQ ID NO:111; and (c) HVR-L3 comprising the amino acid sequence of SEQ ID NO:112.

In another aspect, an anti-Jagged antibody is provided, wherein the antibody comprises a VH as in any of the embodiments provided above, and a VL as in any of the embodiments provided above. In one embodiment, the antibody comprises the VH and VL sequences in SEQ ID NO:10 and SEQ ID NO:19, respectively, including post-translational modifications of those sequences. In one embodiment, the antibody comprises the VH and VL sequences in SEQ ID NO:11 and SEQ ID NO:20, respectively, including post-translational modifications of those sequences. In one embodiment, the antibody comprises the VH and VL sequences in SEQ ID NO:15 and SEQ ID NO:24, respectively, including post-translational modifications of those sequences.

In a further aspect, the invention provides an antibody that binds to the same epitope as an anti-Jagged antibody provided herein. For example, in certain embodiments, an antibody is provided that binds to the same epitope as an anti-Jagged1 antibody comprising a VH sequence of SEQ ID NO:10 and a VL sequence of SEQ ID NO:19. In another embodiments, an antibody is provided that binds to the same epitope as an anti-Jagged1 antibody comprising a VH sequence of SEQ ID NO:11 and a VL sequence of SEQ ID NO:20. In another embodiments, an antibody is provided that binds to the same epitope as an anti-Jagged2 antibody comprising a VH sequence of SEQ ID NO:15 and a VL sequence of SEQ ID NO:24.

In certain embodiments, an antibody is provided that binds to an epitope within a murine Jag1-DSL-EGF1-4 peptide of SEQ ID NO:5. In certain embodiments, an antibody is provided that binds to an epitope within a human Jag1-DSL-EGF1-4 peptide of SEQ ID NO:6. In certain embodiments, an antibody is provided that binds to an epitope within a murine Jag2-DSL-EGF1-4 peptide of SEQ ID NO:7. In certain embodiments, an antibody is provided that binds to an epitope within a human Jag2-DSL-EGF1-4 peptide of SEQ ID NO:8.

In a further aspect, the invention provides an antibody that competes for binding with any of the antibodies provided herein.

In a further aspect of the invention, an anti-Jagged antibody according to any of the above embodiments is a monoclonal antibody, including a chimeric, humanized or human antibody. In one embodiment, an anti-Jagged antibody is an antibody fragment, e.g., a Fv, Fab, Fab', scFv, diabody, or F(ab')$_2$ fragment. In another embodiment, the antibody is a full length antibody, e.g., an intact human IgG1 antibody or other antibody class or isotype as defined herein.

In a further aspect, an anti-Jagged antibody according to any of the above embodiments may incorporate any of the features, singly or in combination, as described in Sections 1-7 below:

1. Antibody Affinity

In certain embodiments, an antibody provided herein has a dissociation constant (Kd) of ≤1 µM, ≤100 nM, ≤10 nM, ≤1 nM, ≤0.1 nM, ≤0.01 nM, or ≤0.001 nM (e.g. $10^{-8}$ M or less, e.g. from $10^{-8}$ M to $10^{-13}$ M, e.g., from $10^{-9}$ M to $10^{-13}$ M).

In one embodiment, Kd is measured by a radiolabeled antigen binding assay (RIA). In one embodiment, an RIA is performed with the Fab version of an antibody of interest and its antigen. For example, solution binding affinity of Fabs for antigen is measured by equilibrating Fab with a minimal concentration of ($^{125}$I)-labeled antigen in the presence of a titration series of unlabeled antigen, then capturing bound antigen with an anti-Fab antibody-coated plate (see, e.g., Chen et al., *J. Mol. Biol.* 293:865-881 (1999)). To establish conditions for the assay, MICROTITER® multi-well plates (Thermo Scientific) are coated overnight with 5 µg/ml of a capturing anti-Fab antibody (Cappel Labs) in 50 mM sodium carbonate (pH 9.6), and subsequently blocked with 2% (w/v) bovine serum albumin in PBS for two to five hours at room temperature (approximately 23° C.). In a non-adsorbent plate (Nunc #269620), 100 pM or 26 pM [$^{125}$I]-antigen antigen are mixed with serial dilutions of a Fab of interest (e.g., consistent with assessment of the anti-VEGF antibody, Fab-12, in Presta et al., *Cancer Res.* 57:4593-4599 (1997)). The Fab of interest is then incubated overnight; however, the incubation may continue for a longer period (e.g., about 65 hours) to ensure that equilibrium is reached. Thereafter, the mixtures are transferred to the capture plate for incubation at room temperature (e.g., for one hour). The solution is then removed and the plate washed eight times with 0.1% polysorbate 20 (TWEEN-20) in PBS. When the plates have dried, 150 µl/well of scintillant (MICROSCINT-20™; Packard) is added, and the plates are counted on a TOPCOUNT™ gamma counter (Packard) for ten minutes. Concentrations of each Fab that give less than or equal to 20% of maximal binding are chosen for use in competitive binding assays.

According to another embodiment, Kd is measured using a BIACORE® surface plasmon resonance assay. For example, an assay using a BIACORE®-2000 or a BIA-CORE®-3000 (BIAcore, Inc., Piscataway, N.J.) is performed at 25° C. with immobilized antigen CM5 chips at ~10 response units (RU). In one embodiment, carboxymethylated dextran biosensor chips (CM5, BIACORE, Inc.) are activated with N-ethyl-N'-(3-dimethylaminopropyl)-carbodiimide hydrochloride (EDC) and N-hydroxysuccinimide (NHS) according to the supplier's instructions. Antigen is diluted with 10 mM sodium acetate, pH 4.8, to 5 µg/ml (~0.2 µM) before injection at a flow rate of 5 µl/minute to achieve approximately 10 response units (RU) of coupled protein. Following the injection of antigen, 1 M ethanolamine is injected to block unreacted groups. For kinetics measurements, two-fold serial dilutions of Fab (0.78 nM to 500 nM) are injected in PBS with 0.05% polysorbate 20 (TWEEN-20™) surfactant (PBST) at 25° C. at a flow rate of approximately 25 µl/min. Association rates ($k_{on}$) and dissociation rates ($k_{off}$) are calculated using a simple one-to-one Langmuir binding model (BIACORE® Evaluation Software version 3.2) by simultaneously fitting the association and dissociation sensorgrams. The equilibrium dissociation constant (Kd) is calculated as the ratio $k_{off}/k_{on}$. See, e.g., Chen et al., *J. Mol. Biol.* 293:865-881 (1999). If the on-rate exceeds $10^6$ $M^{-1}$ $s^{-1}$ by the surface plasmon resonance assay above, then the on-rate can be determined by using a fluorescent quenching technique that measures the increase or decrease in fluorescence emission intensity (excitation=295 nm; emission=340 nm, 16 nm band-pass) at 25° C. of a 20 nM anti-antigen antibody (Fab form) in PBS, pH 7.2, in the presence of increasing concentrations of antigen as measured in a spectrometer, such as a stop-flow equipped spectrophotometer (Aviv Instruments) or a 8000-series SLM-AMINCO™ spectrophotometer (ThermoSpectronic) with a stirred cuvette.

2. Antibody Fragments

In certain embodiments, an antibody provided herein is an antibody fragment. Antibody fragments include, but are not limited to, Fab, Fab', Fab'-SH, F(ab')$_2$, Fv, and scFv fragments, and other fragments described below. For a review of certain antibody fragments, see Hudson et al. *Nat. Med.* 9:129-134 (2003). For a review of scFv fragments, see, e.g., Plückthun, in *The Pharmacology of Monoclonal Antibodies*, vol. 113, Rosenburg and Moore eds., (Springer-Verlag, New York), pp. 269-315 (1994); see also WO 93/16185; and U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 404,097; WO 1993/01161; Hudson et al., *Nat. Med.* 9:129-134 (2003); and Hollinger et al., *Proc. Natl. Acad. Sci. USA* 90: 6444-6448 (1993). Triabodies and tetrabodies are also described in Hudson et al., *Nat. Med.* 9:129-134 (2003).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516 B1).

Antibody fragments can be made by various techniques, including but not limited to proteolytic digestion of an intact antibody as well as production by recombinant host cells (e.g. *E. coli* or phage), as described herein.

3. Chimeric and Humanized Antibodies

In certain embodiments, an antibody provided herein is a chimeric antibody. Certain chimeric antibodies are described, e.g., in U.S. Pat. No. 4,816,567; and Morrison et al., *Proc. Natl. Acad. Sci. USA*, 81:6851-6855 (1984)). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro and Fransson, *Front. Biosci.* 13:1619-1633 (2008), and are further described, e.g., in Riechmann et al., *Nature* 332:323-329 (1988); Queen et al., *Proc. Nat'l Acad. Sci. USA* 86:10029-10033 (1989); U.S. Pat. Nos. 5,821,337, 7,527,791, 6,982,321, and 7,087,409; Kashmiri et al., *Methods* 36:25-34 (2005) (describing specificity determining region (SDR) grafting); Padlan, *Mol. Immunol.* 28:489-498 (1991) (describing "resurfacing"); Dall'Acqua et al., *Methods* 36:43-60 (2005) (describing "FR shuffling"); and Osbourn et al., *Methods* 36:61-68 (2005) and Klimka et al., *Br. J. Cancer,* 83:252-260 (2000) (describing the "guided selection" approach to FR shuffling).

Human framework regions that may be used for humanization include but are not limited to: framework regions selected using the "best-fit" method (see, e.g., Sims et al. *J. Immunol.* 151:2296 (1993)); framework regions derived from the consensus sequence of human antibodies of a particular subgroup of light or heavy chain variable regions (see, e.g., Carter et al. *Proc. Natl. Acad. Sci. USA,* 89:4285 (1992); and Presta et al. *J. Immunol.,* 151:2623 (1993)); human mature (somatically mutated) framework regions or human germline framework regions (see, e.g., Almagro and Fransson, *Front. Biosci.* 13:1619-1633 (2008)); and framework regions derived from screening FR libraries (see, e.g., Baca et al., *J. Biol. Chem.* 272:10678-10684 (1997) and Rosok et al., *J. Biol. Chem.* 271:22611-22618 (1996)).

4. Human Antibodies

In certain embodiments, an antibody provided herein is a human antibody. Human antibodies can be produced using various techniques known in the art. Human antibodies are described generally in van Dijk and van de Winkel, *Curr. Opin. Pharmacol.* 5: 368-74 (2001) and Lonberg, *Curr. Opin. Immunol.* 20:450-459 (2008).

Human antibodies may be prepared by administering an immunogen to a transgenic animal that has been modified to produce intact human antibodies or intact human antibodies with human variable regions in response to antigenic challenge. Such animals typically contain all or a portion of the human immunoglobulin loci, which replace the endogenous immunoglobulin loci, or which are present extrachromosomally or integrated randomly into the animal's chromosomes. In such transgenic mice, the endogenous immunoglobulin loci have generally been inactivated. For review of methods for obtaining human antibodies from transgenic animals, see Lonberg, Nat. Biotech. 23:1117-1125 (2005). See also, e.g., U.S. Pat. Nos. 6,075,181 and 6,150,584 describing XENO-MOUSE™ technology; U.S. Pat. No. 5,770,429 describing HUMAB® technology; U.S. Pat. No. 7,041,870 describing K-M MOUSE® technology, and U.S. Patent Application Publication No. US 2007/0061900, describing VELOCI-MOUSE® technology). Human variable regions from intact antibodies generated by such animals may be further modified, e.g., by combining with a different human constant region.

Human antibodies can also be made by hybridoma-based methods. Human myeloma and mouse-human heteromyeloma cell lines for the production of human monoclonal antibodies have been described. (See, e.g., Kozbor J. Immunol., 133: 3001 (1984); Brodeur et al., Monoclonal Antibody Production Techniques and Applications, pp. 51-63 (Marcel Dekker, Inc., New York, 1987); and Boerner et al., J. Immunol., 147: 86 (1991).) Human antibodies generated via human B-cell hybridoma technology are also described in Li et al., Proc. Natl. Acad. Sci., USA, 103:3557-3562 (2006). Additional methods include those described, for example, in U.S. Pat. No. 7,189,826 (describing production of monoclonal human IgM antibodies from hybridoma cell lines) and Ni, Xiandai Mianyixue, 26(4):265-268 (2006) (describing human-human hybridomas). Human hybridoma technology (Trioma technology) is also described in Vollmers and Brandlein, Histology and Histopathology, 20(3):927-937 (2005) and Vollmers and Brandlein, Methods and Findings in Experimental and Clinical Pharmacology, 27(3):185-91 (2005).

Human antibodies may also be generated by isolating Fv clone variable domain sequences selected from human-derived phage display libraries. Such variable domain sequences may then be combined with a desired human constant domain. Techniques for selecting human antibodies from antibody libraries are described below.

5. Library-Derived Antibodies

Antibodies of the invention may be isolated by screening combinatorial libraries for antibodies with the desired activity or activities. For example, a variety of methods are known in the art for generating phage display libraries and screening such libraries for antibodies possessing the desired binding characteristics. Such methods are reviewed, e.g., in Hoogenboom et al. in Methods in Molecular Biology 178: 1-37 (O'Brien et al., ed., Human Press, Totowa, N.J., 2001) and further described, e.g., in the McCafferty et al., Nature 348:552-554; Clackson et al., Nature 352: 624-628 (1991); Marks et al., J. Mol. Biol. 222: 581-597 (1992); Marks and Bradbury, in Methods in Molecular Biology 248:161-175 (Lo, ed., Human Press, Totowa, N.J., 2003); Sidhu et al., J. Mol. Biol. 338(2): 299-310 (2004); Lee et al., J. Mol. Biol. 340(5): 1073-1093 (2004); Fellouse, Proc. Natl. Acad. Sci. USA 101(34): 12467-12472 (2004); and Lee et al., J. Immunol. Methods 284(1-2): 119-132 (2004).

In certain phage display methods, repertoires of VH and VL genes are separately cloned by polymerase chain reaction (PCR) and recombined randomly in phage libraries, which can then be screened for antigen-binding phage as described in Winter et al., Ann. Rev. Immunol., 12: 433-455 (1994). Phage typically display antibody fragments, either as single-chain Fv (scFv) fragments or as Fab fragments. Libraries from immunized sources provide high-affinity antibodies to the immunogen without the requirement of constructing hybridomas. Alternatively, the naive repertoire can be cloned (e.g., from human) to provide a single source of antibodies to a wide range of non-self and also self antigens without any immunization as described by Griffiths et al., EMBO J, 12: 725-734 (1993). Finally, naive libraries can also be made synthetically by cloning unrearranged V-gene segments from stem cells, and using PCR primers containing random sequence to encode the highly variable CDR3 regions and to accomplish rearrangement in vitro, as described by Hoogenboom and Winter, J. Mol. Biol., 227: 381-388 (1992). Patent publications describing human antibody phage libraries include, for example: U.S. Pat. No. 5,750,373, and US Patent Publication Nos. 2005/0079574, 2005/0119455, 2005/0266000, 2007/0117126, 2007/0160598, 2007/0237764, 2007/0292936, and 2009/0002360.

Antibodies or antibody fragments isolated from human antibody libraries are considered human antibodies or human antibody fragments herein.

6. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for Jagged and the other is for any other antigen. In certain embodiments, bispecific antibodies may bind to two different epitopes of Jagged. Bispecific antibodies may also be used to localize cytotoxic agents to cells which express Jagged. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein and Cuello, Nature 305: 537 (1983)), WO 93/08829, and Traunecker et al., EMBO J. 10: 3655 (1991)), and "knob-in-hole" engineering (see, e.g., U.S. Pat. No. 5,731,168). Multi-specific antibodies may also be made by engineering electrostatic steering effects for making antibody Fc-heterodimeric molecules (WO 2009/089004A1); cross-linking two or more antibodies or fragments (see, e.g., U.S. Pat. No. 4,676,980, and Brennan et al., Science, 229: 81 (1985)); using leucine zippers to produce bi-specific antibodies (see, e.g., Kostelny et al., J. Immunol., 148(5):1547-1553 (1992)); using "diabody" technology for making bispecific antibody fragments (see, e.g., Hollinger et al., Proc. Natl. Acad. Sci. USA, 90:6444-6448 (1993)); and using single-chain Fv (sFv) dimers (see, e.g. Gruber et al., J. Immunol., 152:5368 (1994)); and preparing trispecific antibodies as described, e.g., in Tutt et al. J. Immunol. 147: 60 (1991).

Engineered antibodies with three or more functional antigen binding sites, including "Octopus antibodies," are also included herein (see, e.g. US 2006/0025576A1).

The antibody or fragment herein also includes a "Dual Acting FAb" or "DAF" comprising an antigen binding site that binds to Jagged as well as another, different antigen (see, US 2008/0069820, for example).

7. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions." More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
|---|---|---|
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, *Methods Mol. Biol.* 207:179-196 (2008)), and/or residues that contact antigen, with the resulting variant VH or VL being tested for binding affinity. Affinity maturation by constructing and reselecting from secondary libraries has been described, e.g., in Hoogenboom et al. in *Methods in Molecular Biology* 178:1-37 (O'Brien et al., ed., Human Press, Totowa, N.J., (2001).) In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham and Wells (1989) *Science*, 244:1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc region, the carbohydrate attached thereto may be altered. Native antibodies produced by mammalian cells typically comprise a branched, biantennary oligosaccharide that is generally attached by an N-linkage to Asn297 of the CH2 domain of the Fc region. See, e.g., Wright et al. *TIBTECH* 15:26-32 (1997). The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e.g. complex, hybrid and high mannose structures) as measured by MALDI-TOF mass spectrometry, as described in WO 2008/077546, for example. Asn297 refers to the asparagine residue located at about position 297 in the Fc region (Eu numbering of Fc region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US Patent Publication Nos. US 2003/0157108 (Presta, L.); US 2004/0093621 (Kyowa Hakko Kogyo Co., Ltd). Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO2005/053742; WO2002/031140; Okazaki et al. *J. Mol. Biol.* 336:1239-1249 (2004); Yamane-Ohnuki et al. *Biotech. Bioeng.* 87: 614 (2004). Examples of cell lines capable of producing defucosylated antibodies include Lec13 CHO cells deficient in protein fucosylation (Ripka et al. *Arch. Biochem. Biophys.* 249:533-545 (1986); US Pat Appl No US 2003/0157108 A1, Presta, L; and WO 2004/056312 A1, Adams et al., especially at Example 11), and knockout cell lines, such as alpha-1,6-fucosyltransferase gene, FUT8, knockout CHO cells (see, e.g., Yamane-Ohnuki et al. *Biotech. Bioeng.* 87: 614 (2004); Kanda, Y. et al., *Biotechnol. Bioeng.*, 94(4):680-688 (2006); and WO2003/085107).

Antibodies variants are further provided with bisected oligosaccharides, e.g., in which a biantennary oligosaccharide attached to the Fc region of the antibody is bisected by GlcNAc. Such antibody variants may have reduced fucosylation and/or improved ADCC function. Examples of such antibody variants are described, e.g., in WO 2003/011878 (Jean-Mairet et al.); U.S. Pat. No. 6,602,684 (Umana et al.); and US 2005/0123546 (Umana et al.). Antibody variants with at least one galactose residue in the oligosaccharide attached to the Fc region are also provided. Such antibody variants may have improved CDC function. Such antibody variants are described, e.g., in WO 1997/30087 (Patel et al.); WO 1998/58964 (Raju, S.); and WO 1999/22764 (Raju, S.).

c) Fc Region Variants

In certain embodiments, one or more amino acid modifications may be introduced into the Fc region of an antibody provided herein, thereby generating an Fc region variant. The Fc region variant may comprise a human Fc region sequence (e.g., a human IgG1, IgG2, IgG3 or IgG4 Fc region) comprising an amino acid modification (e.g. a substitution) at one or more amino acid positions.

In certain embodiments, the invention contemplates an antibody variant that possesses some but not all effector functions, which make it a desirable candidate for applications in which the half life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc (RIII only, whereas monocytes express Fc (RI, Fc (RII and Fc (RIII. FcR expression on hematopoietic cells is summarized in Table 3 on page 464 of Ravetch and Kinet, *Annu. Rev. Immunol.* 9:457-492 (1991). Non-limiting examples of in vitro assays to assess ADCC activity of a molecule of interest is described in U.S. Pat. No. 5,500,362 (see, e.g. Hellstrom, I. et al. *Proc. Nat'l Acad. Sci. USA* 83:7059-7063 (1986)) and Hellstrom, I et al., *Proc. Nat'l Acad. Sci. USA* 82:1499-1502 (1985); U.S. Pat. No. 5,821,337 (see Bruggemann, M. et al., *J. Exp. Med.* 166:1351-1361 (1987)). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in a animal model such as that disclosed in Clynes et al. Proc. Nat'l Acad. Sci. USA 95:652-656 (1998). C1q binding assays may also be carried out to confirm that the antibody is unable to bind C1q and hence lacks CDC activity. See, e.g., C1q and C3c binding ELISA in WO 2006/029879 and WO 2005/100402. To assess complement activation, a CDC assay may be performed (see, for example, Gazzano-Santoro et al., *J. Immunol. Methods* 202:163 (1996); Cragg, M. S. et al., *Blood* 101:1045-1052 (2003); and Cragg, M. S. and M. J. Glennie, *Blood* 103:2738-2743 (2004)). FcRn binding and in vivo clearance/half life determinations can also be performed using methods known in the art (see, e.g., Petkova, S. B. et al., *Int'l. Immunol.* 18(12):1759-1769 (2006)).

Antibodies with reduced effector function include those with substitution of one or more of Fc region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No.

6,737,056; WO 2004/056312, and Shields et al., *J. Biol. Chem.* 9(2): 6591-6604 (2001).)

In certain embodiments, an antibody variant comprises an Fc region with one or more amino acid substitutions which improve ADCC, e.g., substitutions at positions 298, 333, and/or 334 of the Fc region (EU numbering of residues).

In some embodiments, alterations are made in the Fc region that result in altered (i.e., either improved or diminished) C1q binding and/or Complement Dependent Cytotoxicity (CDC), e.g., as described in U.S. Pat. No. 6,194,551, WO 99/51642, and Idusogie et al. *J. Immunol.* 164: 4178-4184 (2000).

Antibodies with increased half lives and improved binding to the neonatal Fc receptor (FcRn), which is responsible for the transfer of maternal IgGs to the fetus (Guyer et al., *J. Immunol.* 117:587 (1976) and Kim et al., *J. Immunol.* 24:249 (1994)), are described in US2005/0014934A1 (Hinton et al.). Those antibodies comprise an Fc region with one or more substitutions therein which improve binding of the Fc region to FcRn. Such Fc variants include those with substitutions at one or more of Fc region residues: 238, 256, 265, 272, 286, 303, 305, 307, 311, 312, 317, 340, 356, 360, 362, 376, 378, 380, 382, 413, 424 or 434, e.g., substitution of Fc region residue 434 (U.S. Pat. No. 7,371,826).

See also Duncan & Winter, *Nature* 322:738-40 (1988); U.S. Pat. No. 5,648,260; U.S. Pat. No. 5,624,821; and WO 94/29351 concerning other examples of Fc region variants.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc region. Cysteine engineered antibodies may be generated as described, e.g., in U.S. Pat. No. 7,521,541.

e) Antibody Derivatives

In certain embodiments, an antibody provided herein may be further modified to contain additional nonproteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1,3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer are attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and nonproteinaceous moiety that may be selectively heated by exposure to radiation are provided. In one embodiment, the nonproteinaceous moiety is a carbon nanotube (Kam et al., *Proc. Natl. Acad. Sci. USA* 102: 11600-11605 (2005)). The radiation may be of any wavelength, and includes, but is not limited to, wavelengths that do not harm ordinary cells, but which heat the nonproteinaceous moiety to a temperature at which cells proximal to the antibody-nonproteinaceous moiety are killed.

B. Recombinant Methods and Compositions

Antibodies may be produced using recombinant methods and compositions, e.g., as described in U.S. Pat. No. 4,816,567. In one embodiment, isolated nucleic acid encoding an anti-Jagged antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-Jagged antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-Jagged antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, Methods in Molecular Biology, Vol. 248 (B. K. C. Lo, ed., Humana Press, Totowa, N.J., 2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, *Nat. Biotech.* 22:1409-1414 (2004), and Li et al., *Nat. Biotech.* 24:210-215 (2006).

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham et al., *J. Gen Virol.* 36:59 (1977)); baby hamster kidney cells (BHK); mouse sertoli cells (TM4 cells as described, e.g., in Mather, *Biol. Reprod.* 23:243-251 (1980)); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather et al., Annals N.Y. Acad. Sci. 383:44-68 (1982); MRC 5 cells; and FS4 cells. Other useful mammalian host cell lines include Chinese hamster ovary (CHO) cells, including DHFR⁻ CHO cells (Urlaub et al., *Proc. Natl. Acad. Sci. USA* 77:4216 (1980)); and myeloma cell lines such as Y0, NS0 and Sp2/0. For a review of certain mammalian host cell lines suitable for antibody production, see, e.g., Yazaki and Wu, *Methods in Molecular Biology*, Vol. 248 (B. K. C. Lo, ed., Humana Press, Totowa, N.J.), pp. 255-268 (2003).

C. Assays

Anti-Jagged antibodies provided herein may be identified, screened for, or characterized for their physical/chemical properties and/or biological activities by various assays known in the art.

1. Binding Assays and Other Assays

In one aspect, an antibody of the invention is tested for its antigen binding activity, e.g., by known methods such as ELISA, Western blot, etc.

In another aspect, competition assays may be used to identify an antibody that competes with antibody A, A-1, A-2, C, C-1, D, D-1, D-2, D-3, D-4 and D-5 for binding to human or murine Jagged1. In another aspect, competition assays may be used to identify an antibody that competes with antibody B, B-1, B-2, B-3, C, C-1, D, D-1, D-2, D-3, D-4 and D-5 for binding to human or murine Jagged2. In certain embodiments, such a competing antibody binds to the same epitope (e.g., a linear or a conformational epitope) that is bound by A, A-1, A-2, B, B-1, B-2, B-3, C, C-1, D, D-1, D-2, D-3, D-4 or D-5.

Detailed exemplary methods for mapping an epitope to which an antibody binds are provided in Morris (1996) "Epitope Mapping Protocols," in Methods in Molecular Biology vol. 66 (Humana Press, Totowa, N.J.).

In an exemplary competition assay, immobilized Jagged1 or Jagged2 is incubated in a solution comprising a first labeled antibody that binds to Jagged1 or Jagged2 (e.g., A, A-1, A-2, B, B-1, B-2, B-3, C, C-1, D, D-1, D-2, D-3, D-4 or D-5) and a second unlabeled antibody that is being tested for its ability to compete with the first antibody for binding to Jagged1 or Jagged2. The second antibody may be present in a hybridoma supernatant. As a control, immobilized Jagged1 or Jagged2 is incubated in a solution comprising the first labeled antibody but not the second unlabeled antibody. After incubation under conditions permissive for binding of the first antibody to Jagged1 or Jagged2, excess unbound antibody is removed, and the amount of label associated with immobilized Jagged1 or Jagged2 is measured. If the amount of label associated with immobilized Jagged1 or Jagged2 is substantially reduced in the test sample relative to the control sample, then that indicates that the second antibody is competing with the first antibody for binding to Jagged1 or Jagged2. See Harlow and Lane (1988) *Antibodies: A Laboratory Manual* ch. 14 (Cold Spring Harbor Laboratory, Cold Spring Harbor, N.Y.).

2. Activity Assays

In one aspect, assays are provided for identifying anti-Jagged antibodies thereof having biological activity. Biological activity may include, e.g., inhibition of Jagged1- or Jagged2-induced cell signaling through a Notch receptor, such as inhibition of Jagged1-induced signaling through Notch1. An exemplary assay is provided in the Examples. In certain other embodiments, an antibody of the invention is tested for its ability to inhibit expression of a reporter gene that is responsive to Jagged1-induced Notch signaling. An exemplary assay is provided in the Examples. In certain embodiments, an antibody of the invention is tested for such biological activity. Antibodies having such biological activity in vivo and/or in vitro are also provided.

D. Immunoconjugates

The invention also provides immunoconjugates comprising an anti-Jagged antibody herein conjugated to one or more cytotoxic agents, such as chemotherapeutic agents or drugs, growth inhibitory agents, toxins (e.g., protein toxins, enzymatically active toxins of bacterial, fungal, plant, or animal origin, or fragments thereof), or radioactive isotopes.

In one embodiment, an immunoconjugate is an antibody-drug conjugate (ADC) in which an antibody is conjugated to one or more drugs, including but not limited to a maytansinoid (see U.S. Pat. Nos. 5,208,020, 5,416,064 and European Patent EP 0 425 235 B1); an auristatin such as monomethylauristatin drug moieties DE and DF (MMAE and MMAF) (see U.S. Pat. Nos. 5,635,483 and 5,780,588, and 7,498, 298); a dolastatin; a calicheamicin or derivative thereof (see U.S. Pat. Nos. 5,712,374, 5,714,586, 5,739,116, 5,767,285, 5,770,701, 5,770,710, 5,773,001, and 5,877,296; Hinman et al., *Cancer Res.* 53:3336-3342 (1993); and Lode et al., *Cancer Res.* 58:2925-2928 (1998)); an anthracycline such as daunomycin or doxorubicin (see Kratz et al., *Current Med. Chem.* 13:477-523 (2006); Jeffrey et al., *Bioorganic & Med. Chem. Letters* 16:358-362 (2006); Torgov et al., Bioconj. Chem. 16:717-721 (2005); Nagy et al., *Proc. Natl. Acad. Sci. USA* 97:829-834 (2000); Dubowchik et al., *Bioorg. & Med. Chem. Letters* 12:1529-1532 (2002); King et al., *J. Med. Chem.* 45:4336-4343 (2002); and U.S. Pat. No. 6,630,579); methotrexate; vindesine; a taxane such as docetaxel, paclitaxel, larotaxel, tesetaxel, and ortataxel; a trichothecene; and CC1065.

In another embodiment, an immunoconjugate comprises an antibody as described herein conjugated to an enzymatically active toxin or fragment thereof, including but not limited to diphtheria A chain, nonbinding active fragments of diphtheria toxin, exotoxin A chain (from *Pseudomonas aeruginosa*), ricin A chain, abrin A chain, modeccin A chain, alpha-sarcin, *Aleurites fordii* proteins, dianthin proteins, *Phytolaca americana* proteins (PAPI, PAPII, and PAP-S), *momordica charantia* inhibitor, curcin, crotin, *sapaonaria officinalis* inhibitor, gelonin, mitogellin, restrictocin, phenomycin, enomycin, and the tricothecenes.

In another embodiment, an immunoconjugate comprises an antibody as described herein conjugated to a radioactive atom to form a radioconjugate. A variety of radioactive isotopes are available for the production of radioconjugates. Examples include $At^{211}$, $I^{131}$, $I^{125}$, $Y^{90}$, $Re^{186}$, $Re^{188}$, $Sm^{153}$, $Bi^{212}$, $P^{32}$, $Pb^{212}$ and radioactive isotopes of Lu. When the radioconjugate is used for detection, it may comprise a radioactive atom for scintigraphic studies, for example tc99m or I123, or a spin label for nuclear magnetic resonance (NMR) imaging (also known as magnetic resonance imaging, mri), such as iodine-123 again, iodine-131, indium-111, fluorine-19, carbon-13, nitrogen-15, oxygen-17, gadolinium, manganese or iron.

Conjugates of an antibody and cytotoxic agent may be made using a variety of bifunctional protein coupling agents such as N-succinimidyl-3-(2-pyridyldithio) propionate (SPDP), succinimidyl-4-(N-maleimidomethyl) cyclohexane-1-carboxylate (SMCC), iminothiolane (IT), bifunctional derivatives of imidoesters (such as dimethyl adipimidate HCl), active esters (such as disuccinimidyl suberate), aldehydes (such as glutaraldehyde), bis-azido compounds (such as bis(p-azidobenzoyl) hexanediamine), bis-diazonium derivatives (such as bis-(p-diazoniumbenzoyl)-ethylenediamine), diisocyanates (such as toluene 2,6-diisocyanate), and bis-active fluorine compounds (such as 1,5-difluoro-2,4-dinitrobenzene). For example, a ricin immunotoxin can be prepared as described in Vitetta et al., *Science* 238:1098 (1987). Carbon-14-labeled 1-isothiocyanatobenzyl-3-methyldiethylene triaminepentaacetic acid (MX-DTPA) is an exemplary chelating agent for conjugation of radionucleotide to the antibody. See WO94/11026. The linker may be a "cleavable linker" facilitating release of a cytotoxic drug in the cell. For example, an acid-labile linker, peptidase-sensitive linker, photolabile linker, dimethyl linker or disulfide-containing linker (Chari et al., *Cancer Res.* 52:127-131 (1992); U.S. Pat. No. 5,208,020) may be used.

The immunuoconjugates or ADCs herein expressly contemplate, but are not limited to such conjugates prepared with cross-linker reagents including, but not limited to, BMPS, EMCS, GMBS, HBVS, LC-SMCC, MBS, MPBH, SBAP, SIA, SIAB, SMCC, SMPB, SMPH, sulfo-EMCS, sulfo-GMBS, sulfo-KMUS, sulfo-MBS, sulfo-SIAB, sulfo-SMCC, and sulfo-SMPB, and SVSB (succinimidyl-(4-vinylsulfone)benzoate) which are commercially available (e.g., from Pierce Biotechnology, Inc., Rockford, Ill., U.S.A).

E. Methods and Compositions for Diagnostics and Detection

In certain embodiments, any of the anti-Jagged1 antibodies provided herein is useful for detecting the presence of Jagged1 in a biological sample. In certain embodiments, any of the anti-Jagged2 antibodies provided herein is useful for detecting the presence of Jagged2 in a biological sample. The term "detecting" as used herein encompasses quantitative or qualitative detection. In certain embodiments, a biological sample comprises a cell or tissue, such as cancerous tissues.

In one embodiment, an anti-Jagged antibody for use in a method of diagnosis or detection is provided. In a further aspect, a method of detecting the presence of Jagged1 in a biological sample is provided. In a further aspect, a method of detecting the presence of Jagged2 in a biological sample is provided. In certain embodiments, the method comprises contacting the biological sample with an anti-Jagged1 antibody or with an anti-Jagged2 antibody as described herein under conditions permissive for binding of the anti-Jagged1 antibody or the anti-Jagged2 antibody to Jagged1 and Jagged2, respectively, and detecting whether a complex is formed between the anti-Jagged1 antibody and Jagged1, or between the anti-Jagged2 antibody and Jagged2. Such method may be an in vitro or in vivo method. In one embodiment, an anti-Jagged1 antibody is used to select subjects eligible for therapy with an anti-Jagged1 antibody, e.g. where Jagged1 is a biomarker for selection of patients. In one embodiment, an anti-Jagged2 antibody is used to select subjects eligible for therapy with an anti-Jagged2 antibody, e.g. where Jagged2 is a biomarker for selection of patients.

Exemplary disorders that may be diagnosed using an antibody of the invention include cancer, e.g., breast cancer, lung cancer, brain cancer, cervical cancer, colon cancer, liver cancer, bile duct cancer, pancreatic cancer, skin cancer, B-cell malignancies, and T-cell malignancies.

In certain embodiments, labeled anti-Jagged antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luceriferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

F. Pharmaceutical Formulations

Pharmaceutical formulations of an anti-Jagged antibody as described herein are prepared by mixing such antibody having the desired degree of purity with one or more optional pharmaceutically acceptable carriers (*Remington's Pharmaceutical Sciences* 16th edition, Osol, A. Ed. (1980)), in the form of lyophilized formulations or aqueous solutions. Pharmaceutically acceptable carriers are generally nontoxic to recipients at the dosages and concentrations employed, and include, but are not limited to: buffers such as phosphate, citrate, and other organic acids; antioxidants including ascorbic acid and methionine; preservatives (such as octadecyldimethylbenzyl ammonium chloride; hexamethonium chloride; benzalkonium chloride; benzethonium chloride; phenol, butyl or benzyl alcohol; alkyl parabens such as methyl or propyl paraben; catechol; resorcinol; cyclohexanol; 3-pentanol; and m-cresol); low molecular weight (less than about 10 residues) polypeptides; proteins, such as serum albumin, gelatin, or immunoglobulins; hydrophilic polymers such as polyvinylpyrrolidone; amino acids such as glycine, glutamine, asparagine, histidine, arginine, or lysine; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes (e.g. Zn-protein complexes); and/or non-ionic surfactants such as polyethylene glycol (PEG). Exemplary pharmaceutically acceptable carriers herein further include insterstitial drug dispersion agents such as soluble neutral-active hyaluronidase glycoproteins (sHASEGP), for example, human soluble PH-20 hyaluronidase glycoproteins, such as rHuPH20 (HYLENEX®, Baxter International, Inc.). Certain exemplary sHASEGPs and methods of use, including rHuPH20, are described in US Patent Publication Nos. 2005/0260186 and 2006/0104968. In one aspect, a sHASEGP is combined with one or more additional glycosaminoglycanases such as chondroitinases.

Exemplary lyophilized antibody formulations are described in U.S. Pat. No. 6,267,958. Aqueous antibody formulations include those described in U.S. Pat. No. 6,171,586 and WO2006/044908, the latter formulations including a histidine-acetate buffer.

The formulation herein may also contain more than one active ingredients as necessary for the particular indication being treated, preferably those with complementary activities that do not adversely affect each other. For example, it may be desirable to further provide a cytotoxic agent, e.g., a chemotherapeutic agent. Such active ingredients are suitably present in combination in amounts that are effective for the purpose intended.

Active ingredients may be entrapped in microcapsules prepared, for example, by coacervation techniques or by interfacial polymerization, for example, hydroxymethylcellulose or gelatin-microcapsules and poly-(methylmethacylate) microcapsules, respectively, in colloidal drug delivery systems (for example, liposomes, albumin microspheres, microemulsions, nano-particles and nanocapsules) or in macroemulsions. Such techniques are disclosed in *Remington's Pharmaceutical Sciences* 16th edition, Osol, A. Ed. (1980).

Sustained-release preparations may be prepared. Suitable examples of sustained-release preparations include semipermeable matrices of solid hydrophobic polymers containing the antibody, which matrices are in the form of shaped articles, e.g. films, or microcapsules.

The formulations to be used for in vivo administration are generally sterile. Sterility may be readily accomplished, e.g., by filtration through sterile filtration membranes.

G. Therapeutic Methods and Compositions

Any of the anti-Jagged antibodies provided herein may be used in therapeutic methods.

In one aspect, an anti-Jagged antibody for use as a medicament is provided. In further aspects, an anti-Jagged1 antibody for use in treating a disease or disorder associated with aberrant Notch signaling, e.g. a cancer, is provided. In certain embodiments, an anti-Jagged1 antibody for use in a method of treatment is provided. In certain embodiments, the invention provides an anti-Jagged1 antibody for use in a method of treating an individual having a cancer comprising administering to the individual an effective amount of the anti-Jagged1 antibody. In one such embodiment, the method further comprises administering to the individual an effective amount of at least one additional therapeutic agent, e.g., as described below. In further aspects, an anti-Jagged2 antibody for use in treating a cancer is provided. In certain embodiments, an anti-Jagged2 antibody for use in a method of treatment is provided. In certain embodiments, the invention provides an anti-Jagged2 antibody for use in a method of treating an individual having a cancer comprising administering to the individual an effective amount of the anti-Jagged2 antibody. In one such embodiment, the method further comprises administering to the individual an effective amount of at least one additional therapeutic agent, e.g., as described below.

In further embodiments, the invention provides an anti-Jagged antibody for use in inhibiting lung cancer growth. In certain embodiments, the invention provides an anti-Jagged1 antibody for use in a method of reducing lung cancer growth in an individual comprising administering to the individual an effective of the anti-Jagged1 antibody to reducing lung cancer growth. In certain embodiments, the invention provides an anti-Jagged2 antibody for use in a method of reducing lung cancer growth in an individual comprising administering to the individual an effective of the anti-Jagged2 antibody to reducing lung cancer growth. In certain embodiments, the invention provides an anti-Jagged1 antibody for use in a method of reducing breast cancer growth in an individual comprising administering to the individual an effective of the anti-Jagged1 antibody to reducing breast cancer growth. In certain embodiments, the invention provides an anti-Jagged2 antibody for use in a method of reducing breast cancer growth in an individual comprising administering to the individual an effective of the anti-Jagged2 antibody to reducing breast cancer growth. An "individual" according to any of the above embodiments is preferably a human.

In a further aspect, the invention provides for the use of an anti-Jagged antibody in the manufacture or preparation of a medicament. In one embodiment, the medicament is for treatment of a disease or disorder associated with aberrant Notch signaling. In one embodiment, the medicament is for treatment of a cancer. In a further embodiment, the medicament is for use in a method of treating a cancer comprising administering to an individual having a cancer an effective amount of the medicament. In one such embodiment, the method further comprises administering to the individual an effective amount of at least one additional therapeutic agent, e.g., as described below. An "individual" according to any of the above embodiments may be a human.

In a further aspect, the invention provides a method for treating a disease or disorder associated with aberrant Notch signaling. In one embodiment, the method comprises administering to an individual having such disease or disorder an effective amount of an anti-Jagged antibody. In one embodiment, the method comprises administering to an individual having a cancer an effective amount of an anti-Jagged1 antibody. In one such embodiment, the method further comprises administering to the individual an effective amount of at least one additional therapeutic agent, as described below. In one embodiment, the method comprises administering to an individual having a cancer an effective amount of an anti-Jagged2 antibody. In one such embodiment, the method further comprises administering to the individual an effective amount of at least one additional therapeutic agent, as described below. An "individual" according to any of the above embodiments may be a human.

In a further aspect, the invention provides a method for inhibiting cancer cell growth in an individual. In one embodiment, the method comprises administering to the individual an effective amount of an anti-Jagged1 antibody or anti-Jagged2 antibody to inhibiting cancer cell growth. In one embodiment, an "individual" is a human.

In a further aspect, the invention provides pharmaceutical formulations comprising any of the anti-Jagged antibodies provided herein, e.g., for use in any of the above therapeutic methods. In one embodiment, a pharmaceutical formulation comprises any of the anti-Jagged antibodies provided herein and a pharmaceutically acceptable carrier. In another embodiment, a pharmaceutical formulation comprises any of the anti-Jagged antibodies provided herein and at least one additional therapeutic agent, e.g., as described below.

Antibodies of the invention can be used either alone or in combination with other agents in a therapy. For instance, an antibody of the invention may be co-administered with at least one additional therapeutic agent. In certain embodiments, an additional therapeutic agent is a cytotoxic agent. In certain embodiments, an additional therapeutic agent is an antibody.

Such combination therapies noted above encompass combined administration (where two or more therapeutic agents are included in the same or separate formulations), and separate administration, in which case, administration of the antibody of the invention can occur prior to, simultaneously, and/or following, administration of the additional therapeutic agent or agents. In one embodiment, administration of the anti-Jagged antibody and administration of an additional therapeutic agent occur within about one month, or within about one, two or three weeks, or within about one, two, three, four, five, or six days, of each other. Antibodies of the invention can also be used in combination with radiation therapy.

An antibody of the invention (and any additional therapeutic agent) can be administered by any suitable means, including parenteral, intrapulmonary, and intranasal, and, if desired for local treatment, intralesional administration. Parenteral infusions include intramuscular, intravenous, intraarterial, intraperitoneal, or subcutaneous administration. Dosing can be by any suitable route, e.g. by injections, such as intravenous or subcutaneous injections, depending in part on whether the administration is brief or chronic. Various dosing schedules including but not limited to single or multiple administrations over various time-points, bolus administration, and pulse infusion are contemplated herein.

Antibodies of the invention would be formulated, dosed, and administered in a fashion consistent with good medical practice. Factors for consideration in this context include the particular disorder being treated, the particular mammal being treated, the clinical condition of the individual patient, the cause of the disorder, the site of delivery of the agent, the method of administration, the scheduling of administration, and other factors known to medical practitioners. The antibody need not be, but is optionally formulated with one or more agents currently used to prevent or treat the disorder in question. The effective amount of such other agents depends on the amount of antibody present in the formulation, the type of disorder or treatment, and other factors discussed above. These are generally used in the same dosages and with administration routes as described herein, or about from 1 to 99% of the dosages described herein, or in any dosage and by any route that is empirically/clinically determined to be appropriate.

For the prevention or treatment of disease, the appropriate dosage of an antibody of the invention (when used alone or in combination with one or more other additional therapeutic agents) will depend on the type of disease to be treated, the type of antibody, the severity and course of the disease, whether the antibody is administered for preventive or therapeutic purposes, previous therapy, the patient's clinical history and response to the antibody, and the discretion of the attending physician. The antibody is suitably administered to the patient at one time or over a series of treatments. Depending on the type and severity of the disease, about 1 µg/kg to 15 mg/kg (e.g. 0.1 mg/kg-10 mg/kg) of antibody can be an initial candidate dosage for administration to the patient, whether, for example, by one or more separate administrations, or by continuous infusion. One typical daily dosage might range from about 1 µg/kg to 100 mg/kg or more, depending on the factors mentioned above. For repeated administrations over several days or longer, depending on the condition, the treatment would generally be sustained until a desired suppression of disease symptoms occurs. One exemplary dosage of the antibody would be in the range from about 0.05 mg/kg to about 10 mg/kg. Thus, one or more doses of about 0.5 mg/kg, 2.0 mg/kg, 4.0 mg/kg or 10 mg/kg (or any combination thereof) may be administered to the patient. Such doses may be administered intermittently, e.g. every week or every three weeks (e.g. such that the patient receives from about two to about twenty, or e.g. about six doses of the antibody). An initial higher loading dose, followed by one or more lower doses may be administered. An exemplary dosing regimen comprises administering an initial loading dose of about 4 mg/kg, followed by a weekly maintenance dose of about 2 mg/kg of the antibody. However, other dosage regimens may be useful. The progress of this therapy is easily monitored by conventional techniques and assays.

It is understood that any of the above formulations or therapeutic methods may be carried out using an immunoconjugate of the invention in place of or in addition to an anti-Jagged antibody.

H. Articles of Manufacture

In another aspect of the invention, an article of manufacture containing materials useful for the treatment, prevention and/or diagnosis of the disorders described above is provided. The article of manufacture comprises a container and a label or package insert on or associated with the container. Suitable containers include, for example, bottles, vials, syringes, IV solution bags, etc. The containers may be formed from a variety of materials such as glass or plastic. The container holds a composition which is by itself or combined with another composition effective for treating, preventing and/or diagnosing the condition and may have a sterile access port (for example the container may be an intravenous solution bag or a vial having a stopper pierceable by a hypodermic injection needle). At least one active agent in the composition is an antibody of the invention. The label or package insert indicates that the composition is used for treating the condition of choice. Moreover, the article of manufacture may comprise (a) a first container with a composition contained therein, wherein the composition comprises an antibody of the invention; and (b) a second container with a composition contained therein, wherein the composition comprises a further cytotoxic or otherwise therapeutic agent. The article of manufacture in this embodiment of the invention may further comprise a package insert indicating that the compositions can be used to treat a particular condition. Alternatively, or additionally, the article of manufacture may further comprise a second (or third) container comprising a pharmaceutically-acceptable buffer, such as bacteriostatic water for injection (BWFI), phosphate-buffered saline, Ringer's solution and dextrose solution. It may further include other materials desirable from a commercial and user standpoint, including other buffers, diluents, filters, needles, and syringes.

It is understood that any of the above articles of manufacture may include an immunoconjugate of the invention in place of or in addition to an anti-Jagged antibody.

III. Examples

The following are examples of methods and compositions of the invention. It is understood that various other embodiments may be practiced, given the general description provided above.

Example 1. Generation of Anti-Jagged Antibodies a. Library Sorting and Screening to Identify Anti-Jagged1/2 Antibodies Human phage antibody libraries with synthetic diversities in the selected complementarity determining regions, mimicking the natural diversity of human IgG repertoire, were used for panning Fab fragments displayed on the surface of M13 bacteriophage particles. Human Jag1-DSL-EGF1-4 (SEQ ID NO:6) or human Jag2-DSL-EGF1-4 (SEQ ID NO:8) was used as antigen for library sorting. Nunc 96 well Maxisorp immunoplates were coated overnight at 4° C. with target antigen (10 μg/ml) and were blocked for 1 hour at room temperature with phage blocking buffer PBST (phosphate-buffered saline (PBS) and 1% (w/v) bovine serum albumin (BSA) and 0.05% (v/v) tween-20). Antibody phage libraries VH (see, e.g., Lee et al., J. Immunol. Meth. 284:119-132 (2004)) and VH/VL (see Liang et al., JMB. 366: 815-829 (2007)) were added to antigen plates separately and incubated overnight at room temperature. The following day antigen-coated plates were washed ten times with PBT (PBS with 0.05% Tween-20), and bound phage were eluted with 50 mM HCl and 500 mM NaCl for 30 minutes and neutralized with an equal volume of 1 M Tris base (pH7.5). Recovered phages were amplified in E. coli XL-1 Blue cells. During the subsequent selection rounds, incubation of antibody phage with the antigen-coated plates was reduced to 2-3 hours, and the stringency of plate washing was gradually increased.

After 4 rounds of panning, significant enrichment was observed. 96 clones were picked each from VH and VH/VL library sorting to determine whether they specifically bound to human Jagged1 or Jagged2. The variable regions of these clones were PCR sequenced to identify unique sequence clones. The affinities of phage antibodies were ranked using spot competition ELISA. The phage antibody IC50 values were further determined using competitive phage-binding ELISA. Unique phage antibodies that bind specifically to human Jagged1 (and not Jagged2), Jagged2 (and not Jagged1), or to both Jagged1 and Jagged2 were chosen and reformatted to full-length IgGs for evaluation in in vitro cell assays.

Clones of interest were reformatted into IgGs by cloning $V_L$ and $V_H$ regions of individual clones into a pRK mammalian cell expression vector (pRK.LPG3.HumanKappa) containing the human kappa constant domain, and expression vector (pRK.LPG4.HumanHC) encoding the full-length human IgG1 constant domain, respectively (Shields et al., J Biol Chem 2000; 276: 6591-6604). The antibodies were then transiently expressed in mammalian CHO cells, and purified with a protein A column.

b. Construction of Libraries for Affinity Improvement of Clones Derived from the $V_H$ or $V_HV_L$ Libraries Phagemid pW0703, derived from phagemid pV0350-2b (Lee et al., J. Mol. Biol 340, 1073-1093 (2004), containing stop codon (TAA) in all CDR-L3 positions and displaying monovalent Fab on the surface of M13 bacteriophage) served as the library templates for grafting heavy chain variable domains ($V_H$) of clones of interest from the $V_H$ library for affinity maturation. Both hard and soft randomization strategies were used for affinity maturation. For hard randomization, one light chain library with selected positions of the three light chain CDRs was randomized using amino acids designed to mimic natural human antibodies and the designed DNA degeneracy was as described in Lee et al. (J. Mol. Biol 340, 1073-1093 (2004)). To achieve the soft randomization conditions, which introduced the mutation rate of approximately 50% at the selected positions, the mutagenic DNA was synthesized with 70-10-10-10 mixtures of bases favoring the wild type nucleotides (Gallop et al., Journal of Medicinal Chemistry 37:1233-1251 (1994)). For soft randomization, residues at positions 91-96 of CDR-L3, 30-33, 35 of CDR-H1, 50, 52, 53-54, and 56 of CDR-H2, 95-98 of CDR-H3 were targeted; and three different combinations of CDR loops, H1/L3, H2/L3, and H3/L3, were selected for randomization.

For clones originated from $V_HV_L$ library, phagemids containing 4 stop codons (TAA) in each CDR and displaying monovalent Fab on the surface of M13 bacteriophage were generated individually, and served as the templates for kunkel mutagenesis for the construction of affinity maturation libraries. Only soft randomization strategy was used for clones derived from $V_HV_L$ library, as diversity of CDR-L3 was built into the naïve library. To achieve the soft randomization conditions, residues at positions 28-31 of CDR-L1, 50, 53-55 of CDR-L2, 91-96 of CDR-L3, 30-35 of CDR-H1, 50-56 of CDR-H2, 95-100 of CDR-H3 were targeted; and four different combinations of CDR loops, H1/L3*, H2/L3*, and H3/L3* and L1/L2/L3* (where * denotes the position of stop codons on the template), were selected for randomization.

c. Phage Sorting Strategy to Generate Affinity Improvement

For affinity improvement selection, Jag1 or Jag2 antigens were first biotinylated under limiting reagent condition. Phage libraries were subjected to one round of plate sorting and five rounds of solution sorting with increasing stringency. For the first round of plate sorting, 10 ug/ml antigen was first coated on Maxisorp plate and preblocked with blocking buffer (1% BSA and 0.05% Tween20 in PBS). 3 O.D./ml in blocking buffer of phage input were incubated to antigen plates for 3 hours. The wells were washed with PBS-0.05% Tween20 ten times. Bound phage was eluted with 150 μl/well 50 mM HCl, 500 mM KCl for 30 minutes, and subsequently neutralized by 50 μl/well of 1M Tris pH8, titered, and propagated for the next round. For subsequent rounds, panning of the phage libraries was done in solution phase, where phage library was incubated with 100 nM biotinylated target protein (the concentration is based on parental clone phage IC50 value) in 100 μl buffer containing 1% Superblock (Pierce Biotechnology) and 0.05% Tween20 for 2 hours at room temperature. The mixture was further diluted 10× with 1% Superblock, and 100 μl/well was applied to neutravidin-coated wells (10 μg/ml) for 30 minutes at room temperature with gentle shaking. To determine background binding, control wells containing phage were captured on neutravidin-coated plates. Bound phage was then washed, eluted and propagated as described for first round. Five more rounds of solution sorting were carried out together with increasing selection stringency. The first couple rounds of which is for on-rate selection by decreasing biotinylated target protein concentration from 100 nM to 0.1 nM, and the last two rounds of which is for off-rate selection by adding excess amounts of non-biotinylated target protein (300 to 1000 fold more) to compete off weaker binders at room temperature.

d. High Throughput Affinity Screening ELISA (Single Spot Competition)

Colonies were picked from the sixth round of screening. Colonies were grown overnight at 37° C. in 150 μl/well of 2YT media with 50 μg/ml carbenicillin and $1 \times 10^{10}$/ml M13KO7 in 96-well plate (Falcon). From the same plate, a colony of XL-1 infected parental phage was picked as control. 96-well Nunc Maxisorp plates were coated with 100 μl/well of either Jag1 or Jag2 (0.5 μg/ml) in PBS at 4° C. overnight. The plates were blocked with 150 μl of 1% BSA and 0.05% Tween20 in PBS 20 for 1 hour.

35 μl of the phage supernatant was diluted with to 75 μl of in ELISA (enzyme linked immunosorbent assay) buffer (PBS with 0.5% BSA, 0.05% Tween20) with or without 5 nM Jag1 or Jag2 and let incubate for 1 hour at room temperature in an F plate (NUNC). 95 μl of mixture was transferred side by side to the antigen coated plates. The plate was gently shaken for 15 min and was washed ten times with PBS-0.05% Tween 20. The binding was quantified by adding horseradish peroxidase (HRP)-conjugated anti-M13 antibody in ELISA buffer (1:2500) and incubated for 30 minutes at room temperature. The plates were washed with PBS-0.05% Tween 20 ten times. Next, 100 μl/well of Peroxidase substrate was added to the well and incubated for 5 minutes at room temperature. The reaction was stopped by adding 100 μl 0.1M Phosphoric Acid ($H_3PO_4$) to each well and allowed to incubate for 5 minutes at room temperature. The O.D. (optical density) of the yellow color in each well was determined using a standard ELISA plate reader at 450 nm. In comparison to the $OD_{450\ nm}$ reduction (%) of the well of parental phage (100%), clones that had the $OD_{450\ nm}$ reduction (%) lower than 50% were picked for sequence analysis. Unique clones were selected for phage preparation to determine binding affinity (phage IC50) against either Jag1 or Jag2 by comparison to respective parental clones. Then the most affinity-improved clones were reformatted into human IgG1 for antibody production and further BIAcore binding kinetic analysis and other in vitro or in vivo assay.

Example 2. Specific Binding of Antibodies Generated Against Jagged1 or Jagged2 Antigens Antibodies D-1 (FIG. 10A, left panel) and C-1 (FIG. 10A, right panel) were tested for binding to recombinant purified Notch ligands human Jagged1 (hJag-1), human Jagged2 (hJag-2), murine Jagged2 (mJag-2), human Delta-like 1 (hDLL1), murine Delta-like 1 (mDLL1), and human Delta-like 4 (hDLL4) using a standard enzyme-linked immunosorbent assay (ELISA). 1 μg/ml of Notch ligand protein in PBS, pH7.4, were coated on ELISA plates (Nunc Maxisorp) at 40° C. overnight, including human Jagged1, human and murine Jagged2, and human and murine Delta-like 1 (DLL-1). Plates were blocked with Casein blocker in PBS (Pierce) for one hour at room temperature. Serial 3-fold dilutions of anti-Jagged1/2 IgGs in PBST buffer (PBT buffer (PBS+0.05% (v/v) Tween 20) with 0.5% (w/v) BSA) were added to the plates and incubated for one hour at room temperature. The plates were then washed with PBST and bound antibodies were detected with peroxidase-conjugated goat anti-human Fab specific IgG (Sigma). TMB substrate (3,3',5,5'-tetramethylbenzidine) was used and absorbance at 650 nM was read using a standard ELISA plate reader. Absorbance was plotted against concentrations of IgGs using KaleidaGraph (Synergy Software). FIG. 10A depicts the results, with $OD_{450}$ on the y-axis representing the extent of binding. None of the antibodies obtained in the first round of antibody screening described in Example 1 selectively recognized only Jagged1 or only Jagged2. D-1 binds human and mouse Jagged1 as well as human and murine Jagged2 (FIG. 10A, left panel, and data not shown). C-1 binds human and murine Jagged1, human and murine Jagged2, and human and murine Delta-like 1 (FIG. 10A, right panel, and data not shown). Neither antibody bound to human Delta-like 4.

Figure 10B:
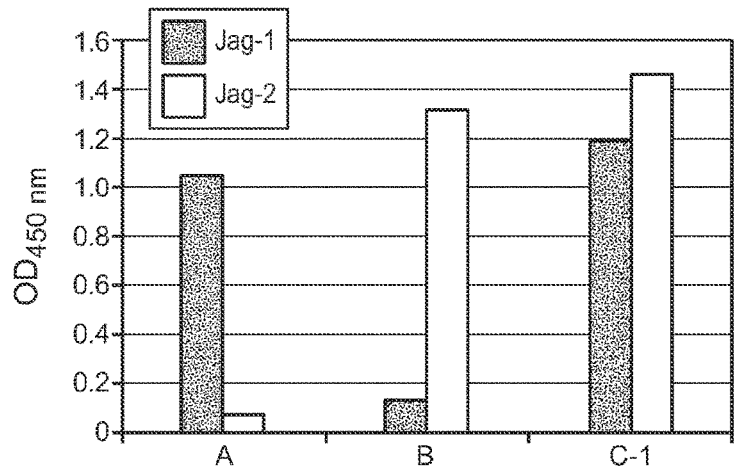

Further screening rounds identified antibodies specific for only one of the Jagged family members, as determined by ELISA. Antibody A bound human and murine Jagged1, but not Jagged2 (FIG. 10B). Conversely, antibody B bound human and murine Jagged2, but not Jagged1 (FIG. 10B). C-1 served as a control for binding to both Jagged1 and Jagged2.

Example 3. Antibody Binding Affinities and Epitope Mapping

Binding affinities of anti-Jagged1/2 phage antibodies were measured by Surface Plasmon Resonance (SRP) using a BIAcore™-3000 instrument. Anti-Jagged1/2 phage human IgGs were captured by mouse anti-human IgG coated on the CM5 sensor chip to achieve approximately 150 response units (RU). For kinetics measurements, two-fold serial dilutions of human or mouse Jag1/2 DSL_EGF1-4 (1.95 nM to 250 nM) were injected in PBT buffer (PBS with 0.05% Tween 20) at 25° C. with a flow rate of 30 ml/min. Association rates ($k_{on}$) and dissociation rates ($k_{off}$) were calculated using a simple one-to-one Langmuir binding model (BIAcore Evaluation Software version 3.2). The equilibrium dissociation constant ($k_d$) was calculated as the ratio $k_{off}/k_{on}$.

FIG. 11 summarizes the binding constants for antibodies A, A-1, A-2, B, B-1, B-2, B-3, B-4, C, C-1, D, D-1, and D-2 binding to purified human Jagged1, human Jagged2, and mouse Jagged2. Parent antibody A specifically bound to human and murine Jagged1 (FIG. 11 and data not shown). The affinity matured antibodies A-1 and A-2 bound both human and murine Jagged1 with high affinity (FIG. 11). Antibodies A, A-1 and A-2 did not bind human or murine Jagged2 (FIG. 11). Conversely, none of antibody B, B-1, B-2, B-3, or B-4 bound human or murine Jagged1. The affinity matured antibodies B-1, B-2, B-3, or B-4 specifically bound to human and mouse Jagged2 (FIG. 11 and data not shown). Antibodies C, C-1, D, D-1, D-2, D-3, D-4, and D-5 bound to both human and murine Jagged1 and Jagged2 (FIG. 11). With regard to Jagged1, binding of antibodies C, C-1, D, D-1, D-2, D-3, D-4, and D-5 was mapped to a DSL-EGF1-4 fragment of Jagged1 using H ISA cross-blocking experiments.

Figure 12:
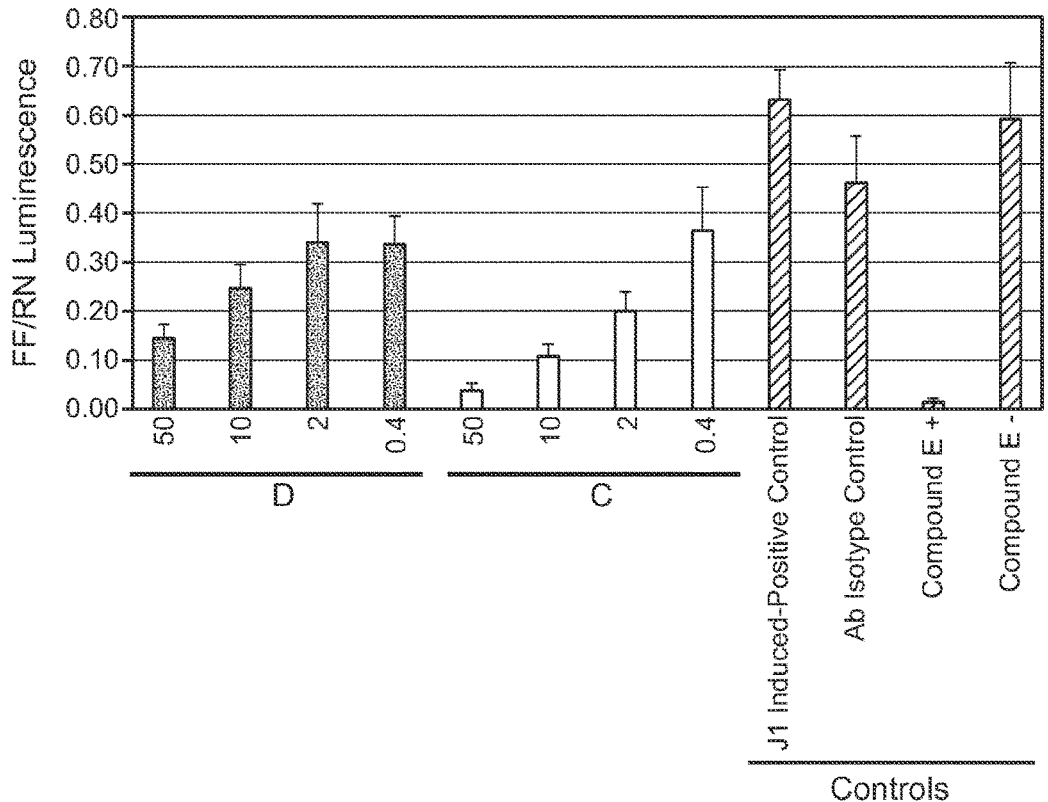
FIG. 12 shows dose-dependent inhibition of Jagged1-induced signaling of Notch 1 by anti-Jagged antibodies. Results were obtained from co-culture experiments that measure Jagged1-induced signaling through the Notch1 receptor, as described in Example 4. The y-axis indicates expression levels of the Notch-dependent reporter gene firefly luciferase relative to expression of a control gene (constitutively active promoter driving expression of *Renilla luciferase*). The x-axis indicates concentrations for antibodies D and C (0.4-50 μg/ml). Co-culture without antibodies (J1 induced-positive control) served as positive control for Jagged1-induced signaling. An isotype control antibody served as control for specific antibody inhibition. A gamma secretase inhibitor (Compound E+) was used as control for inhibition of Notch signaling.

Example 4. Anti-Jagged Antagonist Antibodies Inhibit Jagged1-Induced Signaling In Vitro To determine whether anti-Jagged antibodies can act as antagonists of Jagged-induced Notch signaling, co-culture experiments were performed essentially as described by Wu et al., Nature 464, 1052-1057 (15 Apr. 2010). NIH-3T3 cells engineered to express Jagged1, as the Notch ligand, were co-cultured with NIH 3T3 cells that stably express Notch1 and that were transiently transfected to express a Notch-responsive TP-1 (12X CSL) firefly luciferase reporter and a constitutively expressed Renilla luciferase reporter (pRL-CMV, Promega). Strong Notch reporter signal (Firefly luciferase) was observed in the co-culture (FIG. 12, J1 induced-Positive Control). Reporter expression was reduced to background levels when a γ-secretase inhibitor was added to the co-culture (FIG. 12, Compound E+), demonstrating Notch-dependent expression of the reporter construct.

Addition of increasing amounts (0.4-50 µg/ml) of anti-Jagged antibodies C or D resulted in dose-dependent inhibition of reporter expression (FIG. 12, compare C and D to J1 induced-Positive Control). In contrast, an isotype control antibody that does not recognize Jagged or Notch did not significantly reduce reporter gene expression (FIG. 12, Ab Isotype Control). Taken together these results demonstrate that antibodies C and D act as antagonists, i.e., inhibit Jagged1-mediated signaling through the Notch receptor Notch1 in a dose-dependent manner.

Figure 13A:
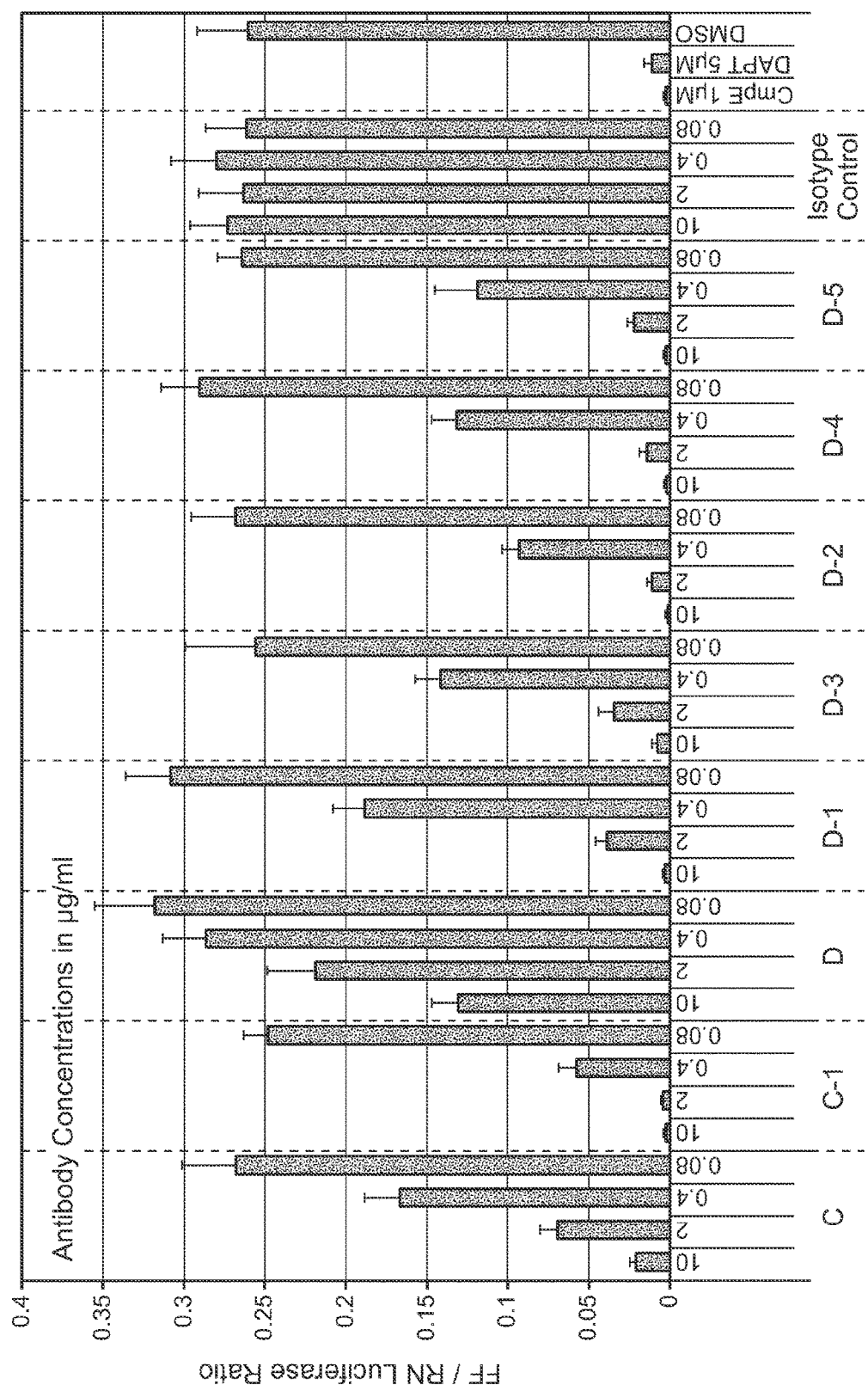
FIGS. 13A-B show inhibition of Notch signaling by affinity matured anti-Jagged antibodies. Co-culture assays were performed as described in FIG. 12 and Example 4. (A) Phage antibodies and their concentrations (μg/me are indicated on the x-axis (parental antibodies C and D served as control). The gamma-secretase inhibitors (GSIs) Compound E (CmpE) and N—[N-(3,5-Difluorophenacetyl)-L-alanyl]-S-phenylglycine t-butyl ester (DAPT) at the indicated concentrations served as positive control for inhibition of Notch signaling; DMSO served as vehicle control for the GSIs; an irrelevant antibody with the same isotype as those tested in the panel served as isotype control. (B) Phage antibodies at the indicated concentration are indicated on the x-axis. DAPT at the indicated concentrations served as positive control for inhibition of Notch signaling; DMSO served as vehicle control. Signaling was induced by Jagged1 (dark gray columns) or by Jagged2 (light gray columns). Untreated=cultures that were not stimulated with ligand and not treated with antibody; No Stimulation or 3T3P=cultures not stimulated with ligand; agD or gD=isotype control antibody; Stim/no AB or No Ab=cultures stimulated with ligand but not treated with antibody; gamma-secretase inhibitor DAPT or the DAPT vehicle control of DMSO.

Similar results were obtained with affinity-matured antibodies tested in the above-described co-culture assay for their ability to inhibit Jagged1-mediated Notch signaling. As the respective parental antibodies C and D, affinity-matured antibodies C-1, D-1, D-2, D-3, D-4 and D-5 inhibited Jagged1-mediated Notch signaling in a dose-dependent manner, whereas no inhibition was observed for the isotype control (FIG. 13A).

Example 5. Anti-Jagged Antagonist Antibodies Inhibit Jagged1-Induced Signaling In Vitro Antibodies C and D, and their respective affinity-matured descendants, bind to both human and murine Jagged1, and human and murine Jagged2 (e.g., FIG. 10A). To determine whether antibodies selective for Jagged1 only or Jagged2 only could selectively inhibit Jagged1 and/or 2-induced Notch signaling, respectively, the co-culture experiments described in Example 4 were repeated with the Jagged1-specific antibody A-2 or the Jagged2-specific antibody B-3. Signaling was induced by Jagged1 (FIG. 13B, dark gray columns) or by Jagged2 (FIG. 13B, light gray columns) and inhibition was determined as described in Example 4 using the antibodies at concentrations of 0.016-50 µg/ml. Controls included cultures that were not stimulated with ligand and not treated with antibody (FIG. 1B3, Untreated), not stimulated with ligand (FIG. 13B, No Stimulation or 3T3P), treated with 5-10 µg/ml isotype control antibody (FIG. 13B, agD or gD), stimulated with ligand but not treated with antibody (Stim/no AB or No Ab), treated with 5 µM of the gamma-secretase inhibitor DAPT or the DAPT vehicle control of DMSO.

Figure 13B:
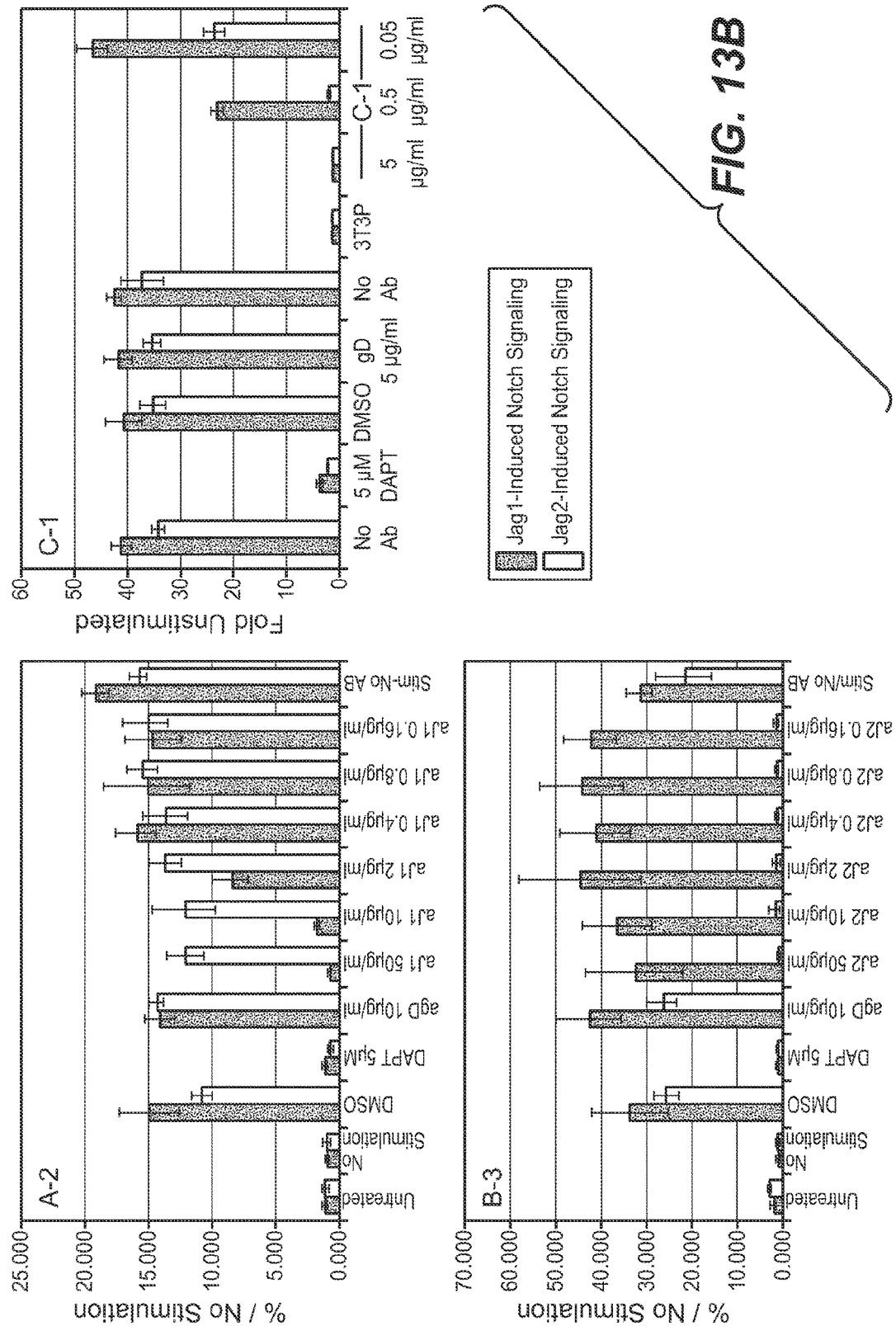

Antibody A-2 inhibited Jagged1-induced signaling, but not Jagged2-induced signaling, in a dose-dependent manner (FIG. 13B, top left panel). The $IC_{50}$ for A-2 was between 2 and 10 µg/ml for Jagged1 inhibition whereas little or no Jagged2 inhibition was observed even at the highest concentration of 50 µg/ml. The results demonstrate that antibody A-2 is a Jagged1-selective antagonist, i.e., antibody A-2 inhibits Jagged1-mediated signaling, but not Jagged2-mediated signaling. In contrast, antibody B-3 potently inhibited Jagged2-induced signaling at the lowest concentration tested but did not inhibit Jagged1-induced signaling at the highest concentration tested, thus establishing B-3 as a Jagged1-selective antagonist (bottom left panel). Antibody C-1 inhibited both Jagged1- and Jagged2-induced signaling, in a dose-dependent manner (top right panel). Taken together, the results show that A-2 and B-3 function as Jagged1 and Jagged2 selective inhibitors, respectively, whereas C-1 functions as an inhibitor of both Jagged1 and Jagged2.

Example 6. Effect of Anti-Jagged Antibody Treatment on Body Weight

Figure 14A:
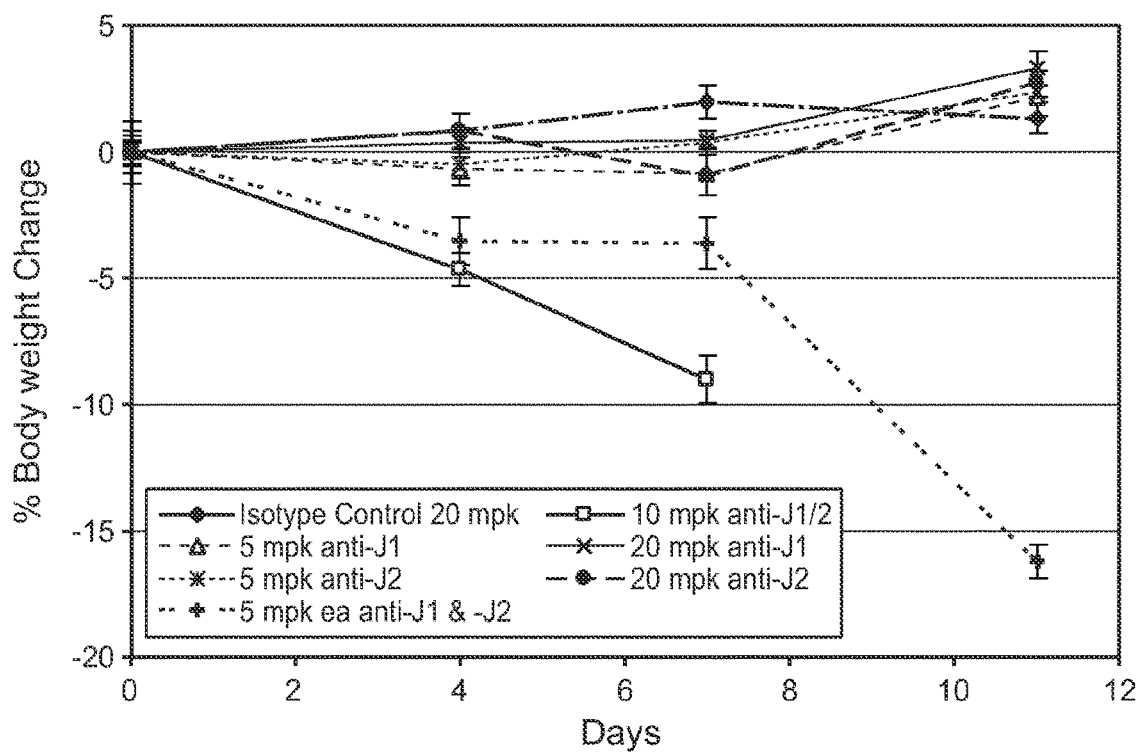
FIGS. 14A-B show that combined inhibition of Jagged1 and Jagged2 causes rapid weight loss. (A) Mice were dosed twice per week with the anti-Jagged1/2 antibody C-1 (anti-J1/2; 5-10 mpk), the anti-Jagged1 antibody A-2 (anti-J1; 5-20mpk), the anti-Jagged2 antibody B-3 (anti-J2; 5-20mpk), the antibody A-2 and B-3 together (anti-J1 & -2; 5mpk each) or an isotype control antibody (20mpk). Total antibody concentration of each dosing was brought up to 20mpk with the isotype control antibody, where necessary. The average body weight changes (y-axis) are graphed as a percentage of starting body weight over time (x-axis). (B) Balb/c mice (ten per group, individually housed) were injected IP twice per week with either 30 mpk of anti-gD isotype control antibody or with a combination of 15 mpk antibody A-2 plus 15 mpk antibody B-3 for eight days. Food intake was assessed by daily weighing of the food delivered and remaining in each cage. Error bars represent standard deviations (n=10).
Figure 14B:
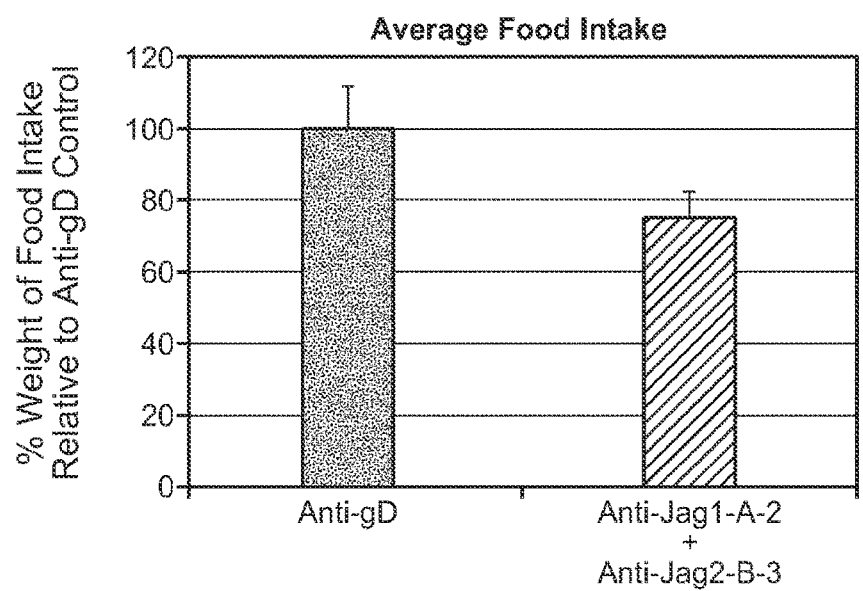

As described above, gamma-secretase inhibitors, and other inhibitors of multiple Notch receptors, cause weight loss and intestinal goblet cell metaplasia, which is undesirable for clinical administration. To determine how the antibodies described herein affect body weight and intestinal health, mice were dosed twice per week with the anti-Jagged1/2 antibody C-1 (5-10 mg antibody per kg mouse body weight (mpk)), the anti-Jagged1 antibody A-2 (5-20mpk), the anti-Jagged2 antibody B-3 (5-20mpk), the antibody A-2 and B-3 together (5mpk each) or the isotype control anti-gD antibody (20mpk). The isotype control antibody was also used to bring the total antibody concentration of each dosing to 20 mpk. Total body weight of each mouse was determined prior to first administration of antibodies and monitored until day 12 of the study. The average body weight changes are depicted in FIG. 14, graphed as a percentage of starting body weight. Dual inhibition of Jagged1 and Jagged2, using either the anti-Jagged1/2 antibody C-1 or a combination of the Jagged1-specific antibody A-2 and the Jagged2-specific antibody B-3 together, caused rapid and substantial weight loss (FIG. 14A). By day 4, some mice that received the anti-Jagged1/2 antibody C-1 had lost over 5% of their bodyweight, which progressed to nearly 8-10% loss in body weight by day 7 (FIG. 14A). Mice that received both A-2 and B-3 also lost weight rapidly, in some cases up to 17% by day 11 (FIG. 14A). In contrast, none of the Jagged1-specific or Jagged2-specific antibodies alone caused weight loss over the course of the study at either 5 or 20mpk (FIG. 14A). Treatment with the combination of anti-Jagged1 plus anti-Jagged2 antibodies resulted in decreased food intake (FIG. 14B), which correlated with the observed decrease in body weight (FIG. 14A) and suggested that decreased food intake could partly or entirely account for the correlated body weight decreases.

Example 7. Intestinal Histology Following Anti-Jagged Antibody Treatment

Pan-Notch inhibition, e.g., by gamma-secretase inhibitors, as well as combined inhibition of Notch1 plus Notch2 or Dll1 plus Dll4 (see Wu et al., Nature 2010; Pellegrinet et al., Gastroenterology, 2011), causes goblet cell metaplasia in mice, and this metaplasia has been hypothesized to be responsible for the observed weight loss.

Figure 15A:
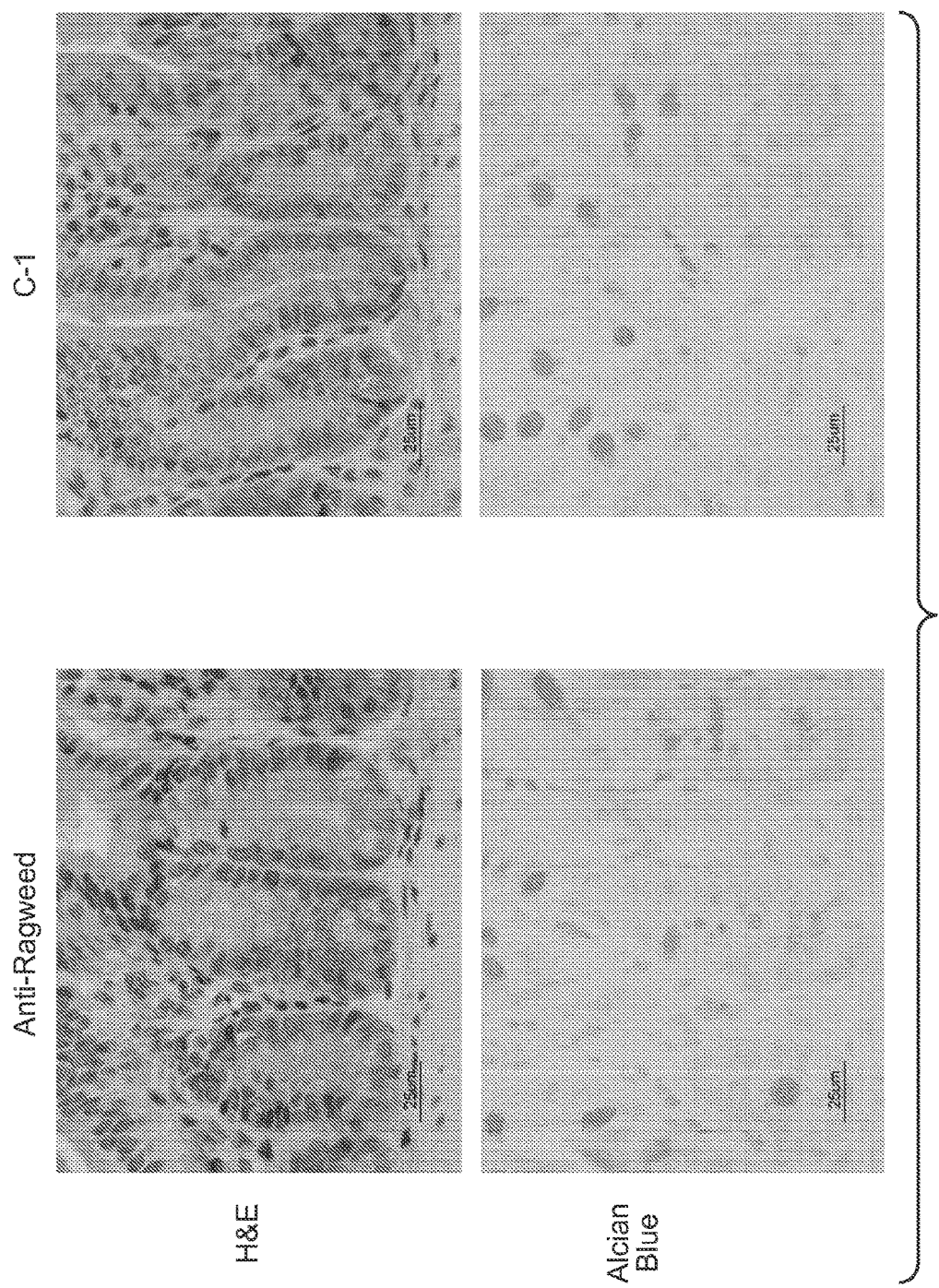

To determine if the rapid loss of body weight following combined inhibition of Jagged1 and Jagged2 observed in Example 6 was similarly associated with goblet cell metaplasia, intestinal samples of the mice treated as described in Example 6 were isolated and examined Intestines were stained with hematoxylin and eosin (FIG. 15A, H & E) or with Alcian Blue for mucous, a marker of secretory goblet cells (FIG. 15A, Alcian Blue). Some samples were analyzed by immunohistochemistry for expression of lysozyme, a marker of Paneth cells, or for the proliferation marker Ki-67 (FIG. 15B). No obvious differences could be observed between histology or marker expression in intestinal sections of mice treated with either control antibody or the anti-Jagged1/2 antibody C-1. These results suggest that the weight loss observed following inhibition of both Jagged1 and 2 cannot be attributed to goblet cell metaplasia. Moreover, these results uncover a novel mechanism for weight loss following treatment with Notch inhibitors, indicating that goblet cell metaplasia may be insufficient to explain weight loss following treatment with pan-Notch inhibitors.

Example 8. Anti-Jagged1 Antagonist Antibodies Inhibit Human Lung Cancer Cell Growth In Vivo Harlan athymic nude mice were inoculated subcutaneously with Calu-6 cells, a human non-small cell lung cancer line. After tumor volume reached approximately 200 cubic mm, mice were injected intraperitoneally (IP) twice per week (days 0, 4, 7, 11, 14 and 18) with 20 mpk of either anti-gD isotype control antibody (n=10) or with anti-Jagged1 antibody A-2 (n=10). Tumor volume in each mouse was measured with calipers for another 19 days. Total body weight of each mouse was monitored over the course of the study.

Figures 1, 16B:
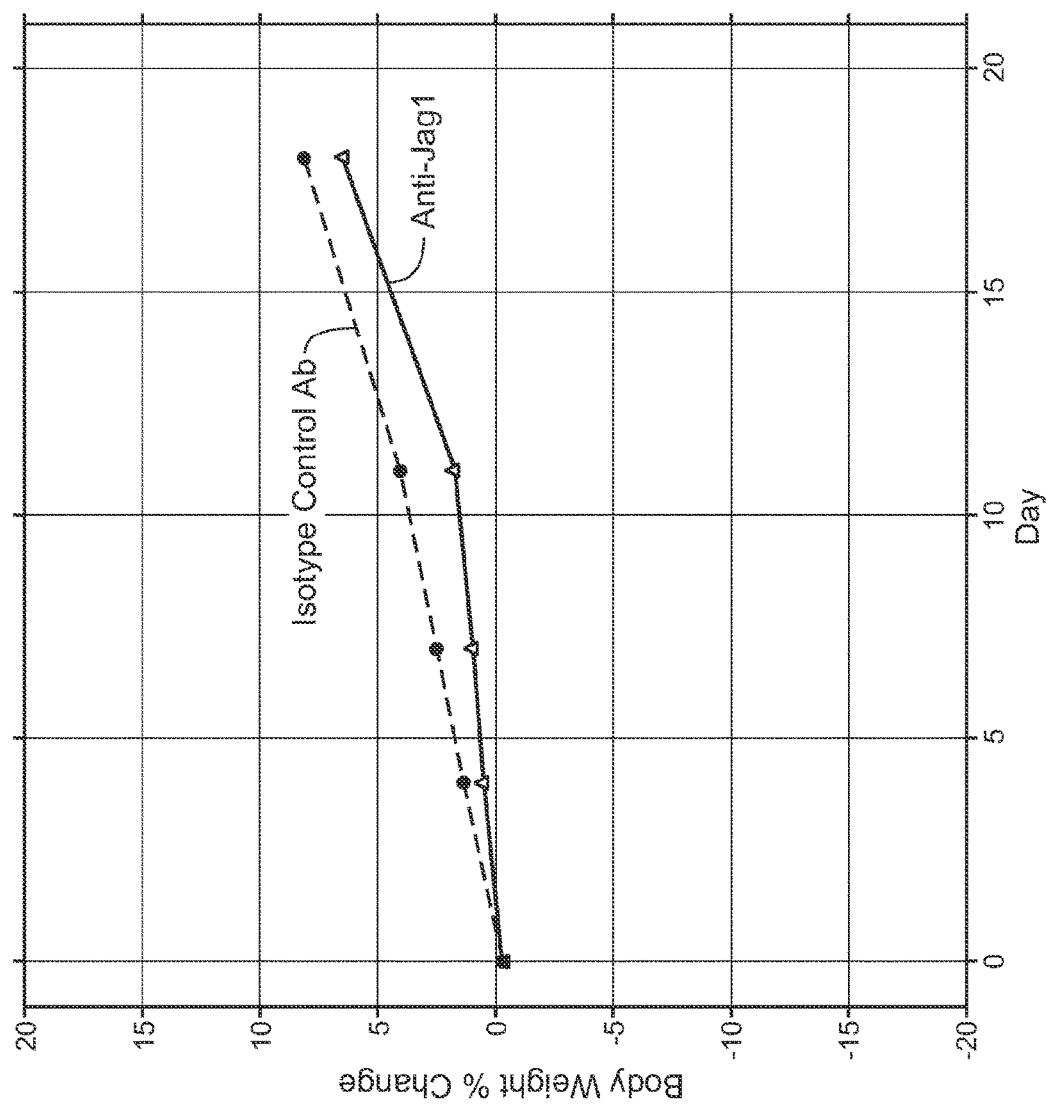
Figures 2, 16B:
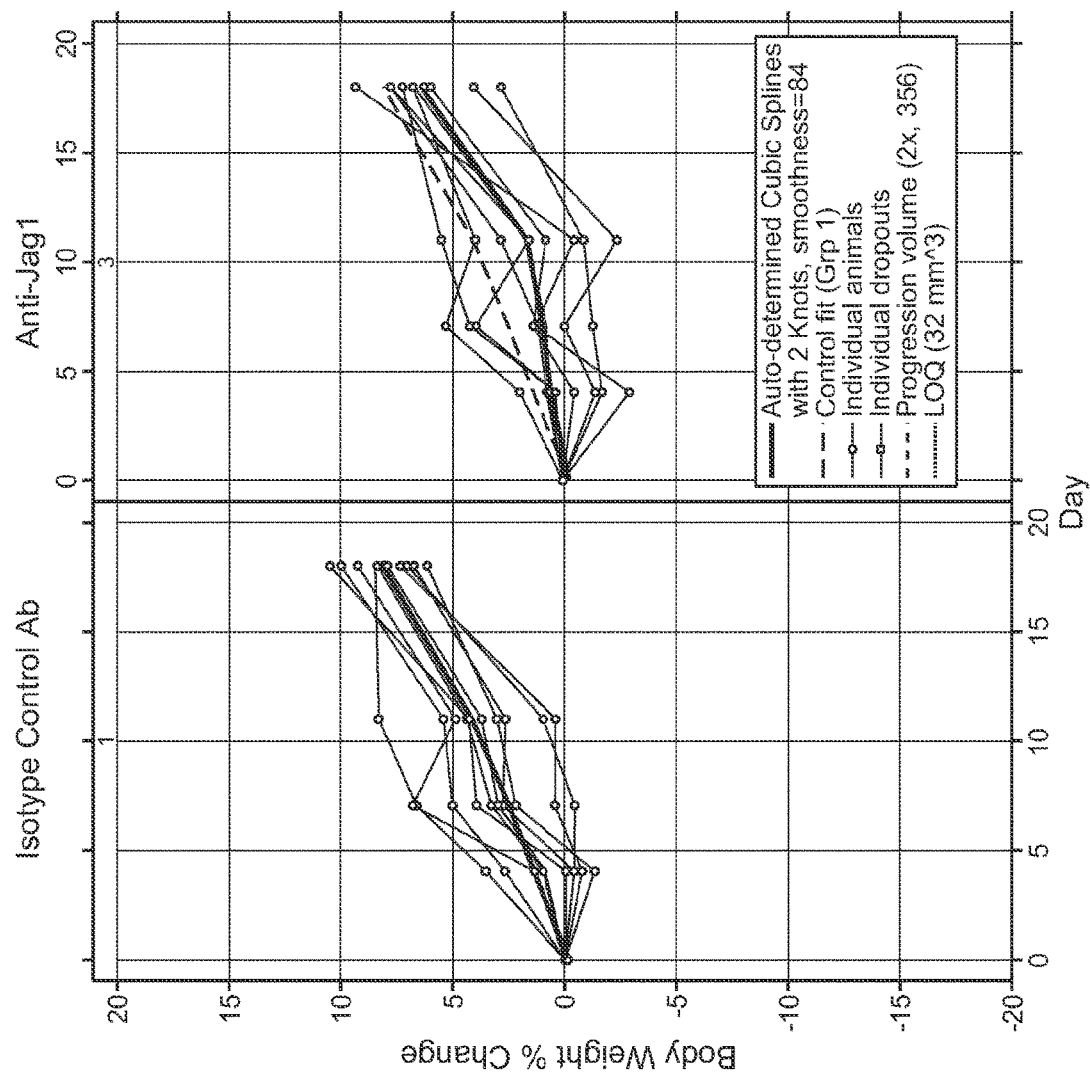

Tumors in mice treated with anti-Jagged1 showed a significant decrease in tumor volume relative to tumors in the control group (FIG. 16A). The effect of the anti-Jagged1 antibody treatment could be detected as early as day seven after treatment (FIG. 16A). At day 18, the average tumor volume in mice that received the anti-Jagged1 antibody reached approximately 500 mm$^3$, while average tumor volume in control animals reached approximately 750 mm$^3$ at day 18. No significant change in body weight between the treatment and control group could be observed (FIG. 16B).

Figure 17A:
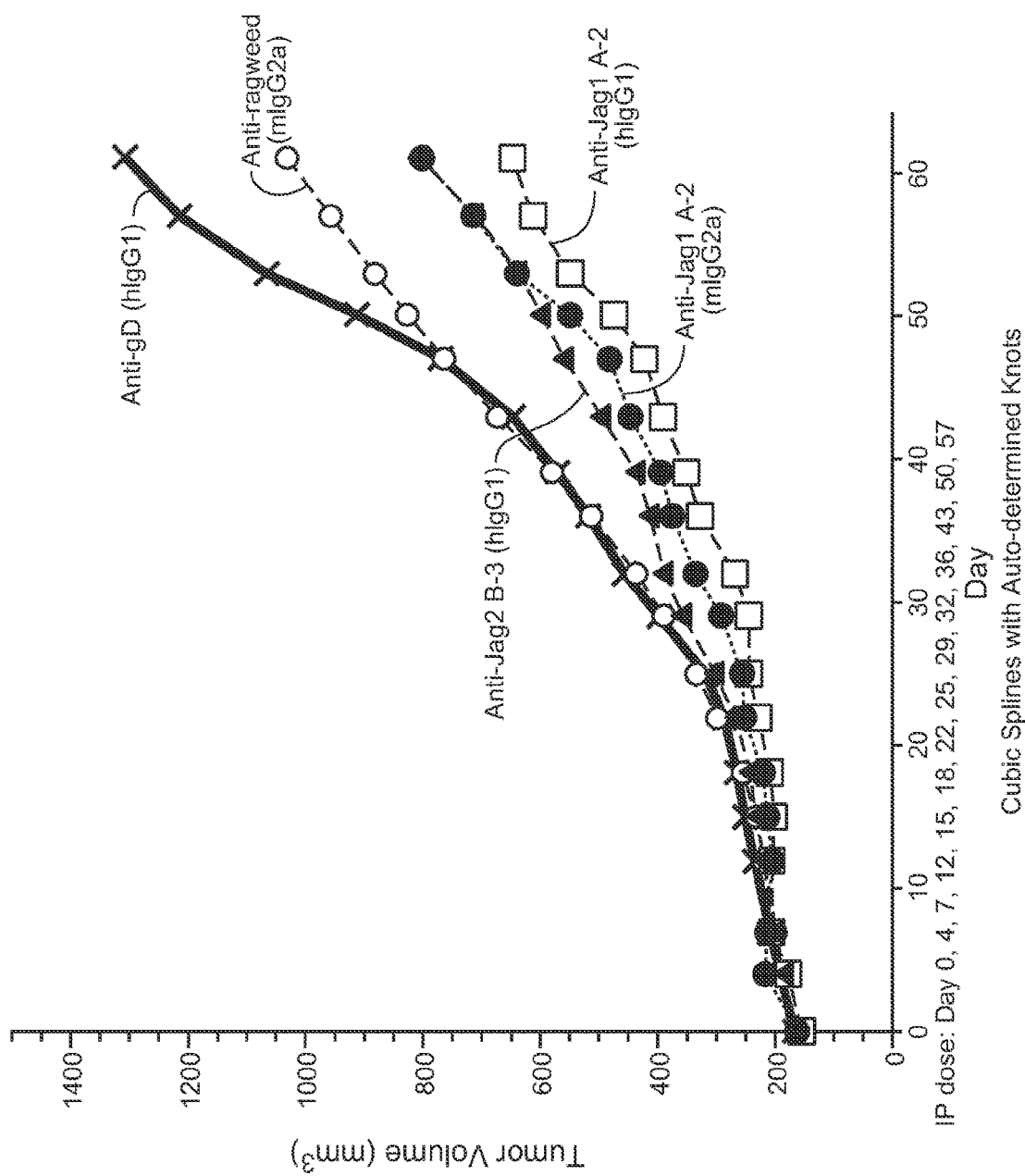
FIGS. 17A-B show inhibition of human breast cancer cell growth by anti-Jagged1 and anti-Jagged2 antagonist antibodies in vivo. C.B-17 SCID.bg mice with human breast cancer xenografts were injected on days 0, 4, 7, 12, 15, 18, 22, 25, 29, 32, 36, 43, 50, and 57 with anti-gD isotype control antibody (Anti-gD), anti-ragweed isotype control antibody (anti-ragweed), anti-Jagged1 antibody A-2 in the human IgG1 backbone (anti-Jag1 A-2 (hIgG1)), anti-Jagged1 antibody A-2 in the murine IgG2a backbone (anti-Jag1 A-2 (mIgG2a)), or anti-Jagged2 antibody B-3 in the human IgG1 backbone (anti-Jag2 B-3 (hIgG1)). Tumor volumes (y-axis) of treatment groups (A) or individual animals (B) were plotted using a linear mixed effects model over time (x-axis).
Figure 17B:
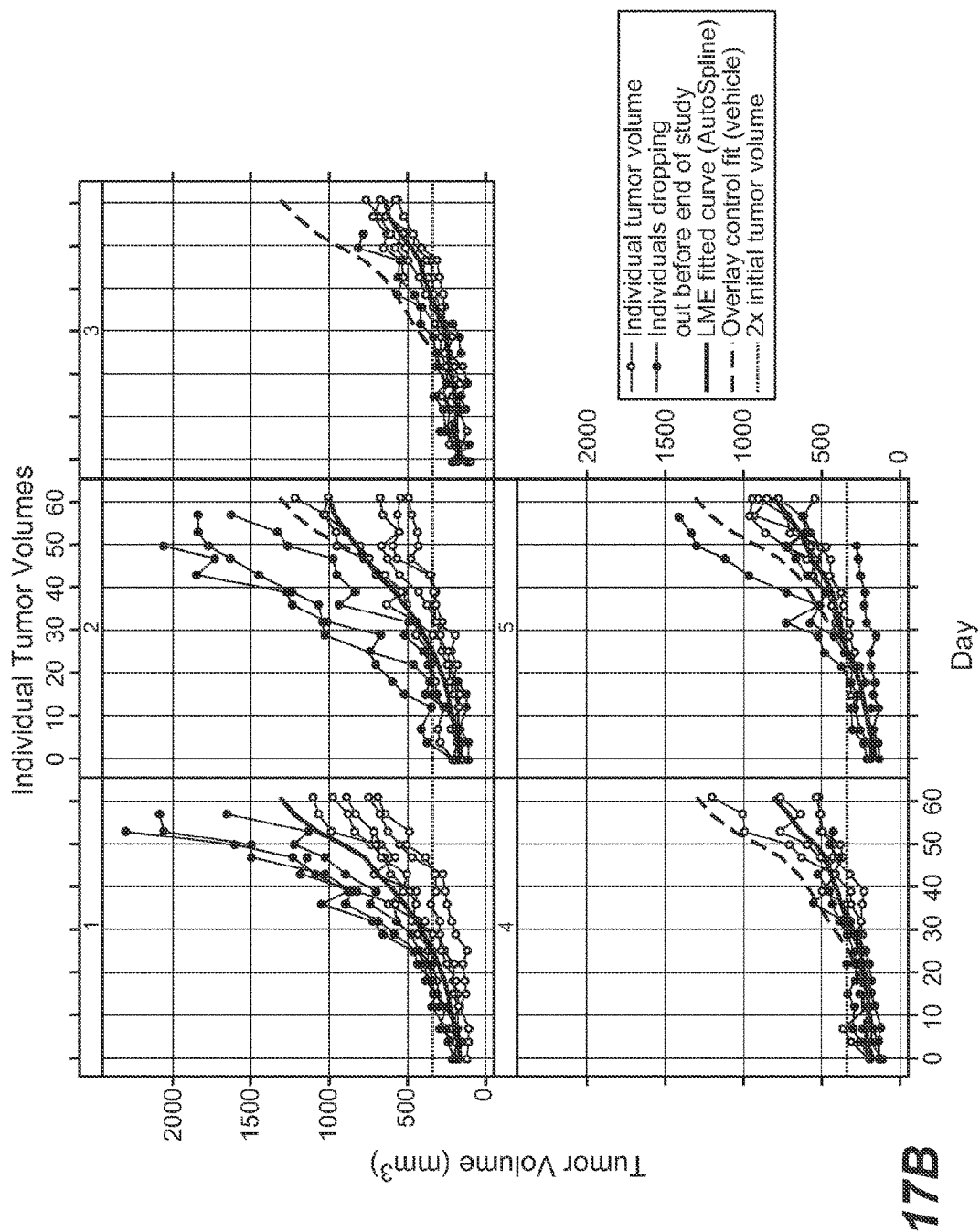

Example 9. Anti-Jagged1 and Anti-Jagged2 Antibodies Inhibit Human Breast Cancer Cell Growth In Vivo C.B-17 SCID.bg mice were inoculated in the mammary fat pad with MDA-MD-468 cells, a human basal breast cancer line. After tumor volume reached approximately 200 cubic mm, mice were dosed IP with 30 mpk of either anti-gD isotype control antibody (human IgG1 isotype), anti-ragweed isotype control antibody (murine IgG2a isotype), anti-Jagged1 antibody A-2 in the human IgG1 backbone, anti-Jagged1 antibody A-2 in the murine IgG2a backbone or anti-Jagged2 antibody B-3 in the human IgG1 backbone on days 0, 4, 7, 12, 15, 18, 22, 25, 29, 32, 36, 43, 50, and 57. Tumor volume (y-axis) was measured with calipers for 60 days after the first injection. The tumor volumes for each group (n=9 per group) were plotted using a linear mixed effects model (FIG. 17A). Tumor volumes for each mouse in each group are depicted in FIG. 17B.

All three anti-Jagged antibodies significantly inhibited tumor growth. Both anti-Jagged1 antibodies inhibited tumor growth to a similar extent, demonstrating that the observed anti-tumor growth properties are consistent and independent of the antibody backbone.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

What is claimed is:

1. An isolated antibody that binds to Jagged1, the antibody comprising:
    (a) HVR-H1 comprising the amino acid sequence of SEQ ID NO:81;
    (b) HVR-H2 comprising an amino acid sequence of SEQ ID NO:84;
    (c) HVR-H3 comprising an amino acid sequence of SEQ ID NO:87;
    (d) HVR-L1 comprising the amino acid sequence of SEQ ID NO:110;
    (e) HVR-L2 comprising the amino acid sequence of SEQ ID NO:111; and
    (f) HVR-L3 comprising an amino acid sequence of SEQ ID NO:114.

2. The antibody of claim 1, wherein the antibody comprises:
    (a) an HVR-H1 comprising the amino acid sequence of SEQ ID NO:81;
    an HVR-H2 comprising the amino acid sequence of SEQ ID NO:82;
    an HVR-H3 comprising the amino acid sequence of SEQ ID NO:85;
    an HVR-L1 comprising the amino acid sequence of SEQ ID NO:110;
    an HVR-L2 comprising the amino acid sequence of SEQ ID NO:111; and
    an HVR-L3 comprising the amino acid sequence of SEQ ID NO:112; or
    (b) an HVR-H1 comprising the amino acid sequence of SEQ ID NO:81;
    an HVR-H2 comprising the amino acid sequence of SEQ ID NO:82;
    an HVR-H3 comprising the amino acid sequence of SEQ ID NO:86;
    an HVR-L1 comprising the amino acid sequence of SEQ ID NO:110;
    an HVR-L2 comprising the amino acid sequence of SEQ ID NO:111; and
    an HVR-L3 comprising the amino acid sequence of SEQ ID NO:113; or
    (c) an HVR-H1 comprising the amino acid sequence of SEQ ID NO:81;
    an HVR-H2 comprising the amino acid sequence of SEQ ID NO:83;
    an HVR-H3 comprising the amino acid sequence of SEQ ID NO:85;
    an HVR-L1 comprising the amino acid sequence of SEQ ID NO:110;
    an HVR-L2 comprising the amino acid sequence of SEQ ID NO:111; and
    an HVR-L3 comprising the amino acid sequence of SEQ ID NO:112.

3. The antibody of claim 2, further comprising a light chain variable domain framework FR1 comprising the amino acid sequence of SEQ ID NO:60; FR2 comprising the amino acid sequence of SEQ ID NO:61; FR3 comprising the amino acid sequence of SEQ ID NO:62; and FR4 comprising the amino acid sequence of SEQ ID NO:135.

4. The antibody of claim 2, comprising a heavy chain variable domain framework FR1 comprising the amino acid sequence of SEQ ID NO:50; FR2 comprising the amino acid sequence of SEQ ID NO:136; FR3 comprising the amino acid sequence of SEQ ID NO:57; and FR4 comprising the amino acid sequence of SEQ ID NO:35.

5. The antibody of claim 2, comprising (a) a VH sequence having at least 95% sequence identity to the amino acid sequence of SEQ ID NO:10; (b) a VL sequence having at least 95% sequence identity to the amino acid sequence of SEQ ID NO:19; or (c) a VH sequence as in (a) and a VL sequence as in (b).

6. The antibody of claim 5, comprising a VH sequence of SEQ ID NO:10.

7. The antibody of claim 5, comprising a VL sequence of SEQ ID NO:19.

8. The antibody of claim 2, comprising (a) a VH sequence having at least 95% sequence identity to the amino acid sequence of SEQ ID NO:11; (b) a VL sequence having at least 95% sequence identity to the amino acid sequence of SEQ ID NO:20; or (c) a VH sequence as in (a) and a VL sequence as in (b).

9. The antibody of claim 8, comprising a VH sequence of SEQ ID NO:11.

10. The antibody of claim 8, comprising a VL sequence of SEQ ID NO:20.

11. A method of treating an individual having a cancer comprising administering to the individual an effective amount of the antibody of claim 2.

12. The method of claim 11, wherein the cancer is selected from the group consisting of: breast cancer, lung cancer, brain cancer, cervical cancer, colon cancer, liver cancer, bile duct cancer, pancreatic cancer, skin cancer, B-cell malignancies, and T-cell malignancies.

13. The antibody of claim 1, which is a monoclonal antibody.

14. The antibody of claim 1, which is a human, humanized, or chimeric antibody.

15. The antibody of claim 1, which is an antibody fragment.

16. The antibody of claim 1, which is a full length IgG1 antibody.

17. The antibody of claim 1, wherein the antibody is an antagonist of Jagged1-mediated signaling.

18. An immunoconjugate comprising the antibody of claim 1 and a cytotoxic agent.

19. A pharmaceutical formulation comprising the antibody of claim 1 and a pharmaceutically acceptable carrier.

20. An antibody comprising a VH sequence of SEQ ID NO:10 and a VL sequence of SEQ ID NO:19.

21. An antibody comprising a VH sequence of SEQ ID NO:11 and a VL sequence of SEQ ID NO:20.

* * * * *